(12) United States Patent
Newberry

(10) Patent No.: US 10,945,676 B2
(45) Date of Patent: Mar. 16, 2021

(54) SYSTEM AND METHOD FOR BLOOD TYPING USING PPG TECHNOLOGY

(71) Applicant: SANMINA CORPORATION, San Jose, CA (US)

(72) Inventor: Robert Steven Newberry, New Hope, AL (US)

(73) Assignee: Sanmina Corporation, San Jose, CA (US)

( * ) Notice: Subject to any disclaimer, the term of this patent is extended or adjusted under 35 U.S.C. 154(b) by 333 days.

(21) Appl. No.: 16/019,518

(22) Filed: Jun. 26, 2018

(65) Prior Publication Data

US 2018/0303433 A1   Oct. 25, 2018

Related U.S. Application Data

(60) Division of application No. 15/867,632, filed on Jan. 10, 2018, now Pat. No. 10,039,500, and a (Continued)

(51) Int. Cl.
*A61B 5/1455*   (2006.01)
*A61B 5/024*   (2006.01)
(Continued)

(52) U.S. Cl.
CPC .......... *A61B 5/7275* (2013.01); *A61B 5/0002* (2013.01); *A61B 5/0022* (2013.01); (Continued)

(58) Field of Classification Search
CPC .............. A61B 5/1455; A61B 5/14551; A61B 5/14552; A61B 5/14532; A61B 5/7275; A61B 5/743; A61B 5/7225; A61B 5/6817
See application file for complete search history.

(56) References Cited

U.S. PATENT DOCUMENTS 4,913,150 A   4/1990   Cheung et al.
5,115,133 A   5/1992   Knudson
(Continued)

FOREIGN PATENT DOCUMENTS

CN   102609627 A   7/2012
EP   2017001250 A1   1/2017
(Continued)

OTHER PUBLICATIONS

KC Manhesh et al., Wearable Wireless Intelligent Multi-Parameter Health Monitoring Watch, 2013, Texas nstruments India Educators' Conference, IEEE, p. 61-64.
(Continued)

*Primary Examiner* — Eric F Winakur
(74) *Attorney, Agent, or Firm* — Loza & Loza, LLP; Jessica Smith

(57) ABSTRACT

A biosensor identifies a blood type using photoplethysmography (PPG) technology. A PPG circuit obtains a plurality of spectral responses at a plurality of wavelengths detected from skin of a user. A processing circuit determines a blood factor indicator using the plurality of spectral responses. The blood factor indicator may include a signal quality parameter or a ratio R value. A calibration database includes a correlation of the blood factor indicator to a plurality of blood types. The blood type of the user is identified using the blood factor indicator and the calibration database.

19 Claims, 35 Drawing Sheets

Related U.S. Application Data continuation-in-part of application No. 15/859,147, filed on Dec. 29, 2017, now Pat. No. 10,194,871, and a continuation-in-part of application No. 15/811,479, filed on Nov. 13, 2017, now Pat. No. 10,238,346, and a continuation-in-part of application No. 15/804,581, filed on Nov. 6, 2017, now Pat. No. 10,231,674, and a continuation-in-part of application No. 15/718,721, filed on Sep. 28, 2017, now Pat. No. 10,517,515, and a continuation-in-part of application No. 15/680,991, filed on Aug. 18, 2017, now Pat. No. 9,968,289, said application No. 15/718,721 is a continuation of application No. 15/622,941, filed on Jun. 14, 2017, now Pat. No. 9,788,767, application No. 16/019,518, which is a continuation-in-part of application No. 15/490,813, filed on Apr. 18, 2017, now Pat. No. 9,980,676, and a continuation-in-part of application No. 15/489,391, filed on Apr. 17, 2017, now Pat. No. 9,974,451, and a continuation-in-part of application No. 15/485,816, filed on Apr. 12, 2017, now Pat. No. 10,155,087, and a continuation-in-part of application No. 15/462,700, filed on Mar. 17, 2017, now Pat. No. 10,500,354, said application No. 15/804,581 is a continuation of application No. 15/404,117, filed on Jan. 11, 2017, application No. 16/019,518, which is a continuation-in-part of application No. 15/400,916, filed on Jan. 6, 2017, said application No. 15/485,816 is a continuation of application No. 15/276,760, filed on Sep. 26, 2016, now Pat. No. 9,636,457, said application No. 15/489,391 is a continuation of application No. 15/275,444, filed on Sep. 25, 2016, now Pat. No. 9,642,538, said application No. 15/490,813 is a continuation of application No. 15/275,388, filed on Sep. 24, 2016, now Pat. No. 9,642,578, application No. 16/019,518, which is a continuation-in-part of application No. 14/866,500, filed on Sep. 25, 2015, now Pat. No. 10,321,860.

(60) Provisional application No. 62/463,104, filed on Feb. 24, 2017, provisional application No. 62/457,138, filed on Feb. 9, 2017, provisional application No. 62/613,388, filed on Jan. 3, 2018.

(51) Int. Cl.
*A61B 5/00* (2006.01)
*A61B 5/145* (2006.01)

(52) U.S. Cl.
CPC ........ *A61B 5/02416* (2013.01); *A61B 5/1455* (2013.01); *A61B 5/14532* (2013.01); *A61B 5/14551* (2013.01); *A61B 5/6817* (2013.01); *A61B 5/743* (2013.01); *A61B 5/6826* (2013.01); *A61B 5/7225* (2013.01); *A61B 2560/0223* (2013.01)

(56) References Cited

U.S. PATENT DOCUMENTS

| | | | |
|---|---|---|---|
| 5,269,310 A | 12/1993 | Jones et al. | |
| 5,358,703 A | 10/1994 | Lai | |
| 5,515,847 A | 5/1996 | Braig et al. | |
| 5,673,692 A | 10/1997 | Schulze et al. | |
| 5,823,966 A | 10/1998 | Buchert | |
| 5,947,911 A | 9/1999 | Wong et al. | |
| 5,983,121 A | 11/1999 | Tsuchiya | |
| 6,087,087 A | 7/2000 | Yonetani et al. | |
| 6,280,390 B1 | 8/2001 | Akselrod et al. | |
| 6,285,896 B1 | 9/2001 | Tobler et al. | |
| 6,305,804 B1 | 10/2001 | Rice et al. | |
| 6,537,225 B1 | 3/2003 | Mills | |
| 6,694,180 B1 | 2/2004 | Boesen | |
| 6,719,705 B2 | 4/2004 | Mills | |
| 6,819,950 B2 | 11/2004 | Mills | |
| 6,921,367 B2 | 7/2005 | Mills | |
| 6,985,763 B2 | 1/2006 | Boas et al. | |
| 7,154,592 B2 | 12/2006 | Reynolds et al. | |
| 7,167,736 B2 | 1/2007 | Winther | |
| 7,171,251 B2 | 1/2007 | Sarussi et al. | |
| 7,179,228 B2 | 2/2007 | Banet | |
| 7,209,775 B2 | 4/2007 | Bae et al. | |
| 7,291,497 B2 | 11/2007 | Holmes et al. | |
| 7,356,364 B1 * | 4/2008 | Bullock | A61B 5/14532 600/310 |
| 7,371,562 B2 | 5/2008 | Cunningham et al. | |
| 7,608,045 B2 | 10/2009 | Mills | |
| 7,647,083 B2 | 1/2010 | Al-Ali et al. | |
| 7,761,127 B2 | 7/2010 | Al-Ali et al. | |
| 7,763,472 B2 | 7/2010 | Doctor et al. | |
| 7,764,982 B2 | 7/2010 | Dalke et al. | |
| 7,941,199 B2 | 5/2011 | Kiani | |
| 3,224,411 A1 | 7/2012 | Al-Ali et al. | |
| 8,224,411 B2 | 7/2012 | Al-Ali et al. | |
| 8,255,027 B2 | 8/2012 | Al-Ali et al. | |
| 8,328,420 B2 | 12/2012 | Abreu | |
| 8,385,996 B2 | 2/2013 | Smith et al. | |
| 8,401,605 B2 | 3/2013 | Huiku | |
| 8,483,787 B2 | 7/2013 | Al-Ali et al. | |
| 8,494,507 B1 | 7/2013 | Tedesco et al. | |
| 8,597,274 B2 | 12/2013 | Sloan et al. | |
| 8,652,040 B2 | 2/2014 | Leboeuf et al. | |
| 8,676,284 B2 | 3/2014 | He | |
| 8,730,047 B2 | 5/2014 | Ridder et al. | |
| 8,868,149 B2 | 10/2014 | Eisen et al. | |
| 8,888,701 B2 | 11/2014 | Leboeuf et al. | |
| 8,906,693 B2 | 12/2014 | Schultz et al. | |
| 8,923,918 B2 | 12/2014 | Kreger et al. | |
| 8,961,932 B2 | 2/2015 | Silverman | |
| 9,022,973 B2 | 5/2015 | Sexton et al. | |
| 9,131,882 B2 | 9/2015 | Al-Ali et al. | |
| 9,149,216 B2 | 10/2015 | Eisen et al. | |
| 9,149,646 B2 | 10/2015 | Keswarpu et al. | |
| 9,387,033 B2 | 7/2016 | Yodfat et al. | |
| 9,442,092 B2 | 9/2016 | Lane | |
| 9,521,970 B2 | 12/2016 | Hoppe et al. | |
| 9,554,738 B1 | 1/2017 | Gulati et al. | |
| 9,642,578 B2 | 5/2017 | Newberry | |
| 9,668,701 B2 | 6/2017 | Maarek | |
| 9,713,428 B2 | 7/2017 | Chon et al. | |
| 9,739,663 B2 | 8/2017 | Halder et al. | |
| 9,820,656 B2 | 11/2017 | Olivier | |
| 9,839,381 B1 | 12/2017 | Weber et al. | |
| 9,924,895 B2 | 3/2018 | Rawicz et al. | |
| 9,949,675 B2 | 4/2018 | Miller | |
| 9,999,355 B2 | 6/2018 | Kirenko | |
| 10,028,682 B2 | 7/2018 | Thiele | |
| D824,937 S | 8/2018 | Sparandara et al. | |
| 10,099,554 B2 | 10/2018 | Steeg et al. | |
| 10,130,285 B1 | 11/2018 | Singamsetty et al. | |
| 10,153,796 B2 | 12/2018 | Fung et al. | |
| 10,181,021 B2 | 1/2019 | Venkatraman et al. | |
| 10,206,619 B1 | 2/2019 | Lee et al. | |
| 10,215,698 B2 | 2/2019 | Han et al. | |
| 10,227,063 B2 | 3/2019 | Abreu | |
| 10,232,156 B2 | 3/2019 | Netzel et al. | |
| 10,278,591 B2 | 5/2019 | Gil | |
| D850,316 S | 6/2019 | Ennis et al. | |
| 10,314,500 B2 | 6/2019 | Olivier | |
| 10,322,728 B1 | 6/2019 | Porikli et al. | |
| 10,342,495 B2 | 7/2019 | Melkoniemi et al. | |
| 10,349,847 B2 | 7/2019 | Kwon et al. | |
| 10,420,470 B2 | 9/2019 | Kwon et al. | |
| 10,420,491 B2 | 9/2019 | Rajan et al. | |
| 10,433,726 B2 | 10/2019 | Ramesh et al. | |
| 10,433,738 B2 | 10/2019 | Thomas et al. | |
| 10,433,739 B2 | 10/2019 | Weekly et al. | |
| 10,463,283 B2 | 11/2019 | Ferber et al. | |
| 2002/0049389 A1 | 4/2002 | Abreu | |

(56) References Cited

U.S. PATENT DOCUMENTS

| | | |
|---|---|---|
| 2003/0229276 A1 | 12/2003 | Sarussi et al. |
| 2004/0078219 A1 | 4/2004 | Kaylor et al. |
| 2004/0100376 A1 | 5/2004 | Lye et al. |
| 2004/0157341 A1 | 8/2004 | Reynolds et al. |
| 2005/0101841 A9 | 5/2005 | Kaylor et al. |
| 2005/0209516 A1 | 9/2005 | Fraden |
| 2005/0228244 A1 | 10/2005 | Banet |
| 2005/0228299 A1 | 10/2005 | Banet |
| 2005/0245831 A1 | 11/2005 | Banet |
| 2006/0009698 A1 | 1/2006 | Banet |
| 2006/0094942 A1 | 5/2006 | Winther |
| 2006/0287589 A1 | 12/2006 | Wobermin et al. |
| 2007/0202605 A1 | 8/2007 | Doctor et al. |
| 2007/0203405 A1 | 8/2007 | Shimomura |
| 2007/0260132 A1 | 11/2007 | Sterling |
| 2008/0146890 A1 | 6/2008 | Leboeuf et al. |
| 2008/0165017 A1 | 7/2008 | Schwartz |
| 2008/0208019 A1 | 8/2008 | Nitzan |
| 2008/0241199 A1 | 10/2008 | Silverman |
| 2009/0043178 A1 | 2/2009 | Belotserkovsky |
| 2009/0156988 A1 | 6/2009 | Ferren et al. |
| 2009/0187167 A1 | 7/2009 | Sexton et al. |
| 2009/0287120 A1 | 11/2009 | Ferren et al. |
| 2010/0049020 A1 | 2/2010 | Dalke et al. |
| 2010/0191080 A1 | 7/2010 | Mills |
| 2010/0274101 A1 | 10/2010 | Lin et al. |
| 2010/0331631 A1 | 12/2010 | MacLaughlin |
| 2011/0082355 A1 | 4/2011 | Eisen et al. |
| 2011/0106050 A1 | 5/2011 | Yodfat et al. |
| 2011/0137141 A1 | 6/2011 | Razoumov et al. |
| 2011/0160697 A1 | 6/2011 | Yodfat et al. |
| 2011/0166553 A1 | 7/2011 | Holmes et al. |
| 2011/0224518 A1 | 9/2011 | Tindi et al. |
| 2011/0237464 A1 | 9/2011 | Cunningham et al. |
| 2011/0275978 A1 | 11/2011 | Hyde et al. |
| 2012/0010683 A1 | 1/2012 | Keswarpu et al. |
| 2012/0029363 A1 | 2/2012 | Lund |
| 2012/0095302 A1 | 4/2012 | Adhikari |
| 2012/0131507 A1 | 5/2012 | Sparandara et al. |
| 2012/0136054 A1 | 5/2012 | Schultz et al. |
| 2012/0156933 A1 | 6/2012 | Kreger et al. |
| 2012/0203077 A1 | 8/2012 | He et al. |
| 2012/0238844 A1 | 9/2012 | Grata et al. |
| 2012/0330126 A1 | 12/2012 | Hope et al. |
| 2013/0030259 A1 | 1/2013 | Thomsen et al. |
| 2013/0060098 A1 | 3/2013 | Thomsen et al. |
| 2013/0066176 A1 | 3/2013 | Addison et al. |
| 2013/0110311 A1 | 5/2013 | Steeg et al. |
| 2013/0310669 A1 | 11/2013 | Meir Nitzan |
| 2014/0046160 A1 | 2/2014 | Terashima et al. |
| 2014/0100432 A1 | 4/2014 | Golda et al. |
| 2014/0112940 A1 | 4/2014 | Lane |
| 2014/0194342 A1 | 7/2014 | Zhang et al. |
| 2014/0243648 A1 | 8/2014 | Dubielczyk |
| 2014/0253709 A1 | 9/2014 | Bresch et al. |
| 2014/0275852 A1 | 9/2014 | Hong et al. |
| 2014/0297313 A1 | 10/2014 | Condurso et al. |
| 2014/0316226 A1 | 10/2014 | Ferber et al. |
| 2015/0066238 A1 | 3/2015 | Todd et al. |
| 2015/0088007 A1 | 3/2015 | Bardy et al. |
| 2015/0094914 A1 | 4/2015 | Abreu |
| 2015/0105638 A1 | 4/2015 | Eisen et al. |
| 2015/0109617 A1 | 4/2015 | Gilbert et al. |
| 2015/0148622 A1 | 5/2015 | Moyer et al. |
| 2015/0148635 A1 | 5/2015 | Benaron |
| 2015/0150453 A1 | 6/2015 | Abreu |
| 2015/0157269 A1* | 6/2015 | Lisogurski ......... A61B 5/14551 600/301 |
| 2015/0182172 A1 | 7/2015 | Shelley et al. |
| 2015/0229341 A1 | 8/2015 | Fung et al. |
| 2015/0250404 A1 | 9/2015 | Maarek |
| 2015/0282747 A1 | 10/2015 | Thiele |
| 2015/0366471 A1 | 12/2015 | LeBoeuf et al. |
| 2016/0018257 A1 | 1/2016 | Mirov et al. |
| 2016/0058308 A1 | 3/2016 | Robinson |
| 2016/0058347 A1 | 3/2016 | Reichgott et al. |
| 2016/0066863 A1 | 3/2016 | Thaveeprungsriporn et al. |
| 2016/0100781 A1 | 4/2016 | Bechtel et al. |
| 2016/0262707 A1 | 9/2016 | Devries |
| 2016/0367154 A1 | 12/2016 | Gladshtein et al. |
| 2017/0027521 A1 | 2/2017 | Geva et al. |
| 2017/0050518 A1 | 2/2017 | Steeg et al. |
| 2017/0071550 A1 | 3/2017 | Newberry |
| 2017/0091436 A1 | 3/2017 | Cao |
| 2017/0172477 A1 | 6/2017 | Adusumilli et al. |
| 2017/0215811 A1 | 8/2017 | Newberry |
| 2017/0256110 A1 | 9/2017 | DiVincent et al. |
| 2017/0347894 A1 | 12/2017 | Bhushan et al. |
| 2017/0347899 A1 | 12/2017 | Bhushan et al. |
| 2018/0117291 A1 | 5/2018 | Netzel et al. |
| 2018/0125431 A1 | 5/2018 | Newberry |
| 2018/0140210 A1 | 5/2018 | Jelfs et al. |
| 2018/0140237 A1 | 5/2018 | Rajan et al. |
| 2018/0177416 A1 | 6/2018 | Church et al. |
| 2018/0177440 A1 | 6/2018 | Jelfs et al. |
| 2018/0200433 A1 | 7/2018 | Cirit |
| 2018/0264242 A1 | 9/2018 | Hoffman et al. |
| 2018/0353137 A1 | 12/2018 | Balajadia et al. |
| 2018/0358119 A1 | 12/2018 | Bhushan et al. |
| 2019/0046039 A1 | 2/2019 | Ramesh et al. |
| 2019/0050622 A1 | 2/2019 | Cabibihan et al. |
| 2019/0086331 A1 | 3/2019 | Han |
| 2019/0099114 A1 | 4/2019 | Mouradian et al. |
| 2019/0110745 A1 | 4/2019 | Linnes et al. |
| 2019/0125963 A1 | 5/2019 | Mou et al. |
| 2019/0125964 A1 | 5/2019 | Mou et al. |
| 2019/0133471 A1 | 5/2019 | Olson et al. |
| 2019/0192085 A1 | 6/2019 | Krishna et al. |
| 2019/0192086 A1 | 6/2019 | Krishna et al. |
| 2019/0251238 A1 | 8/2019 | Venkatraman et al. |
| 2019/0358387 A1 | 11/2019 | Elbadry et al. |

FOREIGN PATENT DOCUMENTS

| | | |
|---|---|---|
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2016157156 A1 | 10/2016 |
| WO | 2017001249 A1 | 1/2017 |
| WO | 2017053925 A1 | 3/2017 |
| WO | 2018206875 A1 | 11/2018 |
| WO | 2019030700 A1 | 2/2019 |
| WO | 2019118053 A1 | 6/2019 |

OTHER PUBLICATIONS

Abdallah et al., Design of a Compact Multi-Sensor System for Non-Invasive Glucose Monitoring Using Optical Spectroscopy, International Conference on Electronics, Biomedical Engineering and its Applications (ICEBEA'2012), Jan. 7-8, 2012, p. 310-317.

Forst et al., Cardiovascular Effects of Disturbed Insulin Activity in Metabolic Syndrome and in Type 2 Diabetic Patients, Insulin Secretion and Action, Horm Metab Res; 2009, 41; p. 123-131.

Mohamed Elgendi, On the Analysis of Fingertip Photoplethysmogram Signals, Current Cardiology Reviews, 2012, 8, p. 14-25, Bentham Science Publishers.

Wikipedia, Cytochrome P450, Dec. 31, 2015, p. 1-12.

Oliver Wieben, Light Absorbance in Pulse Oximetry, Taylor & Francis, 1997, IOP Publishing, p. 1-20.

Wikipedia, Photoplethysmogram, Jul. 25, 2015, p. 1-4.

PCT/US2016/053631 . Int'l search Report & Written Opinion (dated Dec. 8, 2016).

(56) References Cited

OTHER PUBLICATIONS

Babbage, "A cardiac biometric recognition system hopes to replace passwords and keys." Economist.com (May 9, 2013).
Elgendi, "On the analysis of fingertip photoplethysmogram signals." Current Cardiology Reviews 8:14-25 (2012).
Kanade, "BioOptics: blood type determination based on image processing techniques by utilizing an optical sensor device." Int'l J. Science & Res, vol. 5:7 (Jul. 2016).
PCT/US2018/038127. Int'l Search Report & Written Opinion (dated Sep. 10, 2018).

* cited by examiner

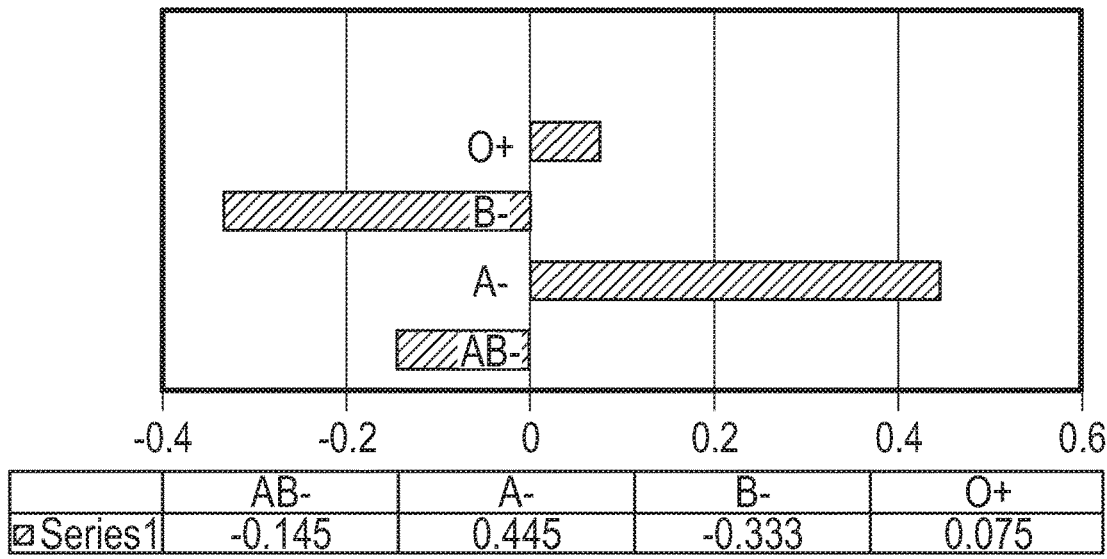

FIG. 32

```
3300
  │
  ▼
┌─────────────────────────────────────┐
│ Obtain test population with a specific │ ─3302
│           blood type                │
└─────────────────────────────────────┘
  │
  ▼
┌─────────────────────────────────────┐
│ Determine average R values over a   │ ─3304
│       range of SPO2 values          │
└─────────────────────────────────────┘
  │
  ▼
┌─────────────────────────────────────┐
│ Determine recalibration error to    │ ─3306
│     standard calibration curve      │
└─────────────────────────────────────┘
  │
  ▼
┌─────────────────────────────────────┐
│ Obtain SPO2 calibration curve for   │ ─3308
│        specific blood type          │
└─────────────────────────────────────┘
```

FIG. 33

SYSTEM AND METHOD FOR BLOOD TYPING USING PPG TECHNOLOGY

CROSS REFERENCE TO RELATED APPLICATIONS

The present application claims priority under 35 U.S.C. § 120 as a divisional application to U.S. patent application Ser. No. 15/867,632 entitled, "SYSTEM AND METHOD FOR BLOOD TYPING USING PPG TECHNOLOGY," filed Jan. 10, 2018 and hereby expressly incorporated by reference herein.

The present application claims priority under 35 U.S.C. § 119(e) to U.S. Provisional Application No. 62/613,388 entitled, "SYSTEM AND METHOD FOR INFECTION DISCRIMINATION USING PPG TECHNOLOGY," filed Jan. 3, 2018, and hereby expressly incorporated by reference herein.

The present application claims priority under 35 U.S.C. § 120 as a continuation in part to U.S. patent application Ser. No. 15/859,147 entitled, "VEHICULAR HEALTH MONITORING SYSTEM AND METHOD," filed Dec. 29, 2017, and hereby expressly incorporated by reference herein.

The present application claims priority under 35 U.S.C. § 120 as a continuation in part application to U.S. patent application Ser. No. 15/811,479 entitled, "SYSTEM AND METHOD FOR A BIOSENSOR INTEGRATED IN A VEHICLE," filed Nov. 13, 2017 and hereby expressly incorporated by reference herein, which claims priority under 35 U.S.C. § 120 as a continuation in part application to U.S. patent application Ser. No. 15/490,813 entitled, "SYSTEM AND METHOD FOR HEALTH MONITORING USING A NON-INVASIVE, MULTI-BAND BIOSENSOR," filed Apr. 18, 2017 and hereby expressly incorporated by reference herein. U.S. patent application Ser. No. 15/811,479 entitled, "SYSTEM AND METHOD FOR A BIOSENSOR INTEGRATED IN A VEHICLE," filed Nov. 13, 2017, further claims priority as a continuation in part application to U.S. patent application Ser. No. 15/489,391 entitled, "SYSTEM AND METHOD FOR A BIOSENSOR MONITORING AND TRACKING BAND," filed Apr. 17, 2017, and issued as U.S. Pat. No. 9,974,451 on May 22, 2018, and hereby expressly incorporated by reference herein.

The present application claims priority under 35 U.S.C. § 120 as a continuation in part application to U.S. patent application Ser. No. 15/485,816 entitled, "SYSTEM AND METHOD FOR A DRUG DELIVERY AND BIOSENSOR PATCH," filed Apr. 12, 2017 and hereby expressly incorporated by reference herein.

The present application claims priority under 35 U.S.C. § 120 as a continuation in part application to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017 and hereby expressly incorporated by reference herein.

The present application claims priority under 35 U.S.C. § 120 as a continuation in part application to U.S. patent application Ser. No. 15/804,581 entitled, "SYSTEM AND METHOD FOR HEALTH MONITORING INCLUDING A USER DEVICE AND BIOSENSOR," filed Nov. 6, 2017 and hereby expressly incorporated by reference herein.

The present application claims priority under 35 U.S.C. § 120 as a continuation in part application to U.S. patent application Ser. No. 15/462,700 entitled, "SYSTEM AND METHOD FOR ATOMIZING AND MONITORING A DRUG CARTRIDGE DURING INHALATION which claims priority under 35 U.S.C. § 119(e) to U.S. Provisional Application No. 62/457,138 entitled, "SYSTEM AND METHOD FOR ATOMIZING AND MONITORING A DRUG CARTRIDGE DURING INHALATION TREATMENTS," filed Feb. 9, 2017, and hereby expressly incorporated by reference herein.

The present application claims priority under 35 U.S.C. § 120 as a continuation in part application to U.S. Utility application Ser. No. 15/958,620 entitled, "SYSTEM AND METHOD FOR DETECTING A SEPSIS CONDITION," filed Apr. 20, 2018, which is hereby expressly incorporated by reference herein.

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein.

FIELD

This application relates to systems and methods of non-invasive health monitoring, and in particular to systems and methods for non-invasively detecting a blood type using PPG technology.

BACKGROUND

A person's vitals, such as temperature, blood oxygen levels, respiration rate, relative blood pressure, etc., may need to be monitored periodically typically using one or more instruments. For example, instruments for obtaining vitals of a user include blood pressure cuffs, thermometers, $SpO_2$ measurement devices, glucose level meters, etc. Often, multiple instruments must be used to obtain vitals of a person. This monitoring process is time consuming, inconvenient and is not always continuous.

In addition, detection of substances and measurement of concentration level or indicators of various substances in a user's blood stream is important in health monitoring. Currently, detection of concentration levels of blood substances is performed by drawing blood from a blood vessel using a needle and syringe. The blood sample is then transported to a lab for analysis. This type of monitoring is invasive, non-continuous and time consuming.

Furthermore, detection of a patient's blood type (also known as blood group) is vital prior to a safe blood transfusion. Determination of blood groups is a vital factor for overall healthcare needs. The human race by nature has one of a plurality of blood groups, e.g. such as A, B, AB and O. During blood transfusion any mismatch can lead to great harm or possible the death of a person. Hence it is very important to identify the blood group of a person or animal.

The blood type notations (e.g., A, B, AB, O) indicate the antigens present on the surface of red blood cells. For example, the ABO and Rh factor indicate different types of antigens on the surface of red blood cells. Current blood typing procedures include drawing a blood sample and testing the blood sample using different reagents. For example, three separate tests are performed using different reagents with either A, B or Rh antibodies. The reagents attach to the antigens on the patient's red blood cells. The blood will agglutinate when the antigens in the patient's blood match the antibodies in the test tube. The blood type may thus be discerned. However, these known blood typing procedures require drawing blood from a blood vessel using a needle and syringe. The blood sample must then be transported to a lab for the analysis. So, this type of monitoring is invasive and time consuming, especially in an emergency situation when no lab is present.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin.

The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. Such PPG techniques are heretofore been limited to determining oxygen saturation.

As such, there is a need for a continuous and non-invasive health monitoring system and method that measures user vitals and monitors concentration levels or indicators of one or more substances in blood flow as well as determines blood type of a patient.

SUMMARY

According to a first aspect, a biosensor includes an optical sensor circuit configured to obtain a plurality of spectral responses at a plurality of wavelengths detected from skin of a user. The biosensor further includes a processing circuit configured to obtain a blood type of a user; determine a first ratio R value using a first spectral response and a second spectral response of the plurality of spectral responses; access a calibration database for the blood type of the user, wherein the calibration database associates predetermined ratio R values to patient vitals for each of a plurality of blood types; and obtain a patient vital of the user using the first ratio R value, the calibration database and the blood type of the user.

According to second aspect, a device includes an optical sensor circuit configured to obtain at least one spectral response at one or more wavelengths detected from skin of a user, and a memory device configured for storing correlations between measurement values and a patient vital for each of a plurality of blood types. The device includes a processing circuit configured to obtain a blood type of the user; determine a measurement value using the at least one spectral response; and access the memory device to obtain a correlation between the measurement value and the patient vital for the blood type of the user.

According to a third aspect, a pulse oximeter includes an optical sensor circuit configured to obtain a plurality of spectral responses at a plurality of wavelengths detected from skin of a user, and a memory device configured to store oxygen saturation levels and associated measurement values for a plurality of blood types. The device includes a processing circuit configured to obtain a blood type of a user; determine a first measurement value using one or more of the plurality of spectral responses detected from skin of the user; and accessing the memory device and using the first measurement value and the blood type of the user to determine an oxygen saturation level for the user.

In one or more of the above aspects, the patient vital includes at least one of: oxygen saturation ($SpO_2$), a concentration level of nitric oxide (NO), a concentration level of a liver enzyme, a concentration level of glucose, a concentration level of an electrolyte, a concentration of one or more species of hemoglobin, or a concentration level of another substance in a blood flow of the user.

In one or more of the above aspects, the calibration database includes a plurality of $SpO_2$ calibrations, wherein each of the plurality of $SpO_2$ calibrations associates a predetermined ratio R value to an oxygen saturation level for a different one of a plurality of blood types.

In one or more of the above aspects, the processing circuit is further configured to determine an absorption spectra shift using a third spectral response and a fourth spectral response of the plurality of spectral responses; access the calibration database, wherein the calibration database includes a plurality of calibrations that associate the absorption spectra shift to the patient vital for the plurality of specific blood types; and obtain the patient vital of the user using the absorption spectra shift, the calibration database and the blood type of the user.

In one or more of the above aspects, the processing circuit is configured to obtain the blood type of the user by one or more of receiving a user input including the blood type of the user; accessing a memory device, wherein the memory device stores the blood type of the user; or identifying the blood type of the user using one or more spectral responses of the plurality of spectral responses detected by the PPG circuit.

In one or more of the above aspects, the optical sensor circuit is configured to obtain the plurality of spectral responses at the plurality of wavelengths detected from skin of the user by at least one of detecting reflected light from skin of the user or detecting transmissive light from skin of the user.

BRIEF DESCRIPTION OF THE DRAWINGS

FIG. 32 illustrates a schematic graph of an error value of example $R_{660/940}$ values for patients with various blood types at an $SpO_2$ of 97%.

FIG. 33 illustrates a logical flow diagram of an embodiment of a method for determining a calibration curve of $SpO_2$ for a blood type.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all the specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview of Blood Typing Using PPG Technology

A biosensor identifies a blood type using photoplethysmography (PPG) technology. A PPG circuit obtains a plurality of spectral responses at a plurality of wavelengths that are detected from skin of a user. A processing circuit determines a blood factor indicator using the plurality of spectral responses. The blood factor indicator may include a signal quality parameter of the PPG signal or a ratio R value. A calibration database includes a correlation of the blood factor indicator to a plurality of blood types. The blood type of the user is identified using the blood factor indicator and the calibration database.

Embodiment of the Biosensor

In an embodiment, a biosensor includes an optical sensor or photoplethysmography (PPG) circuit configured to transmit light at a plurality of wavelengths directed at skin tissue of a user. The user may include any living organism, human or non-human. The PPG circuit detects the light reflected from the skin tissue and generates one or more spectral responses at the plurality of wavelengths. A processing circuit integrated in the biosensor or in communication with the biosensor processes the spectral data to obtain a user's vitals and/or other health information. For example, a PPG signal reflects the pulsatile volume changes in the arterial or venous blood flow due to the effects of the cardiac cycle and respiratory systems on the circulation.

Figure 1:
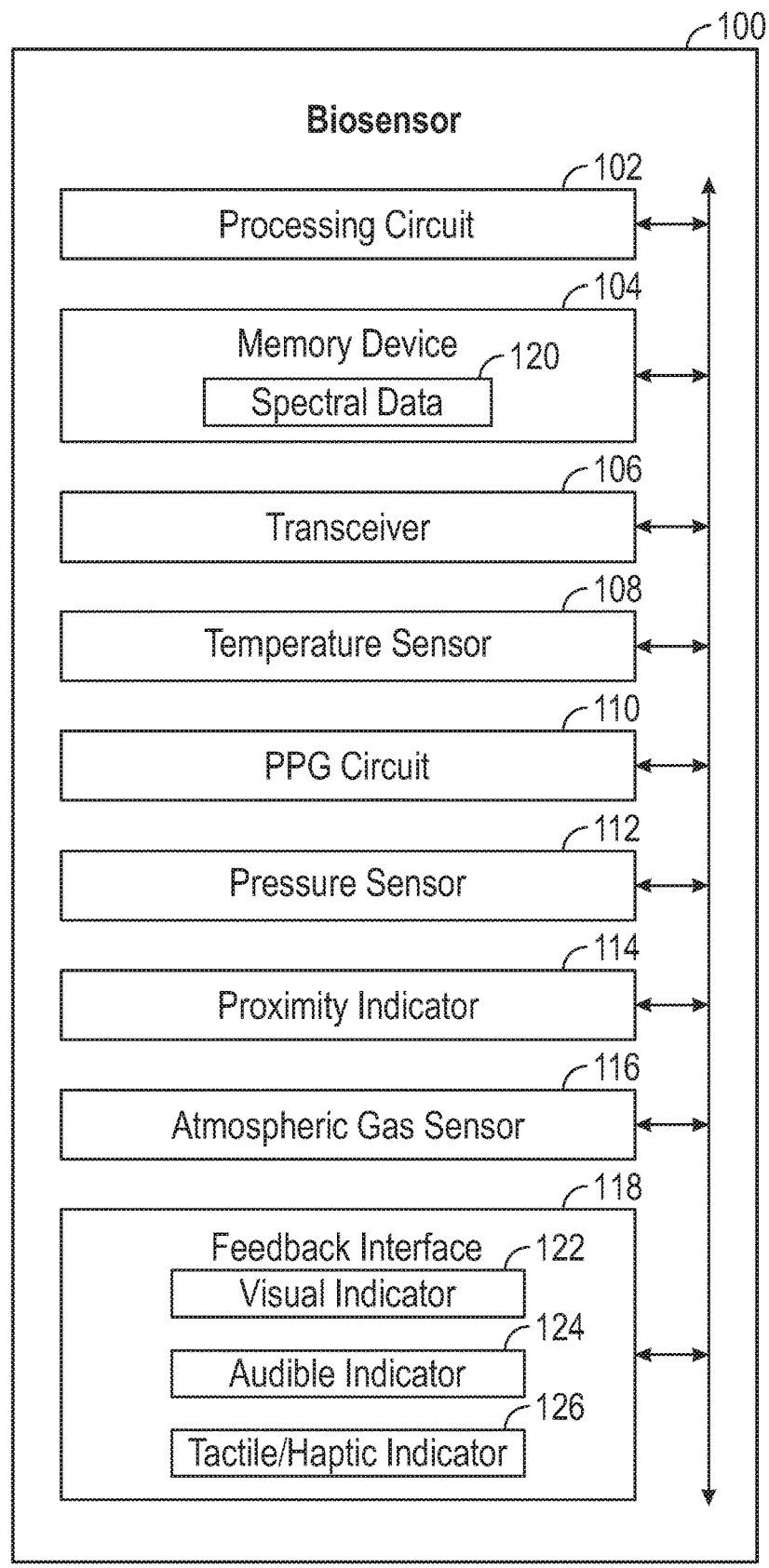
FIG. 1 illustrates a schematic block diagram of exemplary components in an embodiment of the biosensor.

FIG. 1 illustrates a schematic block diagram of exemplary components in an embodiment of the biosensor 100. The biosensor 100 includes a PPG circuit 110 as described in more detail herein. The PPG circuit 110 may be configured to detect oxygen saturation (SaO2 or SpO2) levels in blood flow, as well as heart rate and respiration rate. In addition, the PPG circuit 110 is configured to detect concentration levels of one or more substances in blood flow of a user, e.g., using one or more measurement techniques as described in more detail herein.

The biosensor 100 may include one or more processing circuits 202 communicatively coupled to a memory device 204. In one aspect, the memory device 204 may include one or more non-transitory processor readable memories that store instructions which when executed by the one or more processing circuits 102, causes the one or more processing circuits 102 to perform one or more functions described herein. The processing circuit 102 may be co-located with one or more of the other circuits of the biosensor 100 in a same physical circuit board or located separately in a different circuit board or encasement. The processing circuit may also be communicatively coupled to a central control module integrated in a vehicle as described further herein. The biosensor 100 may be battery operated and include a battery 210, such as a lithium ion battery. The memory device may store spectral data 120 or other health information or data obtained by the biosensor 100.

The biosensor 100 may include a temperature sensor 108 configured to detect a temperature of a user. For example, the temperature sensor 108 may include an array of sensors (e.g., 16×16 pixels) to detect a temperature of skin tissue of a user. The temperature sensor 214 may also be used to calibrate the PPG circuit 110.

The biosensor 100 may also include a touch pad or touch point with a proximity indicator 114 and pressure sensor 112. The proximity indicator 114 includes one or more LEDs, e.g. in the IR range, that emit pulses of light. When a finger or other body part is positioned near the touch point, a photodiode may then detect a reflectance of the IR light. The biosensor 100 may then activate the PPG circuit 110. A pressure sensor 112 may detect a pressure on the touch point by a finger or other body part and provide a feedback indicator. The feedback indicator provides a visible, audible or tactile indication that the pressure applied by the finger is within tolerance levels or needs to increase or decrease for proper detection of spectral data by the biosensor 100.

The biosensor 100 may also include an atmospheric gas sensor 116 configured to detect one or more types of gases in the interior of a vehicle. For example, the gas sensor 116 may detect carbon monoxide, carbon dioxide, nitrogen dioxide, sulfur dioxide, or other gases that may be harmful to a user and present in the air in an interior of a vehicle. The vehicular monitoring system may then provide a feedback or indicator when such harmful gases are detected over a predetermined threshold that may be harmful or affect a user.

The biosensor 100 also includes a feedback interface 118 configured to initiate a visual indicator 122, audible indicator 124 or tactile or haptic indicator 126.

The biosensor 100 further includes a transceiver 106. The transceiver 106 may include a wireless or wired transceiver configured to communicate with or with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 106 may also include a wired transceiver interface, e.g., a USB port or other type of wired connection, for communication with one or more other devices over a LAN, MAN and/or WAN. The transceiver 106 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol.

The biosensor 100 may be configured in various form factors, such as a skin patch, ear piece, watch, finger attachment, in a button, etc. The biosensor 100 may be configured for measurement of biosensor data on various skin surfaces of a patient, including on a forehead, arm, wrist, abdominal area, chest, leg, ear lobe, finger, toe, ear canal, etc. The biosensor 100 may be implemented in user equipment (UE) or user device, such as a smart phone, tablet, watch, laptop, or other type of portable user device. In addition, one or more biosensors 100 in one or more form factors may be used in combination with a user device to determine biosensor data at one or more areas of the body. For example, the biosensor 100 may communicate with a user device over a short range wired or wireless connection.

In an embodiment, the integrated or external biosensor 100 may include a pulse oximeter configured to detect pulse and blood oxygen levels. The integrated or external biosensor 100 may also include a temperature sensor to detect body or skin temperature. In an embodiment, the integrated or external biosensor 100 includes the PPG circuit 110 configured to detect one or more substances in blood, such as an indicator of glucose levels in arterial blood flow or blood levels of other substances, such as electrolytes, nitric oxide (NO), bilirubin, sodium, potassium, glucose, or blood alcohol levels.

Embodiment—PPG Circuit

Figure 2:
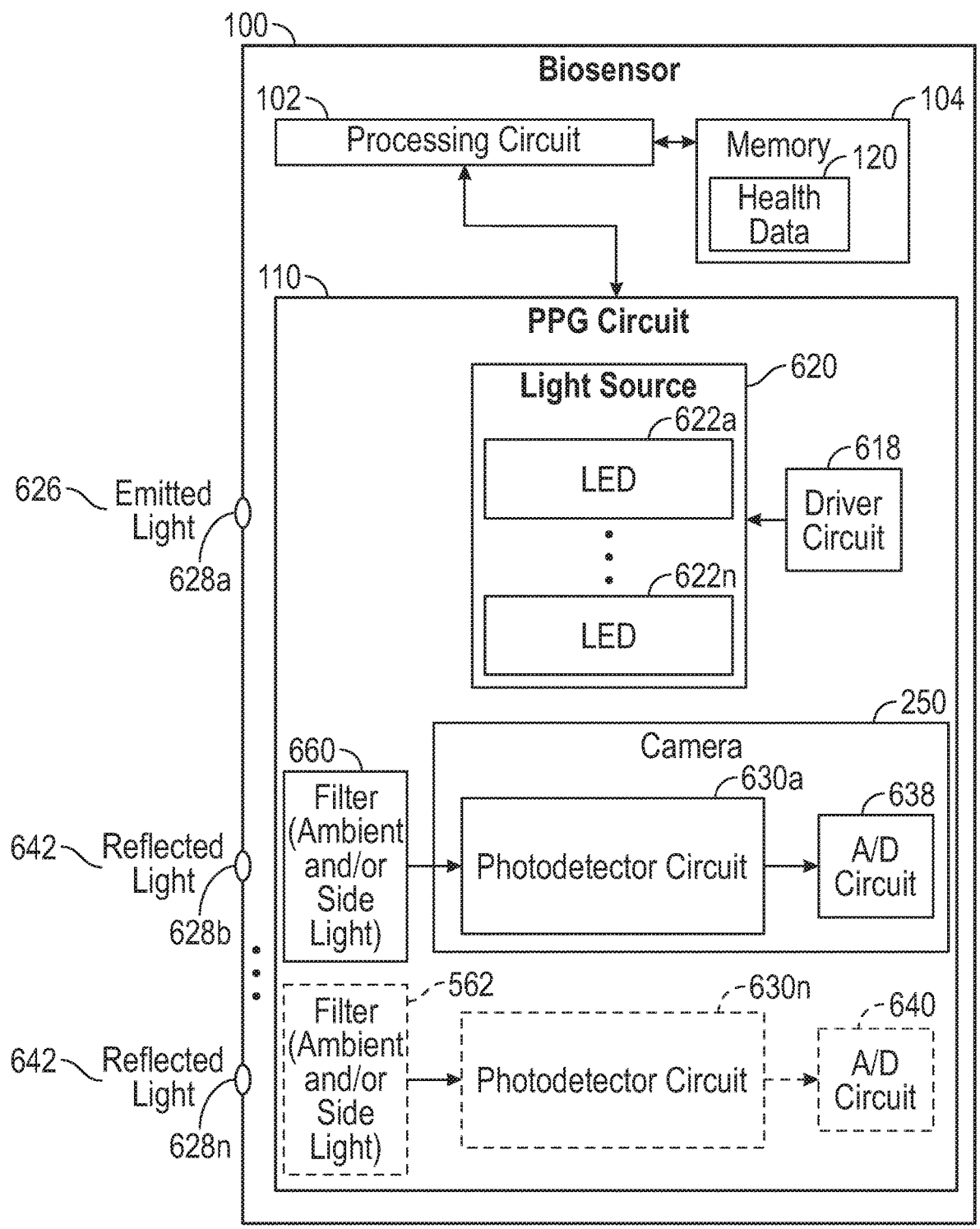
FIG. 2 illustrates a schematic block diagram of an embodiment of the PPG circuit in more detail.

FIG. 2 illustrates a schematic block diagram of an embodiment of the PPG circuit 110 in more detail. The PPG circuit 110 includes a light source 620 configured to emit a plurality of wavelengths of light across various spectrums. The light source 620 may be implemented as part of a camera 250.

In an embodiment, the light source 620 mat include a plurality of LEDs 622*a-n*. The PPG circuit 110 is configured to direct the emitted light at an outer or epidermal layer of skin tissue of a user through at least one aperture 628*a*. The plurality of LEDs 622*a-n* are configured to emit light in one or more spectrums, including infrared (IR) light, ultraviolet (UV) light, near IR light or visible light, in response to driver circuit 618. For example, the biosensor 100 may include a first LED 622*a* that emits visible light and a second LED 622*b* that emits infrared light and a third LED 622*c* that emits UV light, etc. In another embodiment, one or more of the LEDs 622*a-n* may include tunable LEDs or lasers operable to emit light over one or more frequencies or ranges of frequencies or spectrums in response to driver circuit 618. The light source 620 may be implemented as part of a camera as well.

In an embodiment, the driver circuit 618 is configured to control the one or more LEDs 622*a-n* to generate light at one or more frequencies for predetermined periods of time. The driver circuit 618 may control the LEDs 622*a-n* to operate concurrently or consecutively. The driver circuit 618 is configured to control a power level, emission period and frequency of emission of the LEDs 622*a-n*. The biosensor 100 is thus configured to emit one or more wavelengths of light in one or more spectrums that is directed at the surface or epidermal layer of the skin tissue of a user.

The PPG circuit 110 further includes one or more photodetector circuits 630*a-n*. The photodetector circuits 630 may be implemented as part of a camera 250. For example, a first photodetector circuit 630 may be configured to detect visible light and the second photodetector circuit 630 may be configured to detect IR light. Alternatively, one or more of the photodetector circuits 630*a-n* may be configured to detect light across multiple spectrums. When multiple photodetector circuits 630 are implemented, the detected signals obtained from each of the photodetector circuits 630*a-n* may be added or averaged. The first photodetector circuit 630 and the second photodetector circuit 630 may also include a first filter 660 and a second filter 662 configured to filter ambient light and/or scattered light. For example, in some embodiments, only light reflected at an approximately perpendicular angle to the skin surface of the user is desired to pass through the filters. The first photodetector circuit 630 and the second photodetector circuit 632 are coupled to a first A/D circuit 638 and a second A/D circuit 640. Alternatively, a single A/D circuit may be coupled to each of the photodetector circuits 630*a-n*. Though the PPG circuit 110 is configured to detect reflected light, the PPG circuit 110 may also be configured for transmissive light detection as well.

In another embodiment, a single photodetector circuit 630 may be implemented operable to detect light over multiple spectrums or frequency ranges. The one or more photodetector circuits 630 include one or more types of spectrometers or photodiodes or other type of circuit configured to detect an intensity of light as a function of wavelength to obtain a spectral response. In use, the one or more photodetector circuits 630 detect the intensity of light reflected from skin tissue of a user that enters one or more apertures 628*b-n* of the biosensor 100. In another example, the one or more photodetector circuits 630 detect the intensity of light due to transmissive absorption (e.g., light transmitted through tissues such as a fingertip or ear lobe). The one or more photodetector circuits 630*a-n* then obtain a spectral response of the reflected or transmissive light by measuring an intensity of the light at one or more wavelengths.

In another embodiment, the light source 620 may include a broad spectrum light source, such as a white light to infrared (IR) or near IR LED 622, that emits light with wavelengths across multiple spectrums, e.g. from 350 nm to 2500 nm. Broad spectrum light sources 620 with different ranges may be implemented. In an aspect, a broad spectrum light source 620 is implemented with a range across 100 nm wavelengths to 2000 nm range of wavelengths in the visible, IR and/or UV frequencies. For example, a broadband tungsten light source for spectroscopy may be used. The spectral response of the reflected light is then measured across the wavelengths in the broad spectrum, e.g. from 350 nm to 2500 nm, concurrently. In an aspect, a charge coupled device (CCD) spectrometer may be configured in the photodetector circuit 630 to measure the spectral response of the detected light over the broad spectrum.

The PPG circuit 110 may also include a digital signal processing (DSP) circuit or filters or amplifiers to process the PPG signals. The spectral data may then be processed by the processing circuit 102 to obtain health data of a user. The spectral data may alternatively or in additionally be transmitted by the biosensor 100 to a central control module in a vehicle for processing to obtain health data of a user.

One or more of the embodiments of the biosensor 100 described herein is configured to detect a concentration level of one or more substances within blood flow using photoplethysmography (PPG) techniques. For example, the biosensor 100 may detect nitric oxide (NO) concentration levels and correlate the NO concentration level to a blood glucose level. The biosensor 100 may also detect oxygen saturation (SaO2 or SpO2) levels in blood flow. The biosensor may also be configured to detect a liver enzyme cytochrome oxidase (P450) enzyme and correlate the P450 concentration level to a blood alcohol level. The biosensor 100 may also detect vitals, such as heart rate and respiration rate. Because blood flow to the skin can be modulated by multiple other physiological systems, the biosensor 100 may also be used to monitor hypovolemia and other circulatory conditions.

In use, the biosensor 100 performs PPG techniques using the PPG circuit 110 to detect the concentration levels of one or more substances in blood flow. In one aspect, the biosensor 100 receives reflected light from skin tissue to obtain a spectral response. The spectral response includes a spectral curve that illustrates an intensity or power or energy at a frequency or wavelength in a spectral region of the detected light. The ratio of the resonance absorption peaks from two different frequencies can be calculated and based on the Beer-Lambert law used to obtain the levels of substances in the blood flow.

First, the spectral response of a substance or substances in the arterial blood flow is determined in a controlled environment, so that an absorption coefficient $\alpha_{g1}$ can be obtained at a first light wavelength $\lambda 1$ and at a second wavelength $\lambda_2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined. For example, the concentration Cg may be obtained from the following equations:

At the first wavelength $\lambda_1, I_1 = I_{in1} * 10^{-(\alpha_{g1}C_{gw} + \alpha_{w1}C_w) * l}$ At the first wavelength $\lambda_2, I_2 = I_{in2} * 10^{-(\alpha_{g2}C_{gw} + \alpha_{w2}C_w) * l}$ wherein:

$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I1}{Iin1}\right)}{\log 10\left(\frac{I2}{Iin2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2}) * R - (\alpha_{w1} - \alpha_{gw1})}$$

The biosensor 100 may thus determine the concentration of various substances in arterial blood flow from the Beer-Lambert principles using the spectral responses of at least two different wavelengths.

Figure 3:
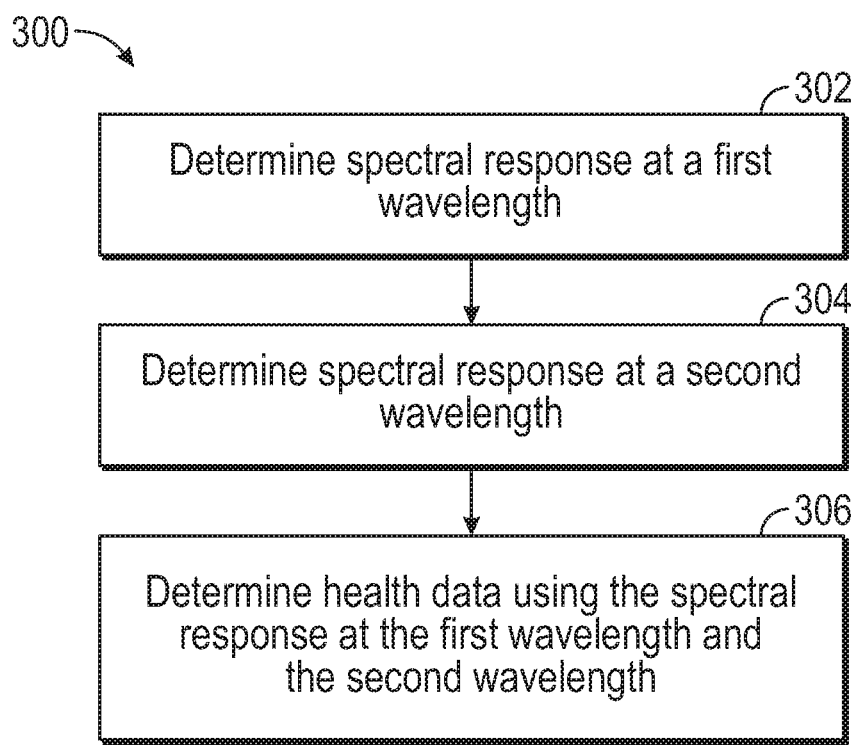
FIG. 3 illustrates a logical flow diagram of an embodiment of a method for determining concentration level of a substance in blood flow using Beer-Lambert principles.

FIG. 3 illustrates a logical flow diagram of an embodiment of a method 300 for determining concentration level of a substance in blood flow using Beer-Lambert principles. The biosensor 100 transmits light at a first predetermined wavelength and at a second predetermined wavelength. The biosensor 100 detects the light (reflected from the skin or transmitted through the skin) and determines the spectral response at the first wavelength at 302 and at the second wavelength at 304. The biosensor 100 then determines an indicator or concentration level of the substance using the spectral responses of the first and second wavelength at 306. In general, the first predetermined wavelength is selected that has a high absorption coefficient for the substance in blood flow while the second predetermined wavelength is selected that has a lower absorption coefficient for the substance in blood flow. Thus, it is generally desired that the spectral response for the first predetermined wavelength have a higher intensity level in response to the substance than the spectral response for the second predetermined wavelength.

In an embodiment, the biosensor 100 may detect a concentration level of NO in blood flow using a first predetermined wavelength in a range of 380-410 nm and in particular at 390 nm or 395 nm. In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 302 and 304. The biosensor 100 analyzes the first and second spectral responses to detect an indicator or concentration level of NO in the arterial blood flow at 306.

Figure 4A:
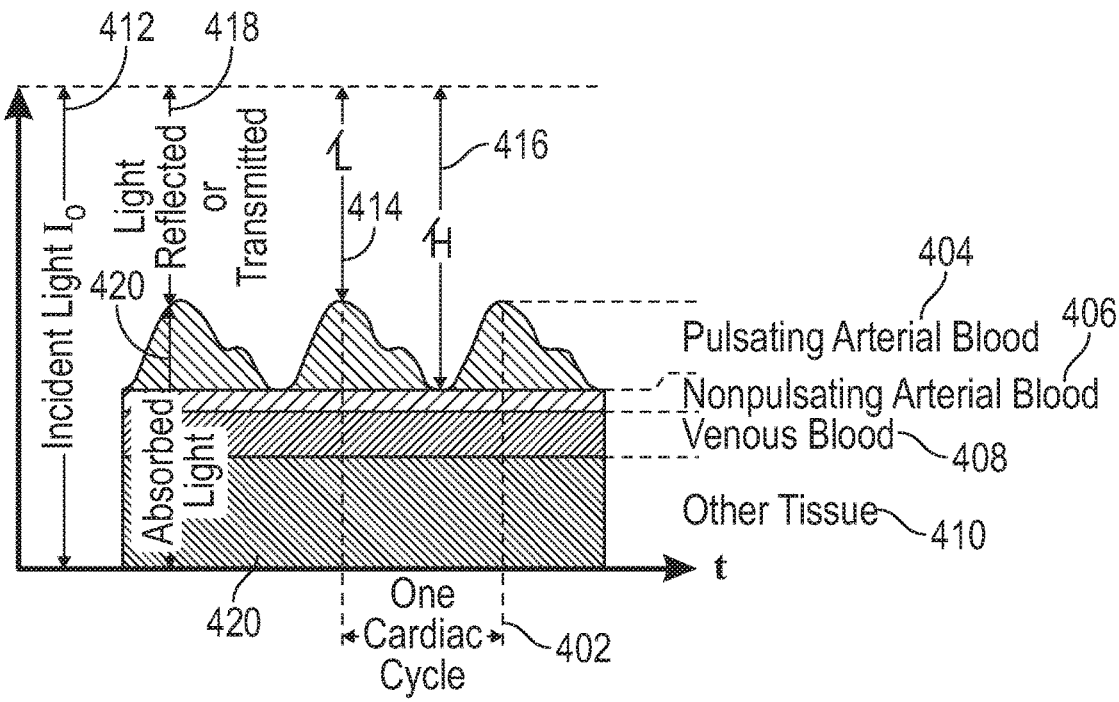
FIG. 4A illustrates a schematic block diagrams of an embodiment of a method for photoplethysmography (PPG) techniques in more detail.
Figure 4B:
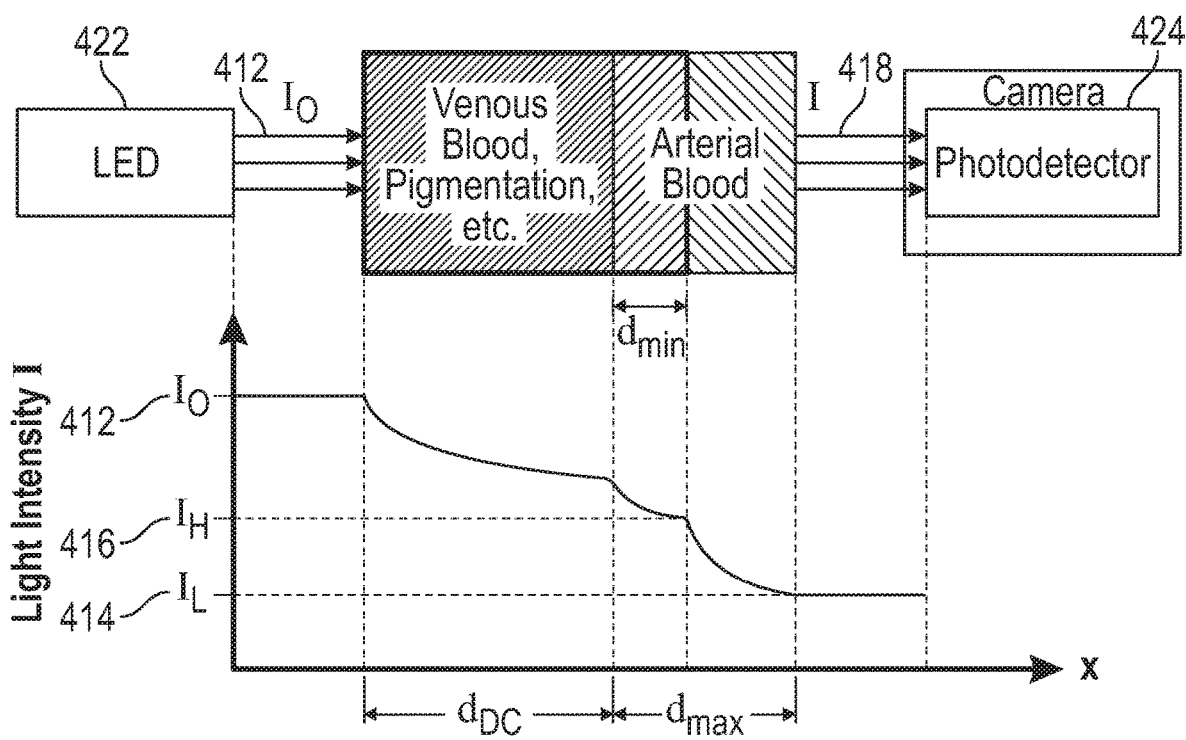
FIG. 4B illustrates another schematic block diagram of an embodiment of a method for photoplethysmography (PPG) techniques in more detail.

FIG. 4A and FIG. 4B illustrate schematic block diagrams of an embodiment of a method for photoplethysmography (PPG) techniques in more detail. Photoplethysmography (PPG) is used to measure time-dependent volumetric properties of blood in blood vessels due to the cardiac cycle. For example, the heartbeat affects the volume of arterial blood flow and the concentration or absorption levels of substances being measured in the arterial blood flow. As shown in FIG. 4A, over a cardiac cycle 402, pulsating arterial blood 404 changes the volume of blood flow in an artery.

Incident light $I_O$ 412 is directed at a tissue site and a certain amount of light is reflected or transmitted 418 and a certain amount of light is absorbed 420. At a peak of arterial blood flow or arterial volume, the reflected/transmitted light $I_L$ 414 is at a minimum due to absorption by the venous blood 408, nonpulsating arterial blood 406, pulsating arterial blood 404, other tissue 410, etc. At a minimum of arterial blood flow or arterial volume during the cardiac cycle, the transmitted/reflected light $I_H$ 416 is at a maximum due to lack of absorption from the pulsating arterial blood 404.

The biosensor 100 is configured to filter the reflected/transmitted light $I_L$ 414 of the pulsating arterial blood 404 from the transmitted/reflected light $I_H$ 416. This filtering isolates the light due to reflection/transmission of substances in the pulsating arterial blood 404 from the light due to reflection/transmission from venous (or capillary) blood 408, other tissues 410, etc. The biosensor 100 may then measure the concentration levels of one or more substances from the reflected/transmitted light $I_L$ 814 in the pulsating arterial blood flow 404.

For example, as shown in FIG. 4B, incident light $I_O$ 412 is directed at a tissue site by an LED 422 at one or more wavelengths. The reflected/transmitted light I 418 is detected by photodetector 424 or camera 250. At a peak of arterial blood flow or arterial volume, the reflected light $I_L$ 414 is at a minimum due to absorption by venous blood 808, non-pulsating arterial blood 406, pulsating arterial blood 404, other tissue 410, etc. At a minimum of arterial blood flow or arterial volume during the cardiac cycle, the Incident or reflected light $I_H$ 416 is at a maximum due to lack of absorption from the pulsating arterial blood 404. Since the light I 418 is reflected or traverses through a different volume of blood at the two measurement times, the measurement provided by a PPG sensor is said to be a 'volumetric measurement' descriptive of the differential volumes of blood present at a certain location within the user's arteriolar bed at different times. Though the above has been described with respect to arterial blood flow, the same principles described herein may be applied to venous blood flow.

In general, the relative magnitudes of the AC and DC contributions to the reflected/transmitted light signal I 418 may be used to substantially determine the differences between the diastolic points and the systolic points. In this case, the difference between the reflected light $I_L$ 414 and reflected light $I_H$ 416 corresponds to the AC contribution of the reflected light 418 (e.g. due to the pulsating arterial blood flow). A difference function may thus be computed to determine the relative magnitudes of the AC and DC components of the reflected light I 418 to determine the magnitude of the reflected light $I_L$ 414 due to the pulsating arterial blood 404. The described techniques herein for determining the relative magnitudes of the AC and DC contributions is not intended as limiting. It will be appreciated that other methods may be employed to isolate or otherwise determine the relative magnitude of the light $I_L$ 414 due to pulsating arterial blood flow.

Figure 5:
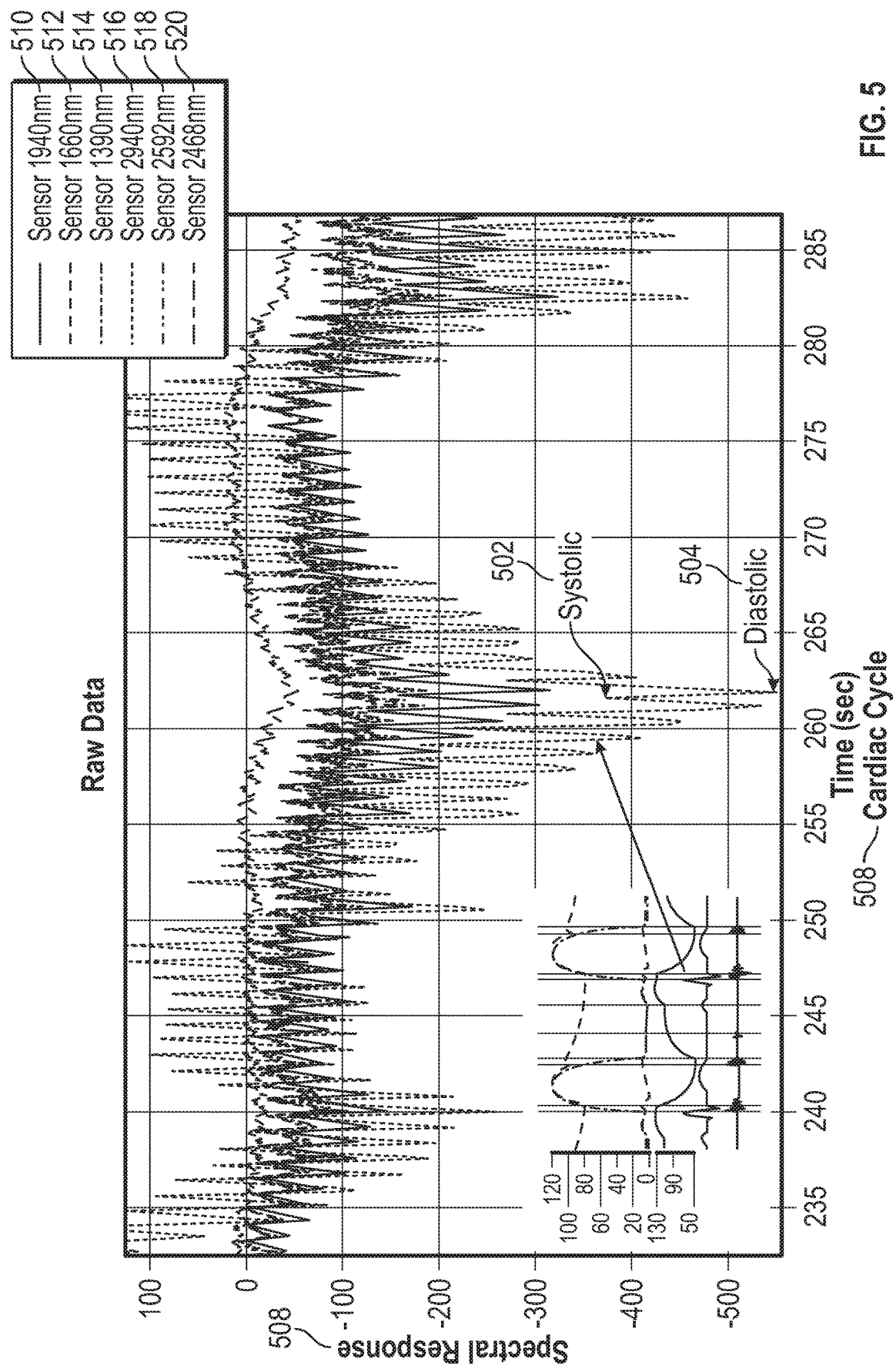
FIG. 5 illustrates a schematic diagram of a graph of actual clinical data obtained using an embodiment of the biosensor and PPG techniques at a plurality of wavelengths.

FIG. 5 illustrates a schematic diagram of a graph of actual clinical data obtained using an embodiment of the biosensor 100 and PPG techniques at a plurality of wavelengths. In one aspect, the biosensor 100 is configured to emit light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral responses 508 for the plurality of wavelengths obtained using an embodiment of the biosensor in clinical trials is shown in FIG. 5. In this clinical trial, two biosensors 100 attached to two separate fingertips of a user were used to obtain the spectral responses 508. The first biosensor 100 obtained the spectral response for a wavelength at 940 nm 510, a wavelength at 660 nm 512 and a wavelength at 390 nm 514. The second biosensor 100 obtained the spectral response for a wavelength at 940 nm 516, a wavelength at 592 nm 518 and a wavelength at 468 nm 520.

In one aspect, the spectral response obtained at each wavelength may be aligned based on the systolic 502 and diastolic 504 points in their respective spectral responses. This alignment is useful to associate each spectral response with a particular stage or phase of the pulse-induced local pressure wave within the blood vessel (which may mimic the cardiac cycle 506 and thus include systolic and diastolic stages and sub-stages thereof). This temporal alignment helps to determine the absorption measurements acquired near a systolic point in time of the cardiac cycle and near the diastolic point in time of the cardiac cycle 506 associated with the local pressure wave within the user's blood vessels. This measured local pulse timing information may be useful for properly interpreting the absorption measurements in order to determine the relative contributions of the AC and DC components measured by the biosensor 100. So, for one or more wavelengths, the systolic points 502 and diastolic points 504 in the spectral response are determined. These systolic points 502 and diastolic points 504 for the one or more wavelengths may then be aligned as a method to discern concurrent responses across the one or more wavelengths.

In another embodiment, the systolic points 502 and diastolic points 504 in the absorbance measurements are temporally correlated to the pulse-driven pressure wave within the arterial blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 5 illustrates the spectral response obtained at the plurality of wavelengths with the systolic points 502 and diastolic points 504 aligned.

Figure 6:
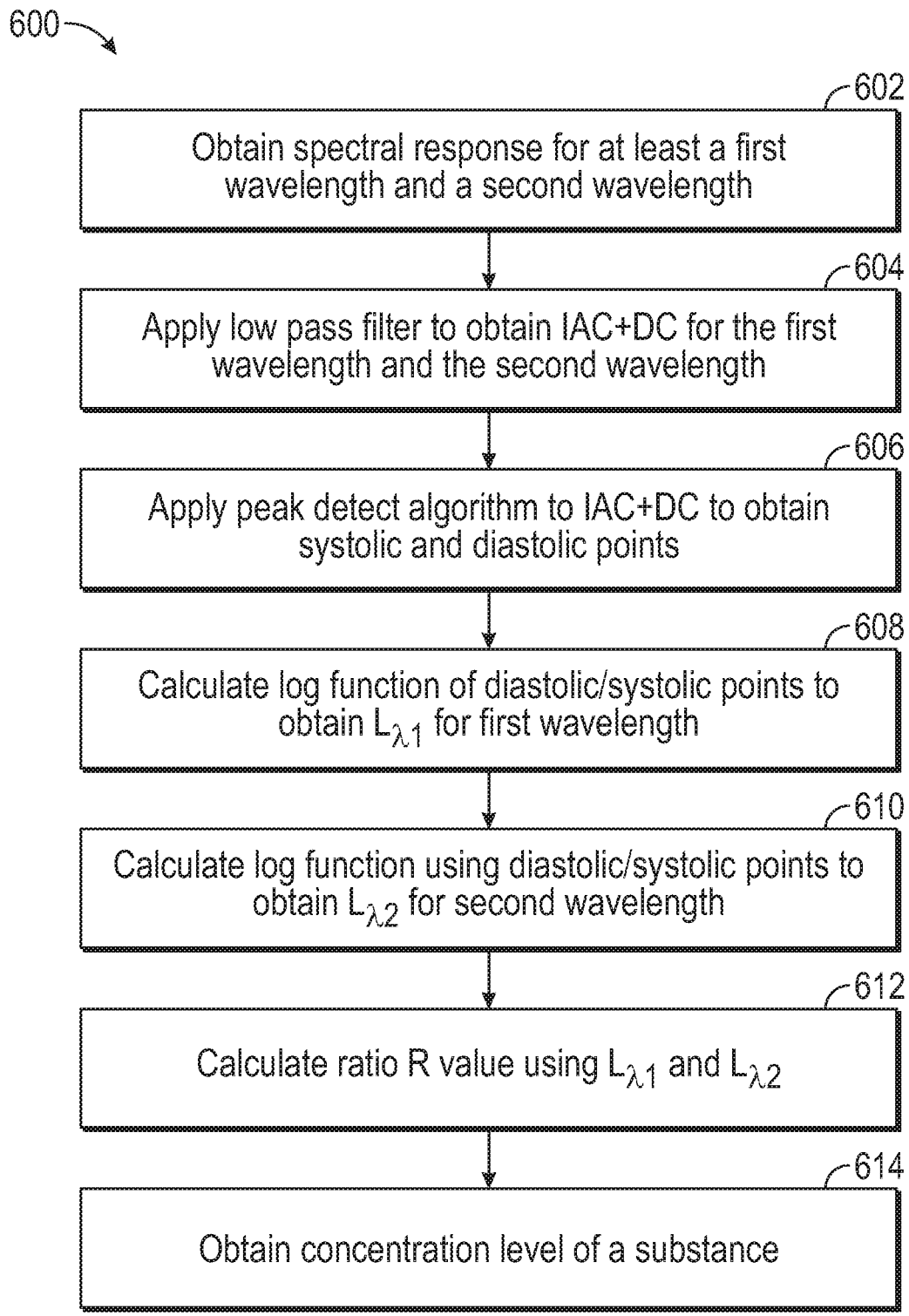
FIG. 6 illustrates a logical flow diagram of an embodiment of a method of the biosensor.

FIG. 6 illustrates a logical flow diagram of an embodiment of a method 600 of the biosensor 100. In one aspect, the biosensor 100 emits and detects light at a plurality of predetermined frequencies or wavelengths, such as approximately 940 nm, 660 nm, 390 nm, 592 nm, and 468 nm or in ranges thereof. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the user in a range of 360 nm to 410 nm including the predetermined wavelength 390 nm. For the predetermined wavelength of 940 nm, the biosensor 100 may transmit light directed at the skin tissue of the user in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 602. The spectral responses may be measured over a predetermined period (such as 300 usec.). This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The spectral responses are measured over one or more cardiac cycles. The spectral data obtained by the PPG circuit 110, such as the digital or analog spectral responses over the one or more cardiac cycles, may be processed locally by the biosensor 100 or transmitted to a central control module of a vehicle for processing.

The systolic and diastolic points of the spectral response are then determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined.

A low pass filter (such as a 5 Hz low pass filter) is applied to the spectral response signal at 604. The relative contributions of the AC and DC components are obtained $I_{AC+DC}$ and $I_{AC}$. A peak detection algorithm is applied to determine the systolic and diastolic points at 606. The systolic and diastolic points of the spectral response for each of the wavelengths may be aligned and may also be aligned with systolic and diastolic points of an arterial pulse waveform or cardiac cycle.

Beer Lambert equations are then applied as described herein. For example, the $L_\lambda$ values are then calculated for the first wavelength $\lambda_1$ at 608 and the second wavelength $\lambda_2$ at 610, wherein the $L_\lambda$ values for a wavelength equals:

$$L_\lambda = \text{Log}10\left(\frac{IAC+DC}{IDC}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response.

A ratio R of the $L_\lambda$ values at two wavelengths may then be determined at 612. For example, the ratio R may be obtained from the following:

$$\text{Ratio } R = \frac{L\lambda 1}{L\lambda 2}$$

The spectral responses may be measured and the $L_\lambda$ values and Ratio R determined continuously, e.g. every 1-2 seconds, and the obtained $L_\lambda$ values and/or Ratio R averaged over a predetermined time period, such as over 1-2 minutes. The concentration level of a substance may then be obtained from the R value and a calibration database at 614. The biosensor 100 may continuously monitor a user over 2-3 hours or continuously over days or weeks.

In one embodiment, the $R_{390,940}$ value with $L_{\lambda 1=390\,nm}$ and $L_{\lambda 2=940}$ may be non-invasively and quickly and easily obtained using the biosensor 100 to determine a concentration level of NO in blood flow of a user. In particular, in unexpected results, it is believed that the nitric oxide NO levels in the arterial blood flow is being measured at least in part by the biosensor 100 at wavelengths in the range of 380-410 and in particular at $\lambda_1=390$ nm. Thus, the biosensor 100 measurements to determine the $L_{390\,nm}$ values are the first time NO concentration levels in arterial blood flow have been measured directly in vivo. These and other aspects of the biosensor 100 are described in more detail herein with clinical trial results.

Figure 7:
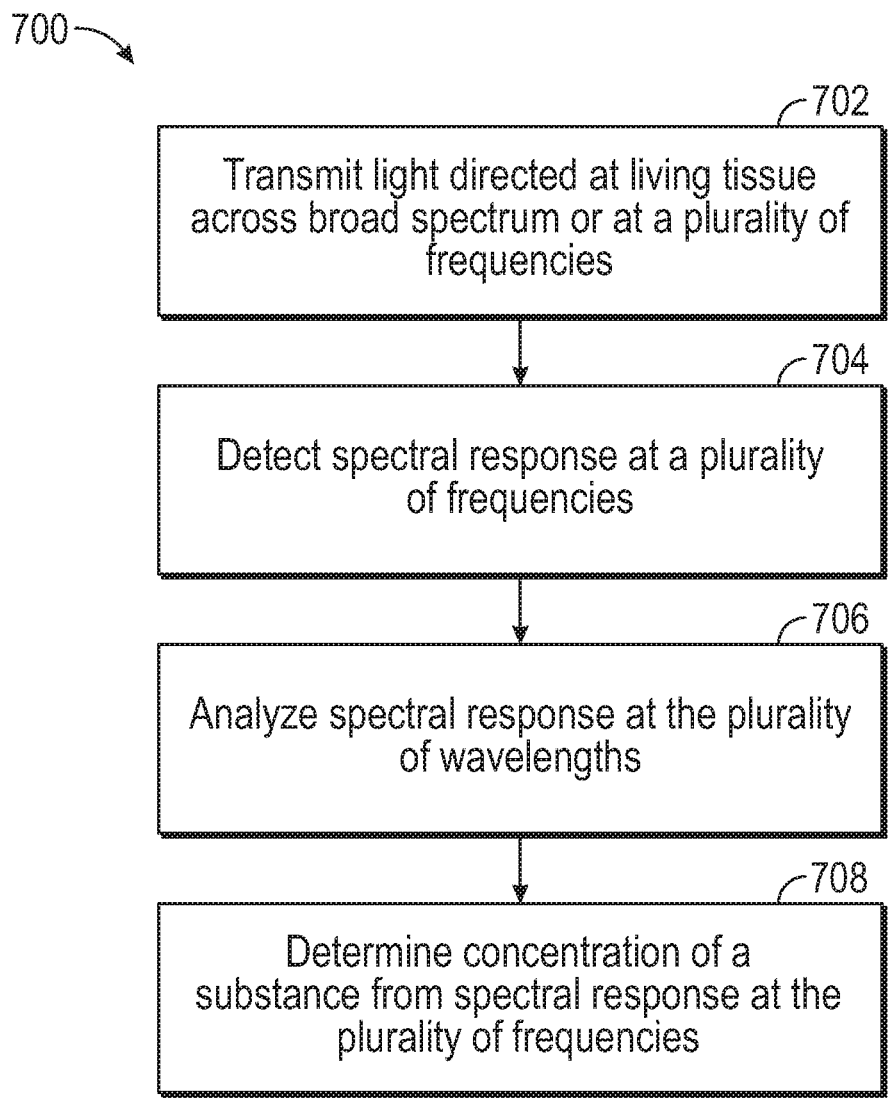
FIG. 7 illustrates a logical flow diagram of an exemplary method to determine levels of a substance in blood flow using the spectral responses at a plurality of wavelengths.

Embodiment—Determination of Concentration Level of a Substance Using Spectral Responses at a Plurality of Wavelengths FIG. 7 illustrates a logical flow diagram of an exemplary method 700 to determine levels of a substance in blood flow using the spectral responses at a plurality of wavelengths. The absorption coefficient of a substance may be sufficiently higher at a plurality of wavelengths, e.g. due to isoforms or derivative compounds. For example, the increased intensity of light at a plurality of wavelengths may be due to reflectance by isoforms or other compounds in the arterial blood flow. Another method for determining the concentration levels may then be used by measuring the spectral responses and determining L and R values at a plurality of different wavelengths of light. In this example then, the concentration level of the substance is determined using spectral responses at multiple wavelengths. An example for calculating the concentration of a substance over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ of a substance, its isoforms or other compounds including the substance are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of the substance may be isolated from the isoforms or other compounds by compensating for the concentration of the compounds. Thus, using the spectral responses at multiple frequencies provides a more robust determination of the concentration level of a substance.

In use, the biosensor 100 transmits light directed at skin tissue at a plurality of wavelengths or over a broad spectrum at 702. The spectral response of light from the skin tissue is detected at 704, and the spectral responses are analyzed at a plurality of wavelengths (and in one aspect including a range of +/−10 to 50 nm around each of the wavelengths) at 706. Then, the concentration level C of the substance may be determined using the spectral responses at the plurality of wavelengths at 708. The concentration level of the substance may be isolated from isoforms or other compounds by compensating for the concentration of the compounds.

Figure 8:
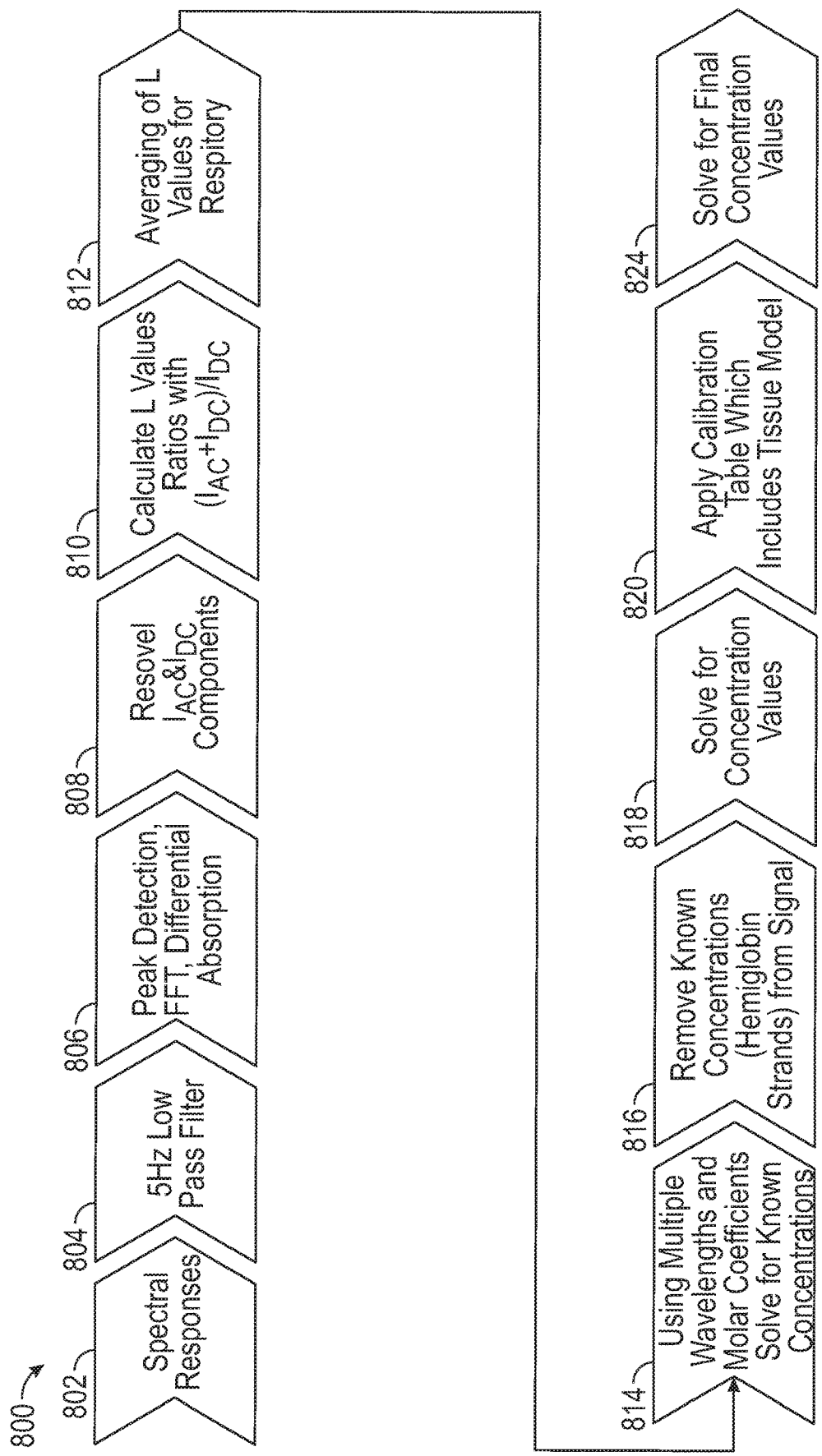
FIG. 8 illustrates a logical flow diagram of an exemplary method to determine levels of a substance using the spectral responses at a plurality of wavelengths in more detail.

FIG. 8 illustrates a logical flow diagram of an exemplary method 800 to determine levels of a substance using the spectral responses at a plurality of wavelengths in more detail. The spectral responses are obtained at 802. The spectral response signals include AC and DC components $I_{AC+DC}$. A low pass filter (such as a 5 Hz low pass filter) is applied to each of the spectral response signals $I_{AC+DC}$ to isolate the DC component of each of the spectral response signals $I_{DC}$ at 804. The AC fluctuation is due to the pulsatile expansion of the arteriolar bed due to the volume increase in arterial blood. In order to measure the AC fluctuation, measurements are taken at different times and a peak detection algorithm is used to determine the diastolic point and the systolic point of the spectral responses at 806. A Fast Fourier transform (FFT) function may also be used to isolate the DC component $I_{DC}$ of a spectral response signal $I_{AC+DC}$ at 806. The $I_{DC}$ component is thus isolated from the spectral signal at 808.

The $I_{AC+DC}$ and $I_{DC}$ components are then used to compute the L values at 810. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period) or over a plurality of cardiac cycles at 812.

In an embodiment, isoforms of a substance may be attached in the blood stream to one or more species of hemoglobin compounds. The concentration level of the hemoglobin species may then need to be accounted for to isolate the concentration level of the substance from the hemoglobin compounds. For example, nitric oxide (NO) is found in the blood stream in a gaseous form and also attached to hemoglobin compounds. Thus, the spectral responses obtained around 390 nm may include a concentration level of the hemoglobin species as well as nitric oxide. The hemoglobin concentration levels must thus be compensated for to isolate the nitric oxide NO concentration levels.

Multiple wavelengths and absorption coefficients for hemoglobin species are used to determine a concentration of one or more of the hemoglobin species at 814. Other methods may also be used to obtain a concentration level of various species of hemoglobin in the blood flow as well. The concentration of the hemoglobin species is then adjusted from the measurements at 816. The concentration values of the substance may then be obtained at 818. For example, the R values are then determined at 818.

To determine a concentration level of the substance, a calibration table or database is used that associates the obtained R value to a concentration level of the substance at 820. The calibration database correlates the R value with a concentration level. The calibration database may be generated for a specific user or may be generated from clinical data of a large sample population. For example, it is determined that the R values should correlate to similar NO concentration levels across a large sample population. Thus, the calibration database may be generated from testing of a large sample of a general population to associate R values and NO concentration levels.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and concentration levels of a substance depending on the underlying skin tissue characteristics that were measured.

The concentration level of the substance in blood flow is then obtained at 824. The concentration level may be expressed as mmol/liter, as a saturation level percentage, as a relative level on a scale, etc.

In another embodiment, in order to remove the hemoglobin concentration(s) from the original PPG signals, a mapping function may be created which is constructed through clinical data and tissue modeling. For example, known $SpO_2$ values in the infrared region and the same signals at the UV side of the spectrum are obtained. Then a linear inversion map can be constructed where the R values are input into a function and the desired concentration(s) can be determined. For example, a curve that correlates R values to concentration levels may be tabulated. A polynomial equation with multiple factors can also be used to account for different R values to represent the linear inversion map. This correlation may be derived from validated clinical data.

For example, a regression curve that correlates R values and NO concentration levels may be generated based on clinical data from a large general population. A polynomial may be derived from the curve and used to solve for an NO concentration level from the R value. The polynomial is stored in the calibration database and may be used rather than using a calibration look-up table or curve.

Embodiment—Determination of a Concentration of Hemoglobin Species

The Beer-Lambert theory may be generalized for a multi-wavelength system to determine a concentration of known hemoglobin species using the following matrix notation:

$$\begin{bmatrix} dA_{\lambda 1}^{LB} \\ \vdots \\ dA_{\lambda n}^{LB} \end{bmatrix} = \begin{bmatrix} \Delta l_{\lambda 1} & \cdots & 0 \\ \vdots & \ddots & \vdots \\ 0 & \cdots & \Delta l_{\lambda n} \end{bmatrix} \begin{bmatrix} \varepsilon_{\lambda 1, HbX_1} & \cdots & \varepsilon_{\lambda 1, HbX_m} \\ \vdots & \ddots & \vdots \\ \varepsilon_{\lambda n, HbX_1} & \cdots & \varepsilon_{\lambda n, HbX_m} \end{bmatrix} \cdot \begin{bmatrix} HbX_1 \\ \vdots \\ HbX_m \end{bmatrix} \cdot c(Hb),$$

wherein $dA_\lambda^{LB}$ is a differential absorption within the Beer-Lambert model $\varepsilon_{\lambda n1, HbX1}$ is an extinction coefficient HbX are hemoglobin fractions $\Delta l\lambda$ is the optical path-length for wavelength $\lambda$ c(Hb) is the hemoglobin concentration This Beer-Lambert matrix equation for determining concentration levels of one or more hemoglobin species may be solved when m is equal or greater than n, e.g., which means that at least four wavelengths are needed to solve for four hemoglobin species. The spectral responses at these four wavelengths may be analyzed to determine the concentration of the plurality of hemoglobin species.

Figure 9:
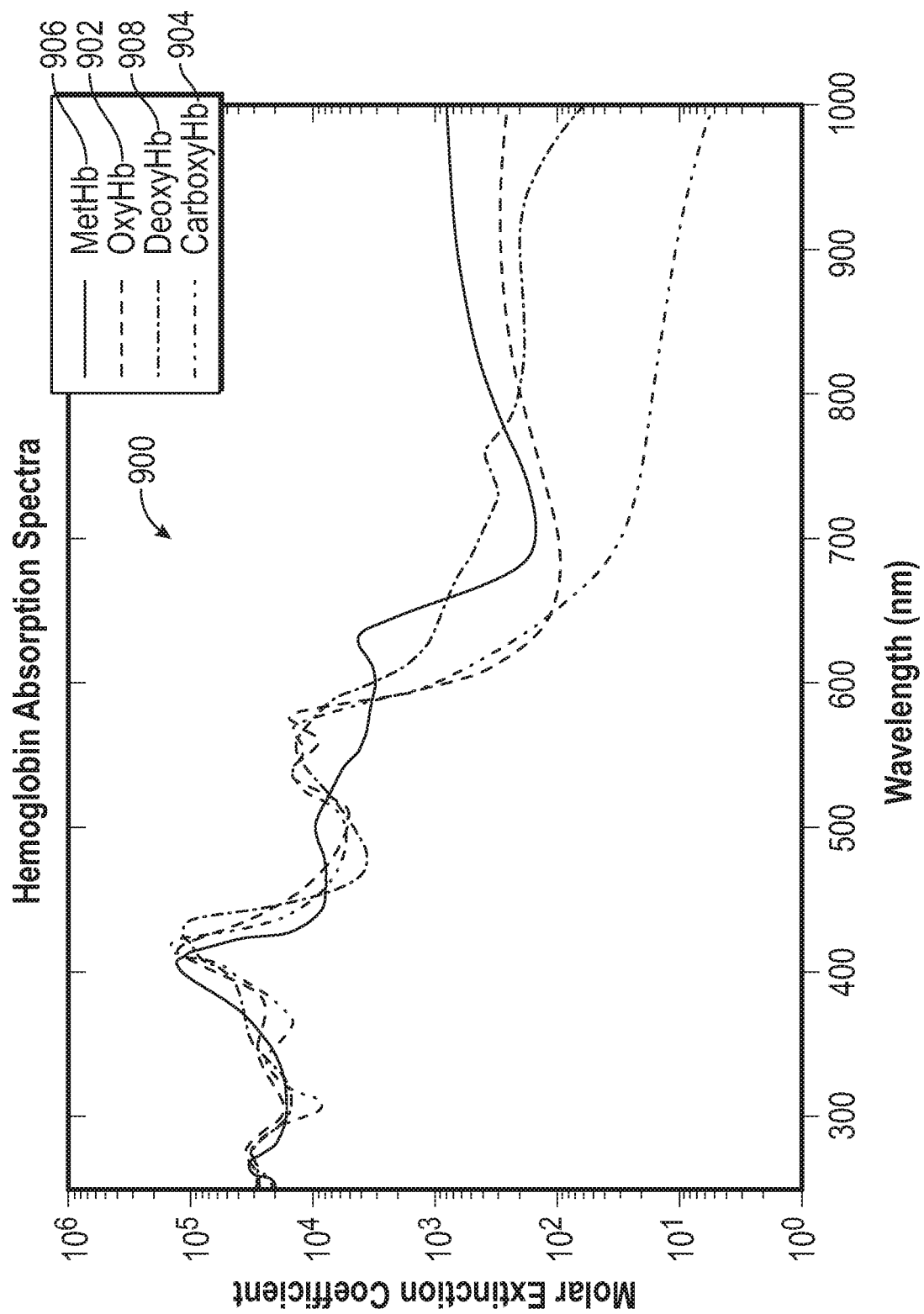
FIG. 9 illustrates a schematic block diagram of an exemplary embodiment of a graph illustrating the extinction coefficients over a range of frequencies for a plurality of hemoglobin species.

FIG. 9 illustrates a schematic block diagram of an exemplary embodiment of a graph 900 illustrating the extinction coefficients over a range of frequencies for a plurality of hemoglobin species. The hemoglobin species include, e.g., Oxyhemoglobin [$HbO_2$ or OxyHb] 902, Carboxyhemoglobin [HbCO or CarboxyHb] 904, Methemoglobin [HbMet or MetHb] 906, and deoxygenated hemoglobin (DeoxyHb or RHb) 908. A method for determining the relative concentration or composition of hemoglobin species included in blood is described in more detail in U.S. Pat. No. 6,104,938 issued on Aug. 15, 2000, which is hereby incorporated by reference herein.

A direct calibration method for calculating hemoglobin species may be implemented by the biosensor 100. Using four wavelengths and applying a direct model for four hemoglobin species in the blood, the following equation results:

$$HbX = \frac{a_1 * dA_1 + a_2 * dA_2 + a_3 * dA_3 + a_4 * dA_4}{b_1 * dA_1 + b_2 * dA_2 + b_3 * dA_3 + b_4 * dA_4}$$

wherein $dA_\lambda$ is the differential absorption signal $a_n$ and $b_n$ are calibration coefficients The calibration coefficients $a_n$ and $b_n$ may be experimentally determined over a large population average. The biosensor 100 may include a calibration database to account for variances in the calibration coefficients $a_1$ and $b_1$ (or extinction coefficients) for the hemoglobin species for various underlying tissue characteristics.

A two-stage statistical calibration and measurement method for performing PPG measurement of hemoglobin species concentrations may also be implemented by the biosensor 100. Concentrations of MetHb, $HbO_2$, RHb and HbCO are estimated by first estimating a concentration of MetHb (in a first stage) and subsequently, if the concentration of MetHb is within a predetermined range, then the estimated concentration of MetHb is assumed to be accurate and this estimated concentration of MetHb is utilized as a "known value" in determining the concentrations of the remaining analytes $HbO_2$, RHb and HbCO (in a second stage). This method for determining a concentration of hemoglobin species using a two stage calibration and analyte measurement method is described in more detail in U.S. Pat. No. 5,891,024 issued on Apr. 6, 1999, which is hereby incorporated by reference herein.

The concentration of various hemoglobin compounds may thus be determined. The biosensor 100 compensates for the hemoglobin concentration in determinations to obtain the concentration level of one or more substances in blood flow, such as NO. Though several methods are described herein for obtaining a concentration of hemoglobin species, other methods or processes may be used by the biosensor 100 to determine the concentration of hemoglobin analytes or otherwise adjusting or compensating the obtained measurements to account for a hemoglobin concentration when determining the concentration levels of NO in a blood stream.

Embodiment—Determination of Concentration Levels of a Substance Using Shifts in Absorbance Peaks In another embodiment, a concentration level of a substance may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

Figure 10:
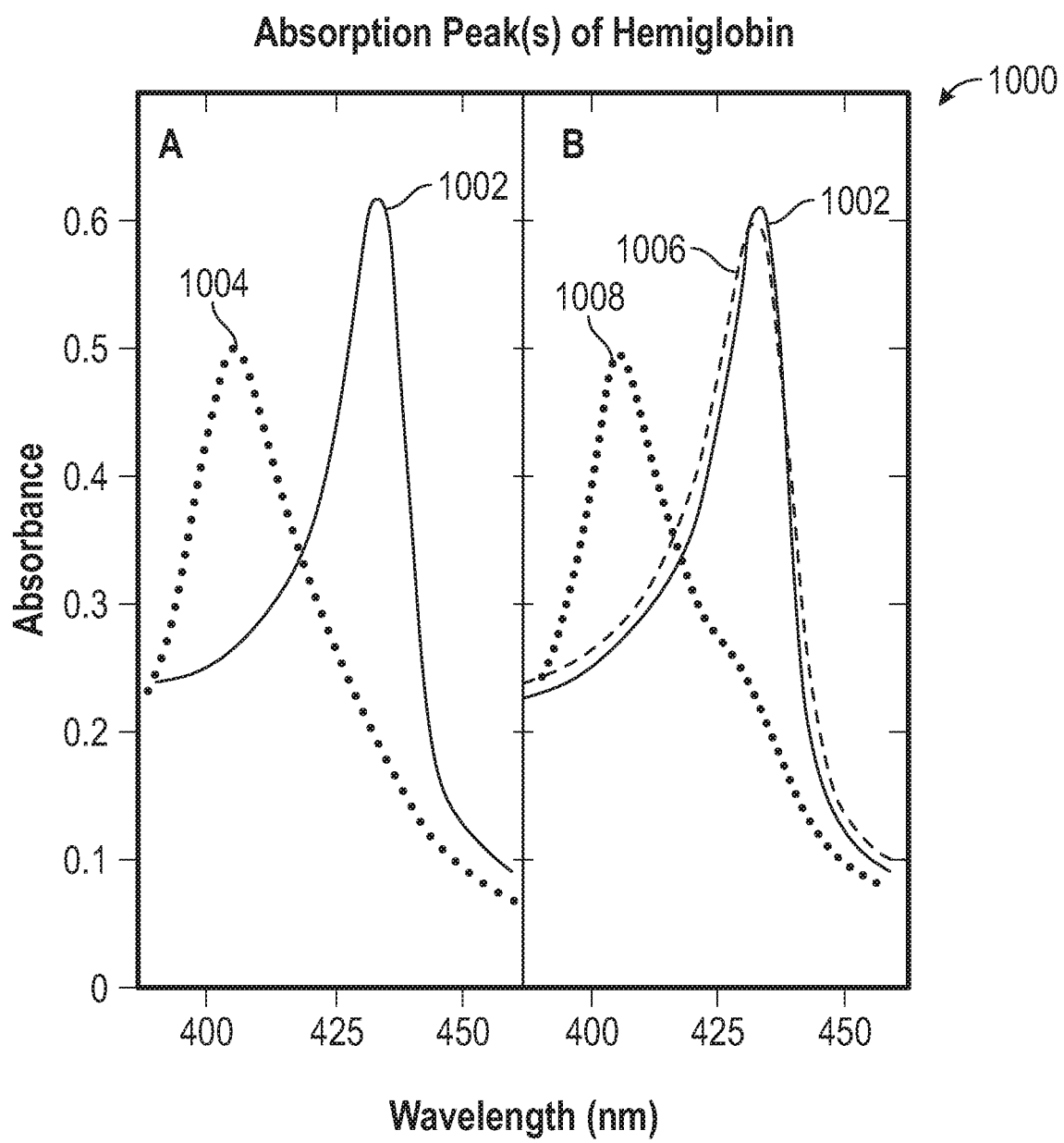
FIG. 10 illustrates a schematic block diagram of an exemplary embodiment of a graph illustrating a shift in absorbance peaks of hemoglobin in the presence of nitric oxide (NO).

FIG. 10 illustrates a schematic block diagram of an exemplary embodiment of a graph 1000 illustrating a shift in absorption peaks of hemoglobin in the presence of NO. In graph A, the curve 1002 illustrates the absorption spectra of reduced hemoglobin. The addition of nitric oxide (NO) shifts the absorption spectra curve 1002 to a lower wavelength curve 1004 due to the production of methemoglobin. In graph B, the absorption spectra curve 1002 of reduced hemoglobin is again illustrated. Endothelial cells are then added and the absorption spectra measured again. The curve 1006 illustrates that little change occurs in the absorption spectra curve 1002 of reduced hemoglobin in the presence of unstimulated endothelial cells. The curve 1008 illustrates the production of methemoglobin when the same dose of endothelial cells was given after stimulation of EDRF synthesis by the ionophore.

Though the absorbance spectrums shown in the graph 1000 were measured using in vitro assays, the biosensor 100 may detect nitric oxide in vivo using PPG techniques by measuring the shift in the absorption spectra curve 1002 of reduced hemoglobin in tissue and/or arterial blood flow. The absorption spectra curve 1002 shifts with a peak from around 430 nm to a peak around 411 nm depending on the production of methemoglobin. The greater the degree of the shift of the peak of the absorption spectra curve 1002, the higher the production of methemoglobin and NO concentration level. Correlations may be determined between the degree of the measured shift in the absorption spectra curve 1002 of reduced hemoglobin to an NO concentration level. The correlations may be determined from a large sample population or for a particular user and stored in a calibration database. The biosensor 100 may thus obtain an NO concentration level by measuring the shift of the absorption spectra curve 1002 of reduced hemoglobin. A similar method of determining shifts in an absorbance spectra may be implemented to determine a blood concentration level of other substances.

Figure 11:
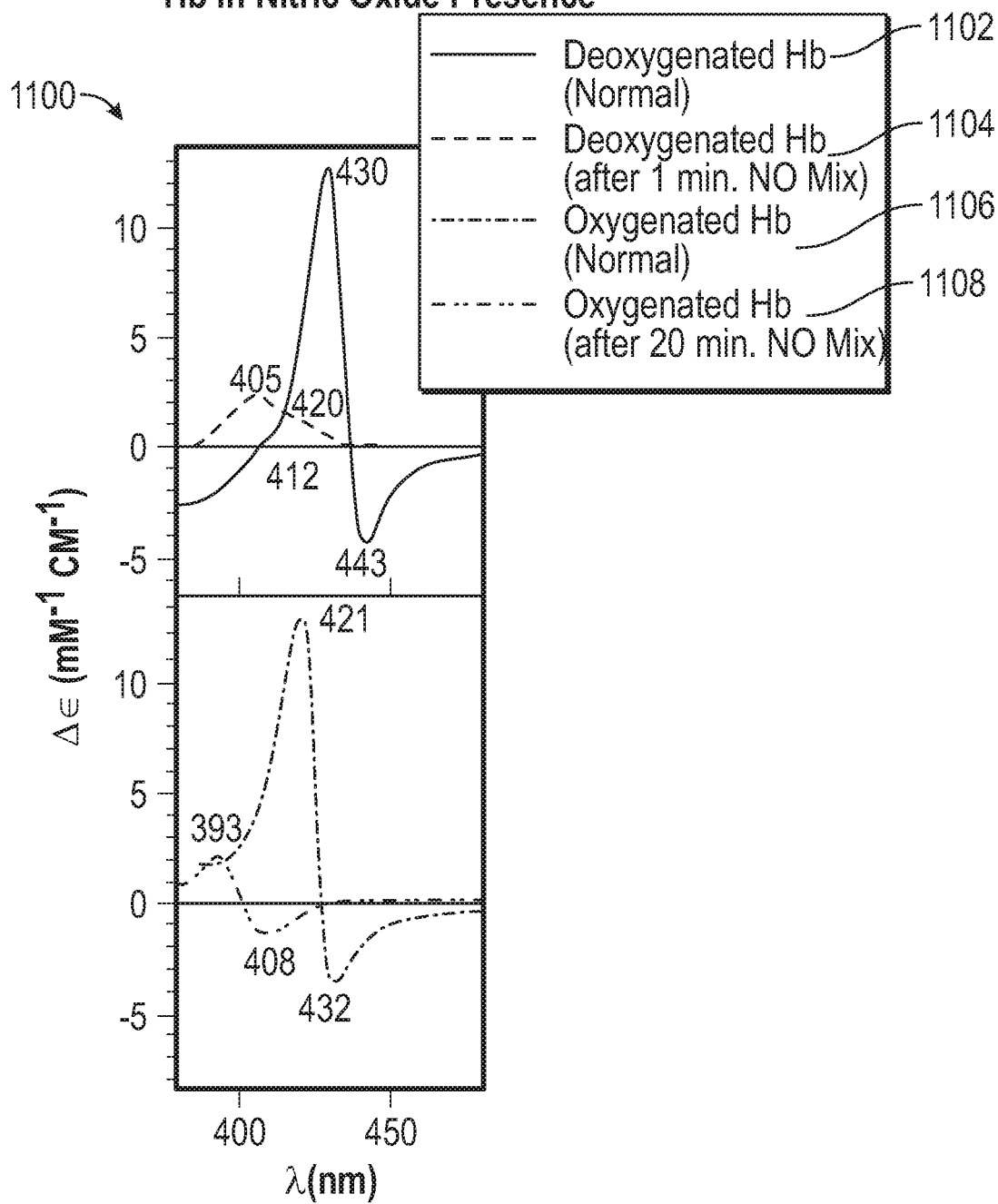
FIG. 11 illustrates a schematic block diagram of an exemplary embodiment of a graph illustrating a shift in absorbance peaks of oxygenated and deoxygenated hemoglobin (HB) in the presence of nitric oxide (NO).

FIG. 11 illustrates a schematic block diagram of an exemplary embodiment of a graph 1100 illustrating a shift in absorbance peaks of oxygenated and deoxygenated hemoglobin (HB) in the presence of nitric oxide NO. The absorbance spectra curve 1102 of deoxygenated HB has a peak of around 430 nm. After a one minute time period of exposure to a nitric oxide mixture, the absorbance spectra curve 1104 of deoxygenated HB shifted to a peak of around 405 nm. In addition, the absorbance spectra curve 1106 of oxygenated HB has a peak around 421 nm. After a twenty minute time period of exposure to a nitric oxide mixture, the absorbance spectra curve 1108 of oxygenated HB shifted to a peak of around 393 nm. The Deoxygenated Hb has an absorption peak at 430 nm (curve 1102) and in the presence of NO has a peak shift to 405 nm (curve 1104). The Oxygenated Hb has absorption peak at 421 nm (curve 1106) in presence of NO has peak shift to 393 nm (curve 1108).

Though the absorbance spectrums shown in the graph 1100 were measured using in vitro assays, the biosensor 100 may obtain an NO concentration level by measuring the shift of the absorbance spectra curve 1102 of deoxygenated hemoglobin and/or by measuring the shift of the absorbance spectra curve 1106 of oxygenated hemoglobin in vivo. The biosensor 100 may then access a calibration database that correlates the measured shift in the absorbance spectra curve 1102 of deoxygenated hemoglobin to an NO concentration level. Similarly, the biosensor may access a calibration database that correlates the measured shift in the absorbance spectra curve 1106 of oxygenated hemoglobin to an NO concentration level.

Figure 12:
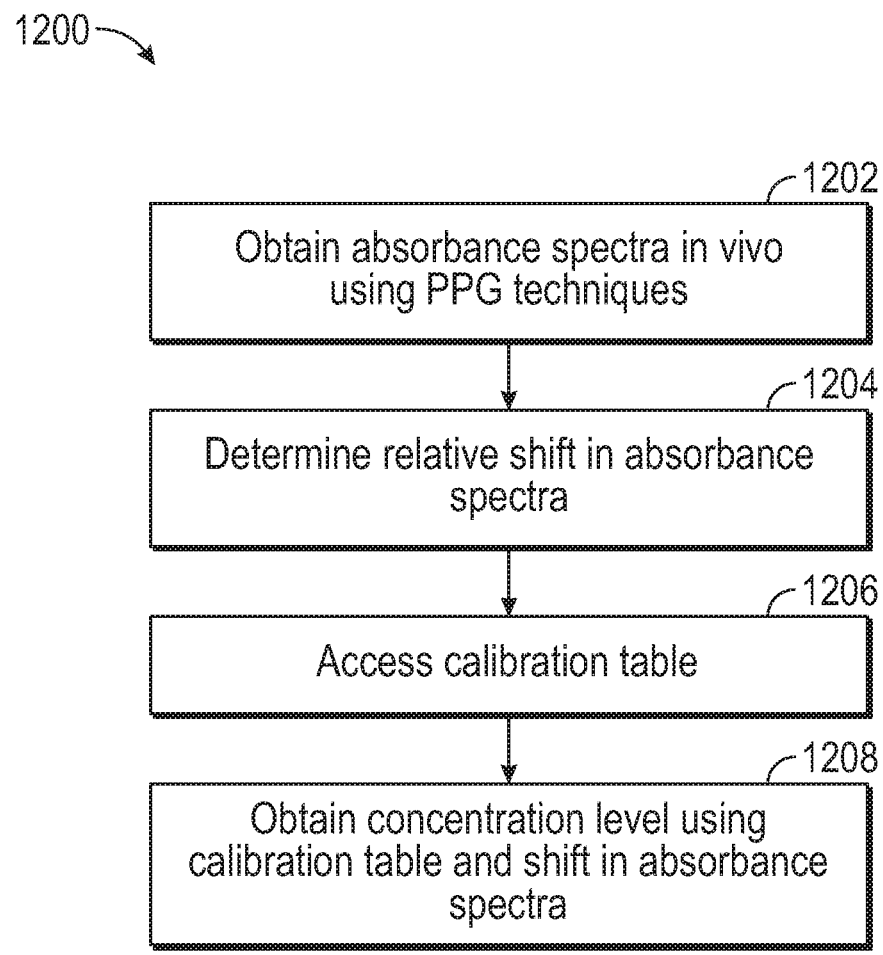
FIG. 12 illustrates a logical flow diagram of an exemplary embodiment of a method for measuring a concentration level of a substance in vivo using shifts in absorbance spectra

FIG. 12 illustrates a logical flow diagram of an exemplary embodiment of a method 1200 for measuring a concentration level of a substance in vivo using shifts in absorbance spectra. The biosensor 100 may obtain a concentration of the substance by measuring shifts in absorbance spectra of one or more substances that interact with the substance. For example, the one or more substances may include oxygenated and deoxygenated hemoglobin (HB). The PPG circuit 110 detects a spectral response at a plurality of wavelengths of the one or more substances that interact with the substance at 1202. The biosensor 100 determines the relative shift in the absorbance spectra for the substance at 1204. For example, the biosensor 100 may measure the absorbance spectra curve 1202 of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of the substance at 1206. The biosensor 100 may thus obtain a concentration level of the substance in blood flow using a calibration database and the measured relative shift in absorbance spectra at 1208.

The various methods thus include one or more of: Peak & Valley (e.g., peak detection), fast Fourier transform (FFT), and differential absorbance spectra curves. Each of the methods require different amounts of computational time which affects overall embedded computing time for each signal, and therefore can be optimized and selectively validated with empirical data through large clinical sample studies.

Figure 13:
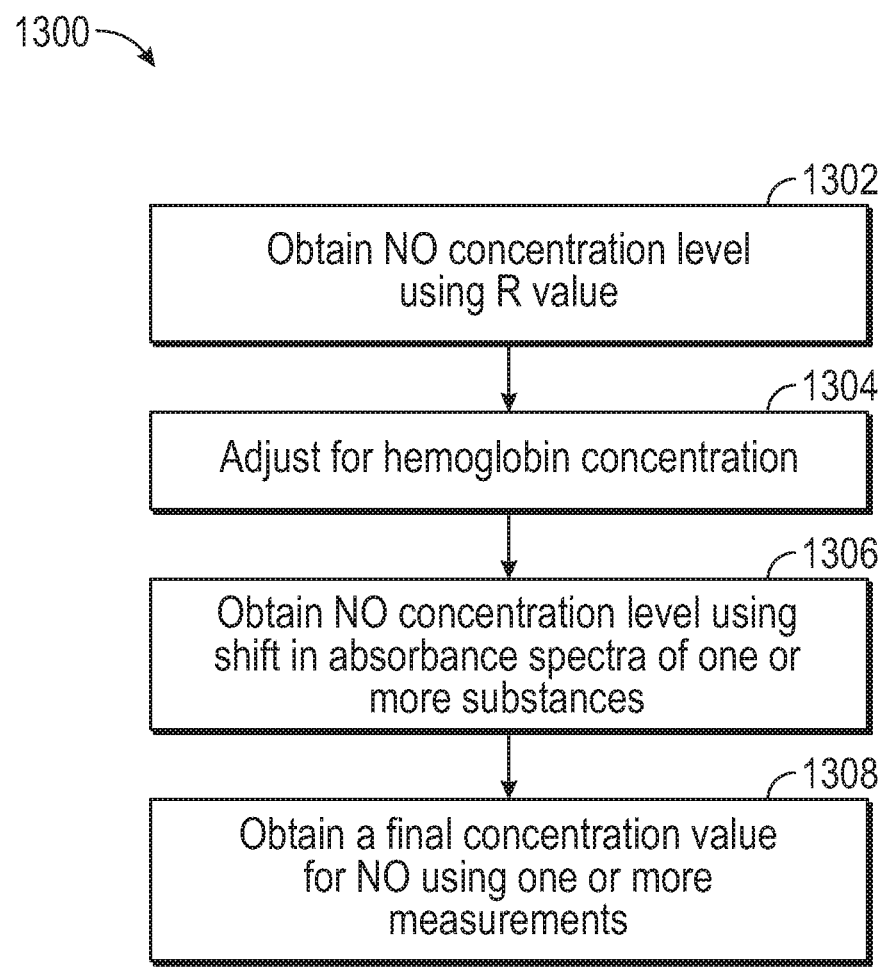
FIG. 13 illustrates a logical flow diagram of an exemplary embodiment of a method for measuring a concentration level of a substance in blood flow using one or more measurement techniques.

FIG. 13 illustrates a logical flow diagram of an exemplary embodiment of a method 1300 for measuring a concentration level of a substance in blood flow using one or more measurement techniques. In an embodiment, the biosensor 100 is configured to determine a concentration level of the substance in vivo using PPG technology and one or more measurement techniques described herein. For example, the biosensor 100 may determine an R value from L values obtained from a plurality of spectral responses at 1302. In another example, the biosensor may determine concentration level using absorption coefficients for the substance and associated isotopes and compounds over a plurality of wavelengths and adjusting or compensating for the compound concentrations (such as hemoglobin concentrations) at 1304. In another example, the biosensor 100 may determine the relative shift in the absorbance spectra for a substance (such as hemoglobin) and access a calibration database that correlates the relative shift in the absorbance spectra of the substance with a concentration level of the substance at 1306.

The biosensor 100 may use a plurality of these methods to determine a plurality of values for the concentration level of the substance at 1308. The biosensor 100 may determine a final concentration value using the plurality of values. For example, the biosensor 100 may average the values, obtain a mean of the values, etc.

The biosensor 100 may be configured for measurement on a fingertip or palm, wrist, an arm, forehead, chest, abdominal area, ear lobe, or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue. The PPG circuit 110 may adjust a power of the LEDs or a frequency or wavelength of the LEDs based on the underlying tissue. The biosensor 100 may adjust processing of the data. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor. For example, the calibration database may include different table or other correlations between R values and concentration level of a substance depending on position of the biosensor. Due to the different density of tissue and vessels, the R value obtained from measurements over an abdominal area may be different than measurements over a wrist or forehead or fingertip. The calibration database may thus include different correlations of the R value and concentration level depending on the underlying tissue. Other adjustments may also be implemented in the biosensor 100 depending on predetermined or measured characteristics of the underlying tissue of the body part.

Embodiment—Clinical Data

Figure 14:
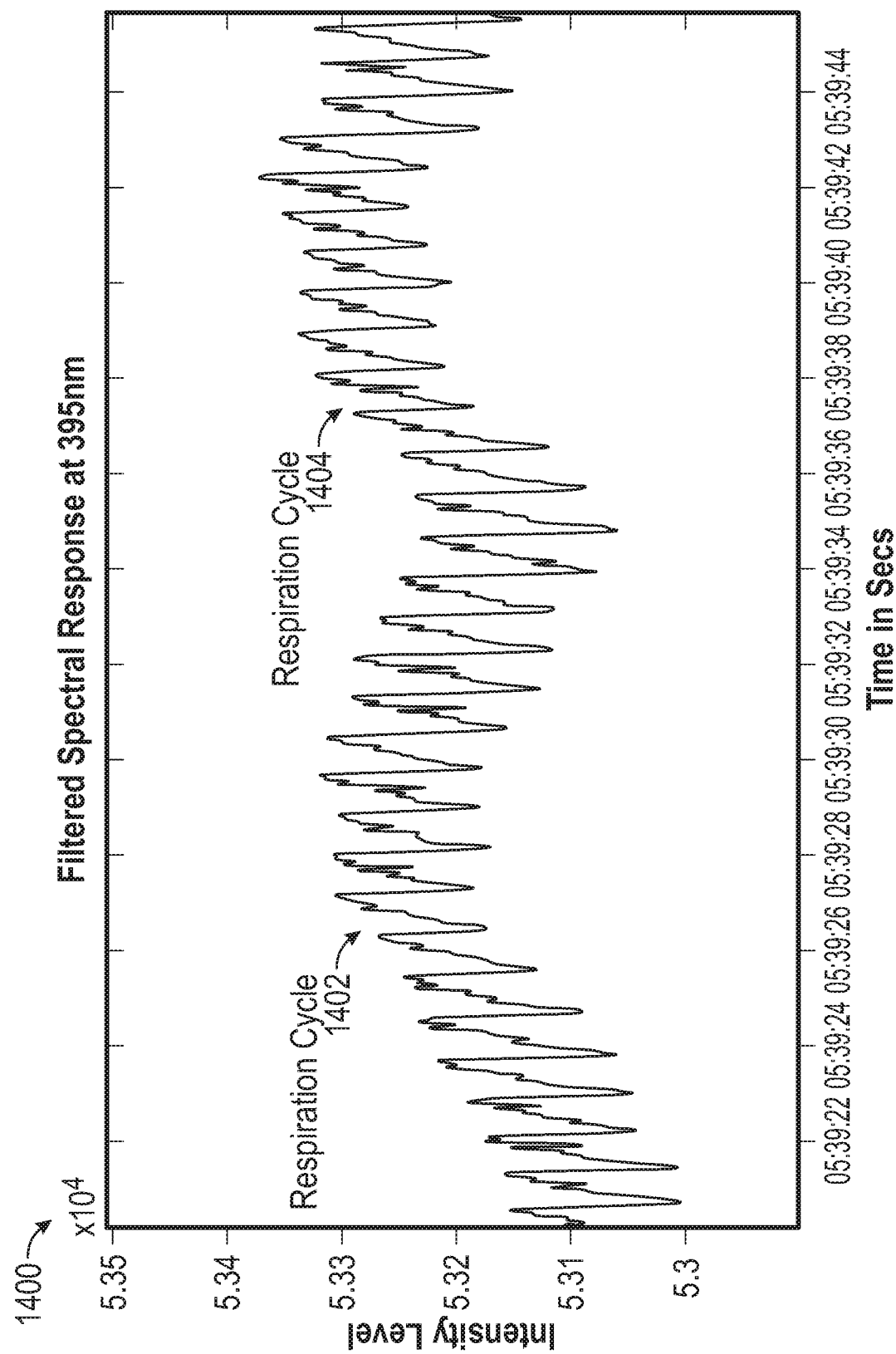
FIG. 14 illustrates a schematic drawing of an exemplary embodiment of results of a spectral response obtained using an embodiment of the biosensor from a user.

FIG. 14 illustrates a schematic drawing of an exemplary embodiment of results of a spectral response 1400 obtained using an embodiment of the biosensor 100 from a user. The spectral response 1400 was obtained at a wavelength of around 395 nm and is illustrated for a time period of about 40 seconds. The spectral response 1400 was filtered using digital signal processing techniques to eliminate noise and background interference to obtain the filtered spectral response 1400. A first respiration cycle 1402 and a second respiration cycle 1404 may be obtained by measuring the low frequency fluctuation of the filtered spectral response 1400. Due to this low frequency fluctuation, the biosensor 100 may obtain a respiratory rate of a user from the spectral response 1400. A heart rate may also be determined from the spectral response 1400 as well. For example, the biosensor 100 may determine the time between diastolic points or between systolic points to determine a time period of a cardiac cycle.

Figure 15:
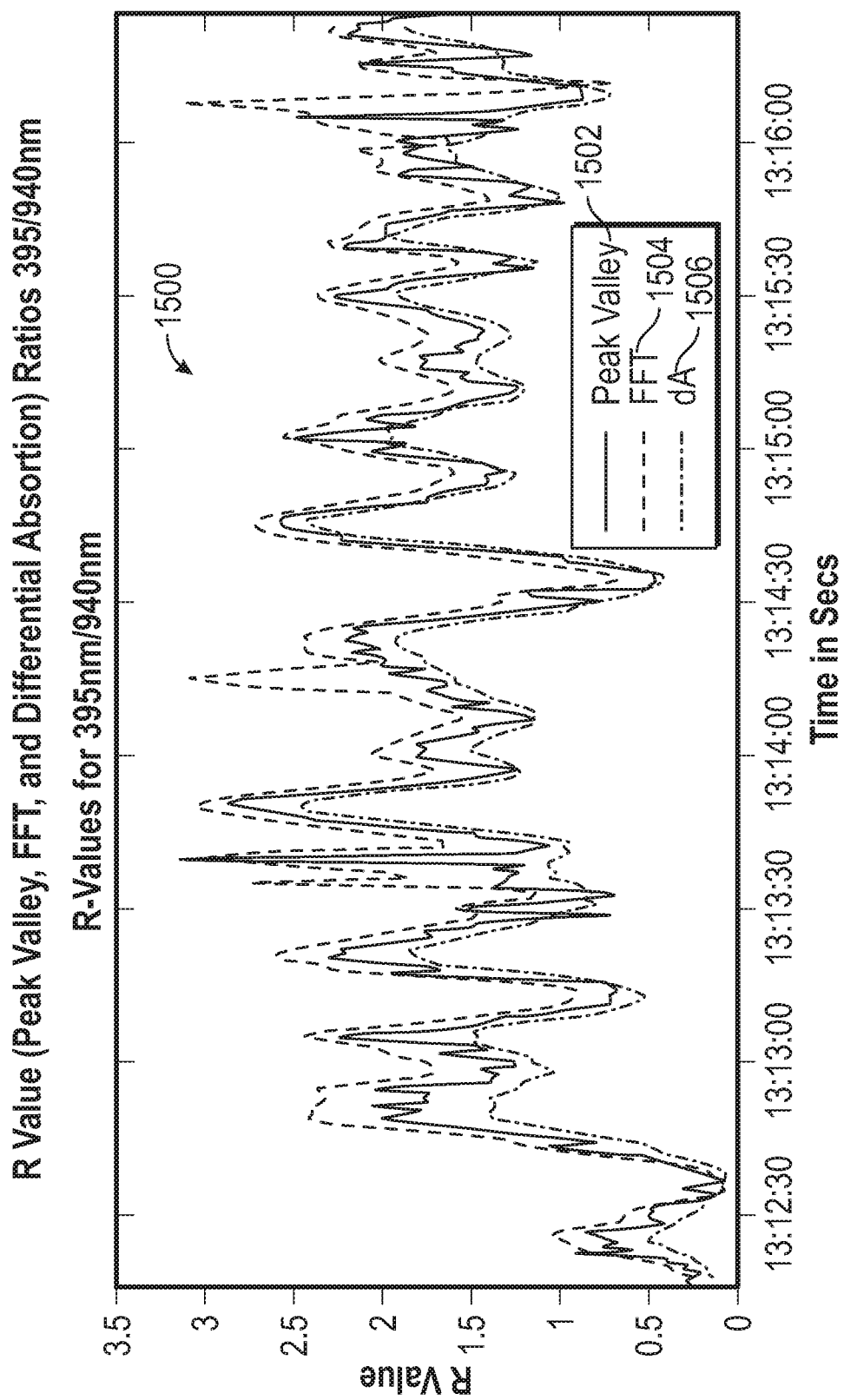
FIG. 15 illustrates a schematic drawing of an exemplary embodiment of results of R values determined using a plurality of methods.

FIG. 15 illustrates a schematic drawing of an exemplary embodiment of results of R values 1500 determined using a plurality of methods. The R values 1500 corresponding to the wavelengths of 395 nm/940 nm is determined using three methods. The R Peak Valley curve 1502 is determined using the Ratio $$R = \frac{L395}{L940}$$

as described hereinabove. The R FFT curve 1504 is obtained using FFT techniques to determine the $I_{DC}$ values of the spectral responses. The R differential absorption curve 1506 is determined using the shift in absorbance spectra as described hereinabove. As seen in FIG. 15, the determination of the R values using the three methods provides similar results, especially when averaged over a period of time. A mean or average of the R values in the curves 1502, 1504 and 1506 may be calculated to obtain a final R value or one of the methods may be preferred depending on the positioning of the biosensor or underlying tissue characteristics.

Figure 16:
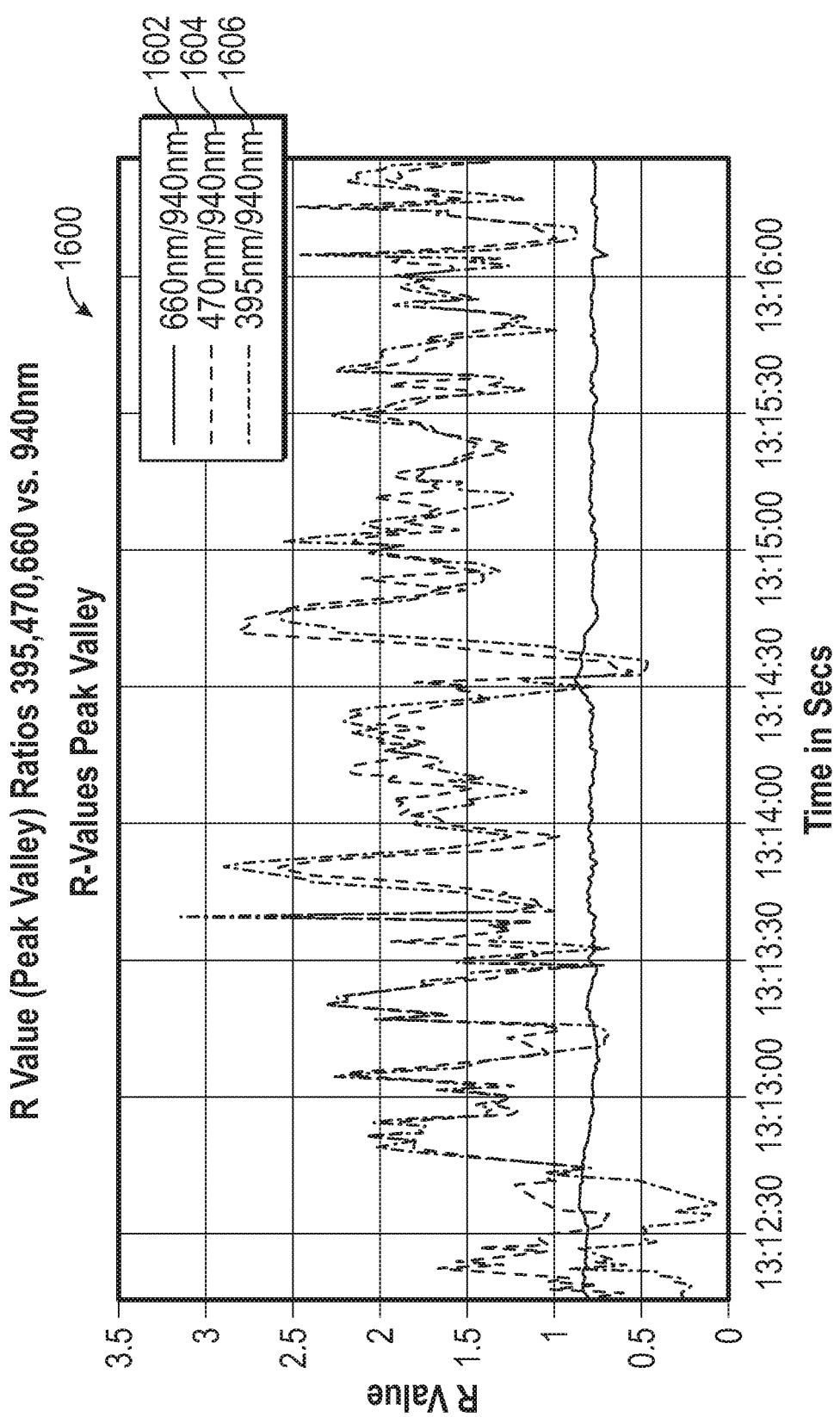
FIG. 16 illustrates a schematic drawing of an exemplary embodiment of results of R values for a plurality of wavelength ratios.

FIG. 16 illustrates a schematic drawing of an exemplary embodiment of results of R values 1600 for a plurality of wavelength ratios. The R values for 395 nm/940 nm 1606, the R values for 470 nm/940 nm 1604 and the R values for 660 nm/940 nm 1606 are shown over a time period of about 4 seconds.

Figure 17A:
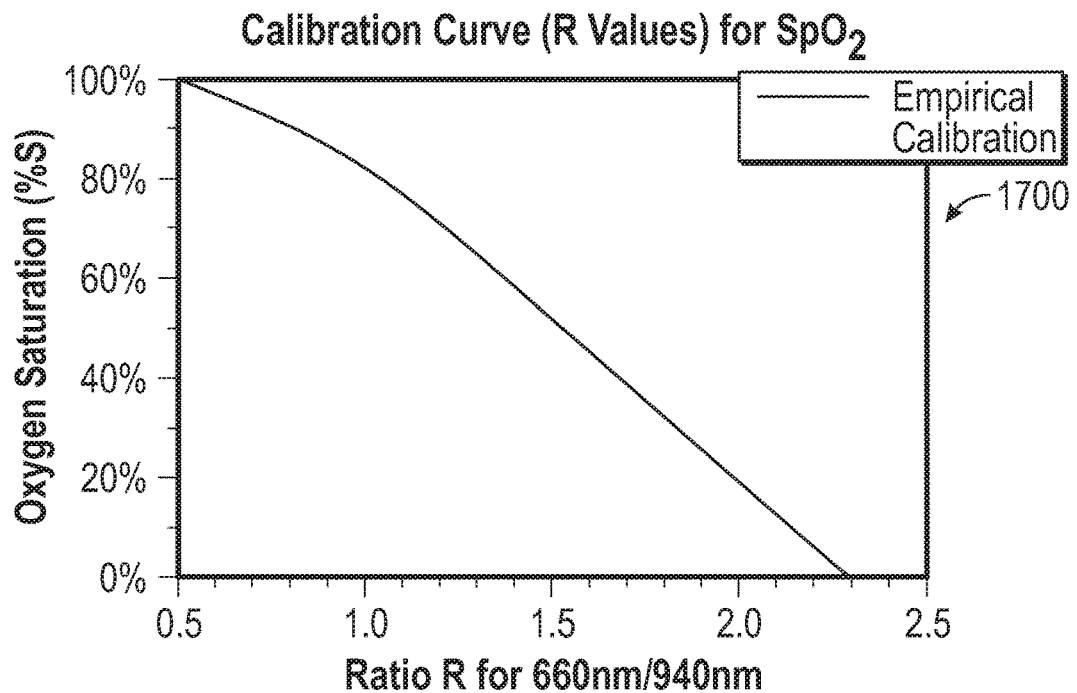
FIG. 17A illustrates a schematic drawing of an exemplary embodiment of an empirical calibration curve for correlating oxygen saturation levels ($SpO_2$) with R values.

FIG. 17A illustrates a schematic drawing of an exemplary embodiment of an empirical calibration curve 1700 for correlating oxygen saturation levels ($SpO_2$) with R values. The calibration curve 1700 may be included as part of the calibration database for the biosensor 100. For example, the R values may be obtained for $L_{660\ nm}/L_{940\ nm}$. In one embodiment, the biosensor 100 may use a light source in the 660 nm wavelength or in a range of +/−50 nm to determine $SpO_2$ levels, e.g. rather than a light source in the IR wavelength range. The 660 nm wavelength has been determined in unexpected results to have good results in measuring oxygenated hemoglobin, especially in skin tissue with fatty deposits, such as around the abdominal area.

Figure 17B:
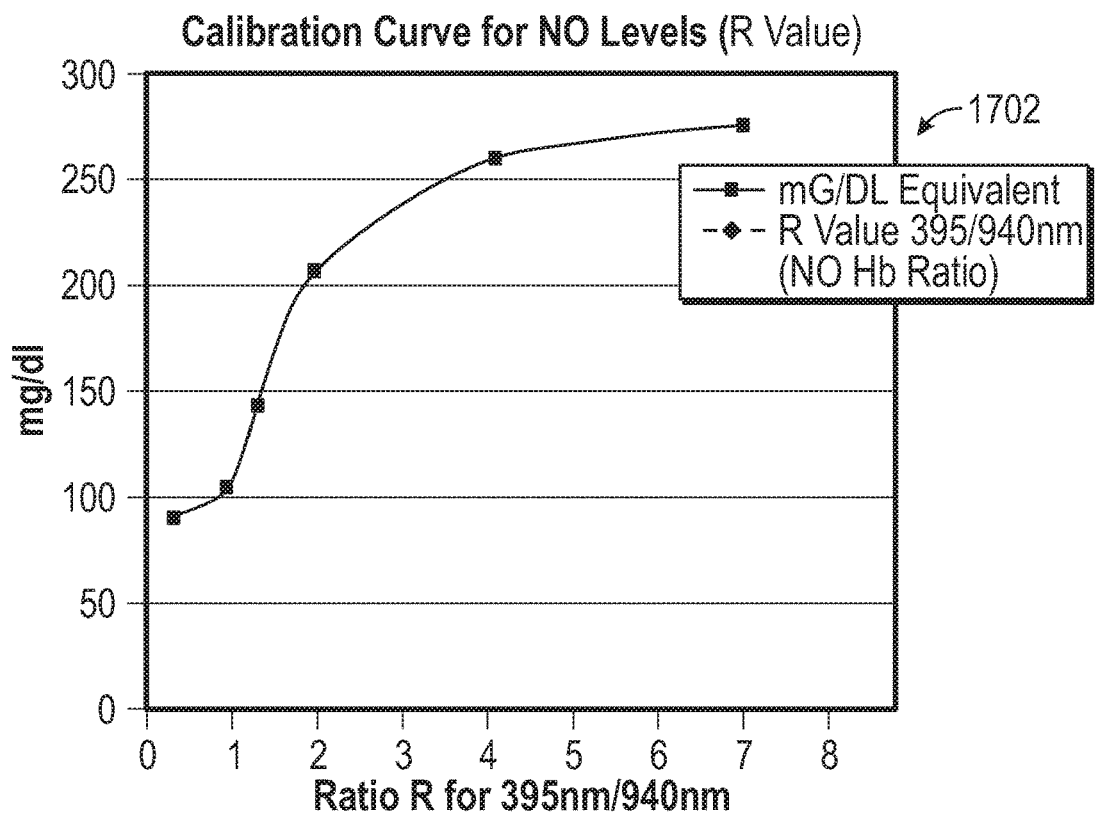
FIG. 17B illustrates a schematic drawing of an exemplary embodiment of an empirical calibration curve for correlating NO levels (mg/dl) with R values.

FIG. 17B illustrates a schematic drawing of an exemplary embodiment of an empirical calibration curve 1702 for correlating NO levels (mg/dl) with R values. The calibration curve 1702 may be included as part of the calibration database for the biosensor 100. For example, the R values may be obtained in clinical trials from measurements of $L_{395\ nm}/L_{940\ nm}$ and the NO levels of a general sample population. The NO levels may be measured using one or more other techniques for verification to generate such a calibration curve 1702. This embodiment of the calibration curve 1702 is based on limited clinical data and is for example only. Additional or alternative calibration curves may also be derived from measurements of a general population of users at one or more different positions of the biosensor 100. For example, a first calibration curve may be obtained at a forehead, another for an abdominal area, another for a fingertip, etc.

From the clinical trials, the L values obtained at wavelengths around 390 nm (e.g. 380-410) are measuring NO levels in the arterial blood flow. The R value for $L_{390}/L_{940\ nm}$ may thus be used to obtain NO levels in the pulsating arterial blood flow. From the clinical trials, it seems that the NO levels are reflected in the R values obtained from $L_{390\ nm}/L_{940\ nm}$ and wavelengths around 390 nm such as $L_{395\ nm}/L_{940\ nm}$. The NO levels may thus be obtained from the R values and a calibration database that correlates the R value with known concentration level of NO for the user or for a large general population.

In other embodiments, rather than $L_{\lambda 1}=390$ nm, the L value may be measured at wavelengths in a range from 410 nm to 380 nm, e.g., as seen in the graphs wherein $L_{\lambda 1}=395$ nm is used to obtain a concentration level of NO. In addition, $L_{\lambda 2}$ may be obtained at any wavelength at approximately 660 nm or above. Thus, R obtained at approximately $L\lambda 1=380$ nm-400 nm and $L\lambda 2 \geq 660$ nm may also be obtained to determine concentration levels of NO.

The concentration level of NO may be correlated to a diabetic risk or to blood glucose levels using a calibration database.

Embodiment—Measurements of Other Substances

Using similar principles described herein, the biosensor 100 may measure concentration levels or indicators of other substances in pulsating blood flow. For example, absorption coefficients for one or more frequencies that have an intensity level responsive to concentration level of substance may be determined. The biosensor 100 may then detect the substance at the determined one or more frequencies as described herein and determine the concentration levels using the Beer-Lambert principles and the absorption coefficients. The L values and R values may be calculated based on the obtained spectral response. In one aspect, the biosensor 100 may detect various electrolyte concentration levels or blood analyte levels, such as bilirubin and sodium and potassium. In another aspect, the biosensor 100 may detect sodium NACL concentration levels in the arterial blood flow to determine dehydration. In yet another aspect, the biosensor 100 may be configured to detect proteins or abnormal cells or other elements or compounds associated with cancer. In another aspect, the PPG sensor may detect white blood cell counts. In another aspect, the biosensor may detect blood alcohol levels.

For example, the biosensor 100 may also determine alcohol levels in the blood using wavelengths at approximately 390 nm and/or 468 nm. For example, an $R_{468,940}$ value for at least L468 nm/L940 nm may be used as a liver enzyme indicator, e.g. P450 enzyme indicator. The P450 liver enzyme is generated in response to alcohol levels. Thus, the measurement of the spectral response for the wavelength at approximately 468 nm may be used to obtain blood alcohol levels from the concentration levels of P450 and a calibration database.

In another embodiment, an $R_{562,640}$ value for at least $L_{562\ nm/L640\ nm}$ may be used as a digestive indicator to measure digestive responses, such as phase 1 and phase 2 digestive stages. In another aspect, the biosensor 100 may detect electrolytes, such as sodium, potassium, chloride, and bicarbonate. The biosensor 100 may detect white blood cell counts or concentration levels in arterial blood flow using similar PPG techniques. The presence of white blood cell counts may indicate the presence of infection.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100. Since the biosensor 100 may operate in multiple frequencies, various health monitoring tests may be performed concurrently.

Figure 18:
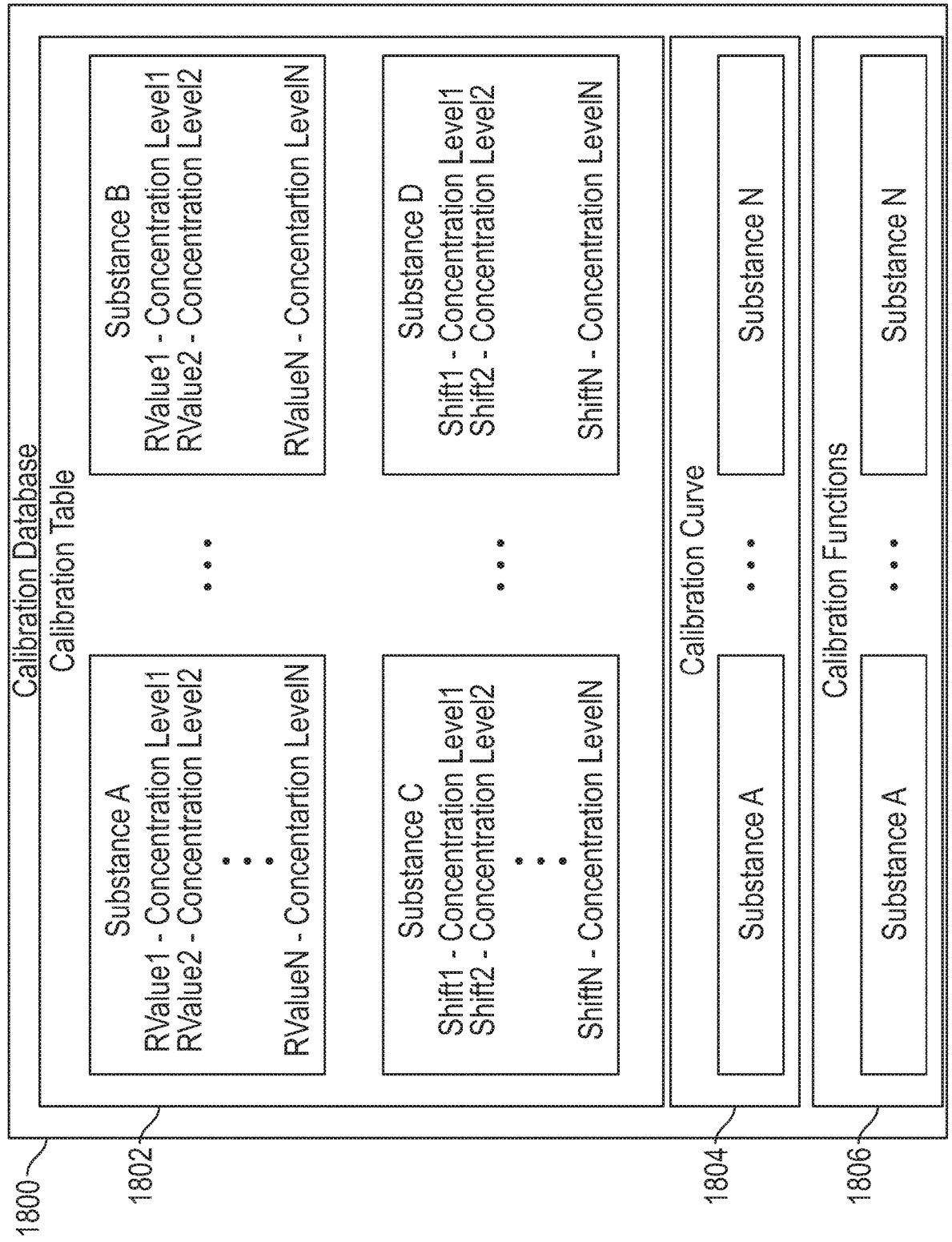
FIG. 18 illustrates a schematic block diagram of an embodiment of a calibration database.

FIG. 18 illustrates a schematic block diagram of an embodiment of a calibration database 1800. The calibration database 1800 includes one or more calibration tables 1802, calibration curves 1804 or calibration functions 1806 for correlating obtained values to concentration levels of one or more substances A-N. The concentration level of the substances may be expressed in the calibration tables 1802 as units of mmol/liter, as a saturation level percentage (SpNO %), as a relative level on a scale (e.g., 0-10), etc.

The calibration database 1800 may also include one or more calibration tables for one or more underlying skin tissue types. In one aspect, the calibration database 1800 may correlate an R value to a concentration level of a substance for a plurality of underlying skin tissue types.

In another aspect, a set of calibration tables 1802 may correlate an absorption spectra shift to a concentration level of one or more substances A-N. For example, a first table may correlate a degree of absorption spectra shift of oxygenated hemoglobin to NO concentration levels. The degree of shift may be for the peak of the absorbance spectra curve of oxygenated hemoglobin from around 421 nm. In another example, the set of table 1802 may correlate a degree of absorption spectra shift of deoxygenated hemoglobin to NO concentration levels. The degree of shift may be for the peak of the absorbance spectra curve of deoxygenated hemoglobin from around 430 nm.

The calibration database 1800 may also include a set of calibration curves 1804 for a plurality of substances A-N. The calibration curves may correlate L values or R values or degree of shifts to concentration levels of the substances A-N.

The calibration database 1800 may also include calibration functions 1806. The calibration functions 1806 may be derived (e.g., using regressive functions) from the correlation data from the calibration curves 1804 or the calibration tables 1802. The calibration functions 1806 may correlate L values or R values or degree of shifts to concentration levels of the substances A-N for one or more underlying skin tissue types.

Embodiment—Detection of Blood Type Using R Values

Determination of blood groups is a vital factor for overall healthcare needs. The human race by nature has any one of the blood groups namely A, B, AB and O. The blood group "AB" is called the "Universal acceptor" and the people with the "O" group are called "Universal donors". During blood transfusion any mismatch can lead to great harm or possible the death of a person. Hence it is very important for every person to identify his/her blood group.

There is no quick, non-invasive method to determine a patient's blood group. Known blood grouping methods are often a manual process with large & expensive equipment. Within a hospital or blood bank center, a number of blood samples have to be identified within a short span of time. The manual process is a laborious and time-consuming. Thus, there is a need for a quick, convenient and non-invasive method to determine a blood group of a patient, either human or animal.

The biosensor 100 described herein may be configured to assess the blood group of a patient, human or animal, using the PPG circuit 110. Blood type or group is represented by the ABO and Rh(D) systems. The A, B, O, AB blood type of a person depends on the presence or absence of two genes, A and B. These genes determine the configuration of the red blood cell surface. A person who has two A genes has red blood cells of type A. A person who has two B genes has red cells of type B. If the person has one A and one B gene, the red cells are type AB. If the person has neither the A nor the B gene, the red cells are type O. It is essential to match the ABO status of both donor and recipient in blood transfusions and organ transplants. In addition to the four main blood groups—A, B, AB and O, each group can either be RhD positive or RhD negative. Antigens are proteins on the surface of blood cells that can cause a response from the immune system. The Rh factor is a type of protein on the surface of red blood cells. Most people who have the Rh factor are Rh-positive. Those who do not have the Rh factor are Rh-negative. This means that in total there are eight main blood groups. The blood type of a patient exhibits different antigens present on the surface of red blood cells. The Rh factor is another type of protein on the surface of red blood cells.

In the last 30 years fully automated blood testing instruments have been developed and are in operation at blood centers and major hospitals. These instruments have advantages like high speed and sensitivity but they also require large size and high costs. These are major drawbacks. Development of a portable, low-cost, and sensitive instrument for blood typing is therefore required to make an on-site blood testing feasible. Aggulutination of RBCs (hemagglutination) is caused by an immune reaction between the RBCs and antibodies against the corresponding blood type. In conventional blood typing methods, hemagglutination caused by antibodies is detected by human eyes or by imaging techniques. Alternative methods of blood types using optical techniques have also been reported.

The optical properties of the different blood groups can be detected. The red blood cells comprise about 45% of the human blood. The color differences between the different blood groups are detectable. Thus, the optical differences between the different RBC groups (A, B, AB and O) can be determined using an optical sensor. For example, in the Armenian Journal of Physics, 2011, vol. 4, issue 3 pp. 165-168 shows a method for blood grouping detection using fiber optics. The basic premise of the method described is to use a laser operating at 820 nm to fire a series of pulses into a blood sample at 10 Khz, then using a photo diode, convert the optical variations back into electrical variations by amplifying, filtering, rectifying and feed the primary signal into a capacitor filter. This capacitor changes a voltage which is different for various blood groups. Since the different blood types have different optical spectrum characteristics, this method of fiber optic injection into a blood sample and then reading the approximate integration response of the corresponding signal shows a basic mathematical integration method is possible. However, this method requires a raw blood sample and is expensive and time consuming.

The spectral differences of the antigens present in the different blood types allow for several methods to be developed to determine the basic blood grouping using a multi-wavelength PPG circuit 110. For example, since the different blood groups have different optical spectrums due to variances in the antigen groups, the PPG circuit 110 described herein may be used to measure the spectral response of blood flow using multiple wavelengths and comparing the R values to determine a particular blood group. The various R values indicate a presence of an antigen to identify a blood group of A, B, O or AB using the plurality of spectral responses. The PPG circuit may use the same R values or different R values to determine a presence of another antigen within a blood group to identify an RH factor using the plurality of spectral responses.

In an embodiment, the PPG circuit emits a series of pulses at a patient's tissue to obtain spectral responses at plurality of wavelengths. The spectral data is processed to obtain a series of R values. The series or average of the series of R values is used to identify a blood grouping or antigen group. The PPG circuit 110 pulses a series of LEDs at a rate of between 100-200 Hz to obtain a PPG signal. The PPG signal includes a series of pressure waveforms over a series of cardiac cycles. One or more of the following R values for 550/940 nm, 660/940 nm, and 880 nm/940 nm frequencies may be obtained over an integration of a series of the cardiac cycles. Due to the division of the L values, the R value eliminates the input from the skin tissue and non-pulsating blood flow to isolate the input from the pulsating blood flow (venous or arterial). To determine a blood group, the R values may be obtained over a sample window, such as over a plurality of pressure waveforms (e.g., generated over a plurality of cardiac cycles). A blood group indicator may be derived from the values of the R ratio over the sample window. For example, an integration of the R values over the sample window may be determined, and then the integrated R values used as the blood group indicator. The blood group indicator is then used to identify a blood group from one or more blood group reference tables.

In order to enhance the data signal of a spectral response, the data signal in a spectral response over a series of heart beats is used for the sample window. The R value may be obtained over the sample window using spectral responses around a plurality of frequencies. The frequencies may include, e.g., 550, 660 and 880 nm frequencies or in ranges of wavelengths around such frequencies. In one embodiment, the frequencies include 530 and 590 nm and values for the ratio $R=L_{530}/L_{940}$ and $R=L_{590}/L_{940}$ are determined over the sample window. The values for the first $R_{530/940}$ ratio are then integrated across the sample window to determine an integrated R value as a first blood group indicator. The values for the second $R_{590/940}$ ratio are then integrated across the sample window to determine an integrated R value as a second blood group indicator. A simple integration algorithm for each individual frequency may be implemented to obtain the blood group indicators. In another embodiment, the values for the R ratios are averaged over the sample window. Other functions using the values of the R ratios over the sample window may be implemented to obtain one or more blood group indicators.

The obtained one or more blood group indicators are then used with a calibration table to identify a blood group of the patient, human or animal. For example, the calibration table includes a correlation of values or ranges of the one or more blood group indicators to blood group or blood type. The calibration table may be determined by obtaining the blood group indicator for a sample general population for each known blood type.

Figure 19A:
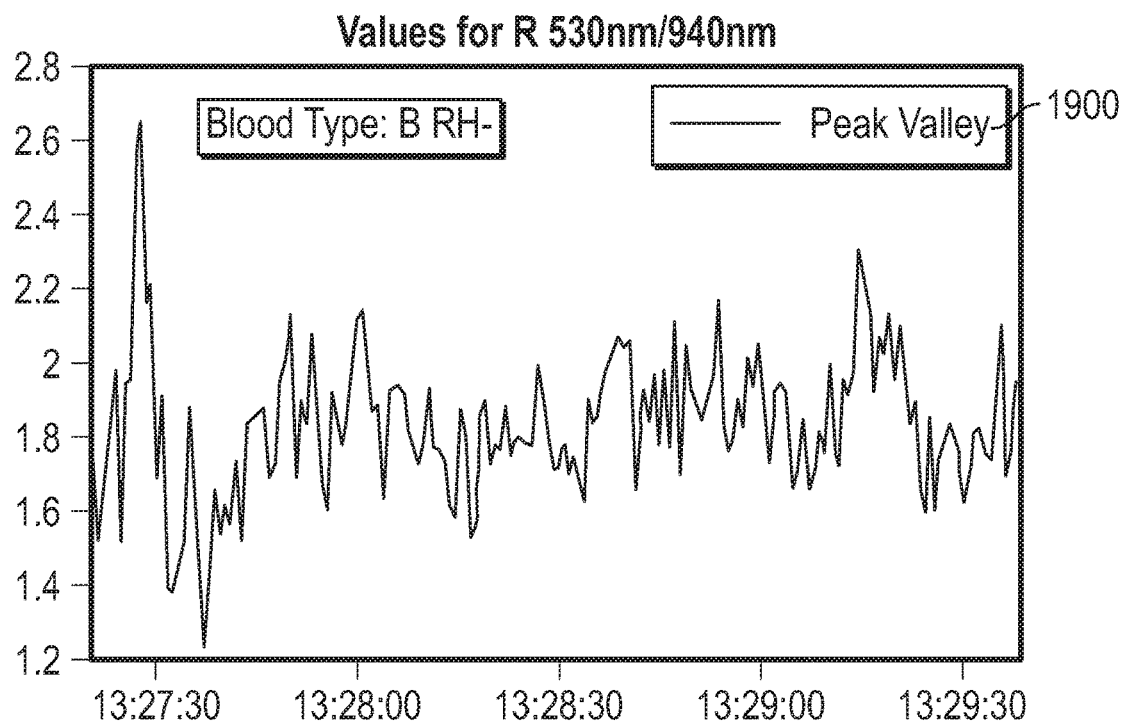
FIG. 19A illustrates a schematic drawing of values for the $R_{530/940}$ ratio obtained in a clinical setting using a biosensor with a PPG circuit.

FIG. 19A illustrates a schematic drawing of values for the $R_{530/940}$ ratio 1900 obtained in a clinical setting using a biosensor 100 with a PPG circuit 110. The biosensor 100 obtained values for the $R_{530/940}$ ratio 1900 over a sample window of approximately two minutes. In this embodiment, it was known that the patient had a blood type of B RH−. An average of the values for the $R_{530/940}$ ratio 1900 over the sample window was obtained.

Figure 19B:
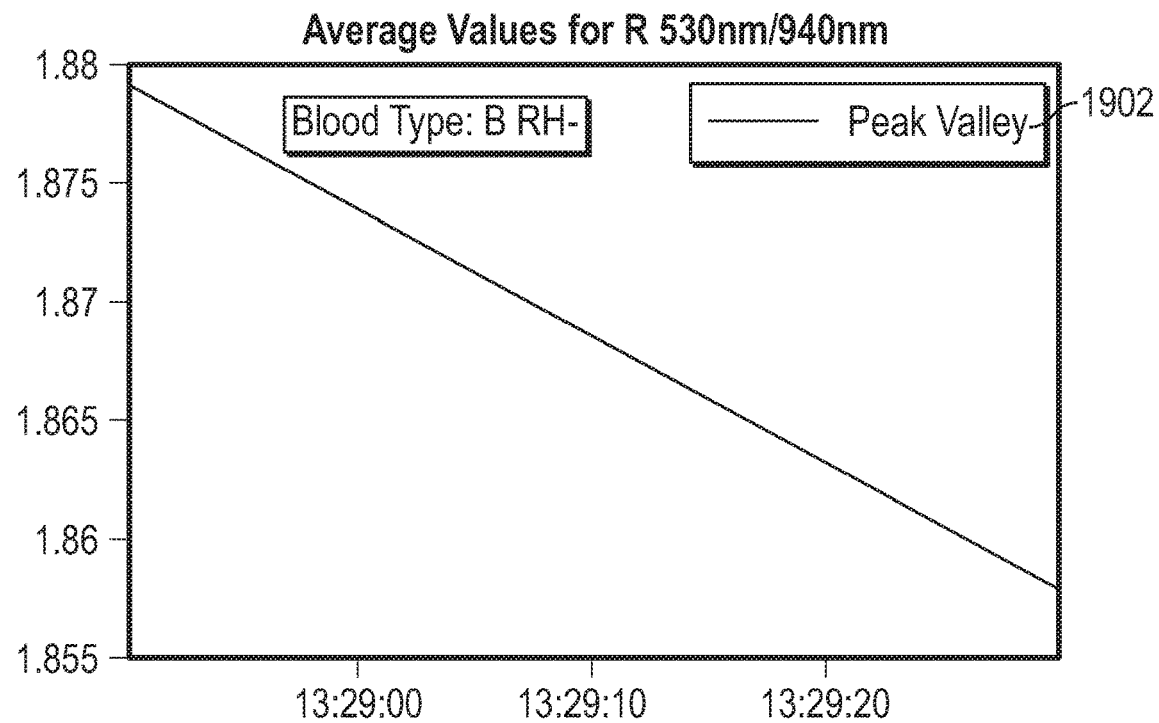
FIG. 19B illustrates a schematic drawing of the average values for the $R_{530/940}$ ratio obtained using the biosensor.

FIG. 19B illustrates a schematic drawing of the average values for the $R_{530/940}$ ratio 1902 obtained using the biosensor 100. As seen in FIGS. 19A and 19B, the values for the $R_{530/940}$ ratio are determined over the sample window. In this example, an average R value over the sample window is obtained between 1.88 and 1.855.

Figure 20A:
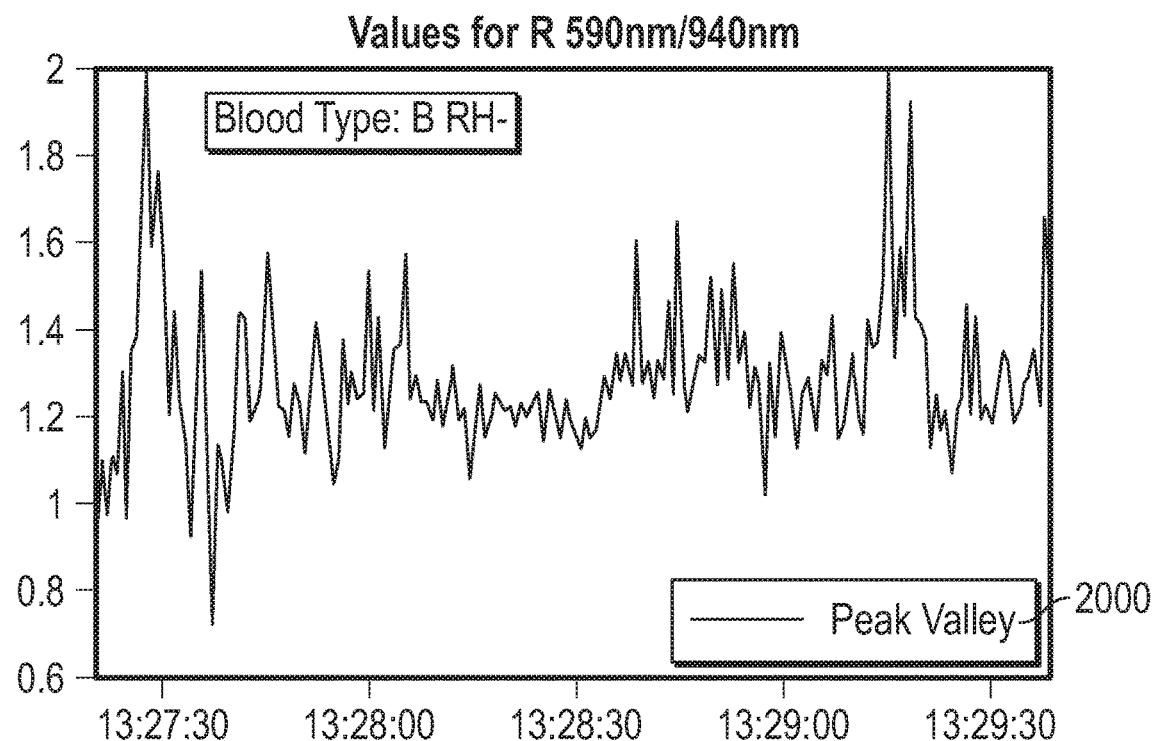
FIG. 20A illustrates a schematic drawing of values for the $R_{590/940}$ ratio obtained using the biosensor.

FIG. 20A illustrates a schematic drawing of values for the $R_{590/940}$ ratio 2000 obtained using the biosensor 100. The biosensor 100 obtained values for the $R_{590/940}$ ratio 2000 over a sample window of approximately two minutes. In this embodiment, it was known that the patient had a blood type of B RH–. An average of the values for the $R_{590/940}$ ratio 2000 over the sample window was obtained.

Figure 20B:
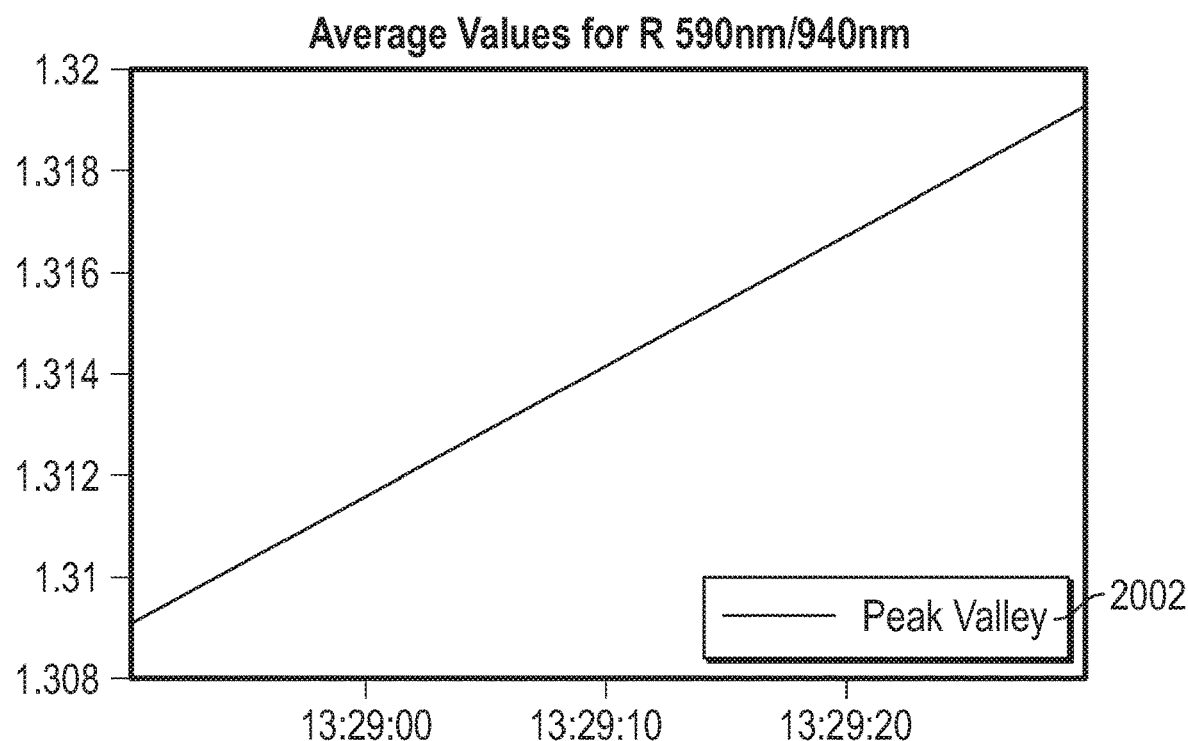
FIG. 20B illustrates a schematic drawing of average values for the $R_{590/940}$ ratio obtained using the biosensor.

FIG. 20B illustrates a schematic drawing of average values for the $R_{590/940}$ ratio 2002 obtained using the biosensor 100. As seen in FIGS. 20A and 20B, the values for the $R_{590/940}$ ratio are determined over the sample window. In this example, an average R value over the sample window is obtained between 1.308 and 1.32.

In one aspect, the blood type indicators for the patient may include an average $R_{530/940}$ value and an average $R_{530/940}$ value. Other blood type indicators may be derived from the values for the $R_{530/940}$ ratio and the values for the $R_{590/940}$ ratio. For example, other functions or processes, such as mean values, integral values, etc., obtained using the R values may also act as blood type indicators.

Figure 21:
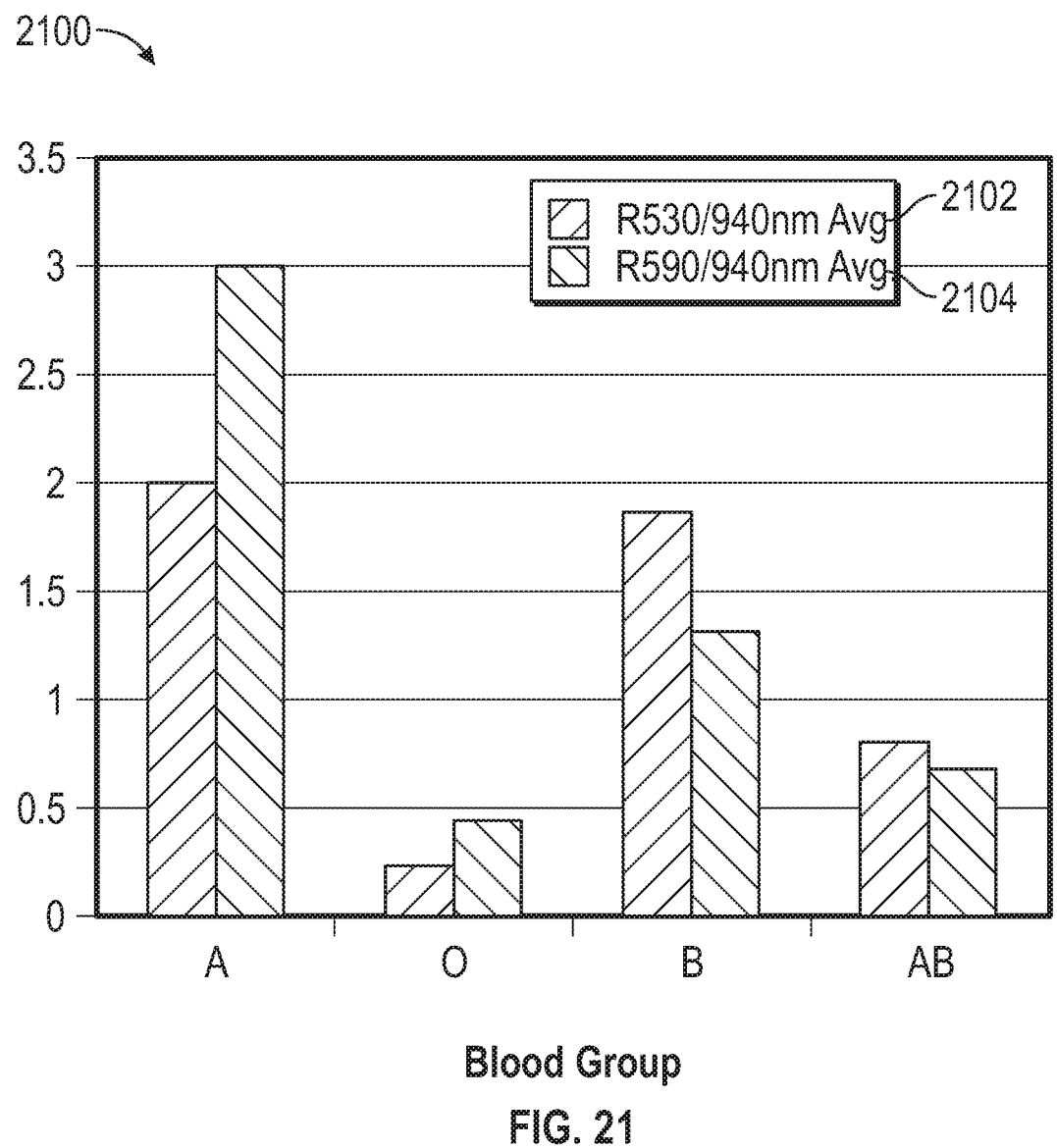
FIG. 21 illustrates a schematic drawing of an embodiment of a calibration table for a set of blood groups.

FIG. 21 illustrates a schematic drawing of an embodiment of a calibration table for a set of blood groups. The blood group reference table 2100 includes an expected or predetermined range of average values for R ratios for a set of blood groups types A, O, B, and AB. For example, the blood group reference table 2100 associates the average values for R ratios to a plurality of types of antigens on a surface of red blood cells. Each of the plurality of types of antigens corresponds to a blood type. By accessing the calibration table, a blood group may be identified. In this embodiment, the blood type indicators include an average $R_{530/940}$ value 2102 and an average $R_{530/940}$ value 2104. The expected average values for the blood group indicators of $R_{530/940}$ ratio 2102 and $R_{590/940}$ ratio 2104 are shown for each of the blood groups A, O, B and AB.

To determine the blood group of a patient, a measured average $R_{530/940}$ value of the patient is compared to the blood group reference table 2100. A measured average $R_{590/940}$ value of the patient may also be compared to the blood group reference table 2100. For the patient in the example shown in FIG. 19A, for the measured average $R_{530/940}$ value between 1.88 and 1.855, the Blood Group type of B may thus be determined using the blood group reference table 2100. Similarly, using the example shown in FIG. 19B, for the measured average R590/940 value between 1.308 and 1.32, the Blood Group type of B may thus be determined using the blood group reference table 2100.

Though the RH factor (RH+ and RH–) is not shown in this blood group reference table 2100, a similar calibration graph or table may be used to determine the RH factor of each Blood Group A, B, AB and O. For example, the blood group A, B, AB and O may first be determined and then the RH+ and RH– type determined using the same or different blood type indicators. In another embodiment, the blood group A, B, AB and O and RH+ and RH– type may be determined using a same calibration table and blood type indicators. For example, values of the R ratio at 535 nm/940 nm may be used to detect either Rh+ or Rh–.

In another embodiment, though two blood type indicators are illustrated herein, three or more blood type indicators may be used to determine the blood type or a single blood type indicator may be used to determine the blood type. For example, a first blood type indicator may be determined and compared with the blood group reference table 2100. If the first blood type indicator fails to correlate with an expected value for a blood type, one or more additional blood type indicators may be obtained and compared with the blood group reference table 2100. In addition, though the blood group reference table 2100 illustrates a single predetermined value for each blood type indicator, the blood group reference table 2100 may indicate a range of predetermined values for one or more blood type indicators.

The various R values indicate a presence of an antigen to identify a blood group of A, B, O or AB using the plurality of spectral responses. The PPG circuit may use the same R values or different R values to determine a presence of another antigen within a blood group to identify an RH factor using the plurality of spectral responses. Though R values are described herein, other blood type indicators derived from a spectral response may also be implemented herein.

Figure 22:
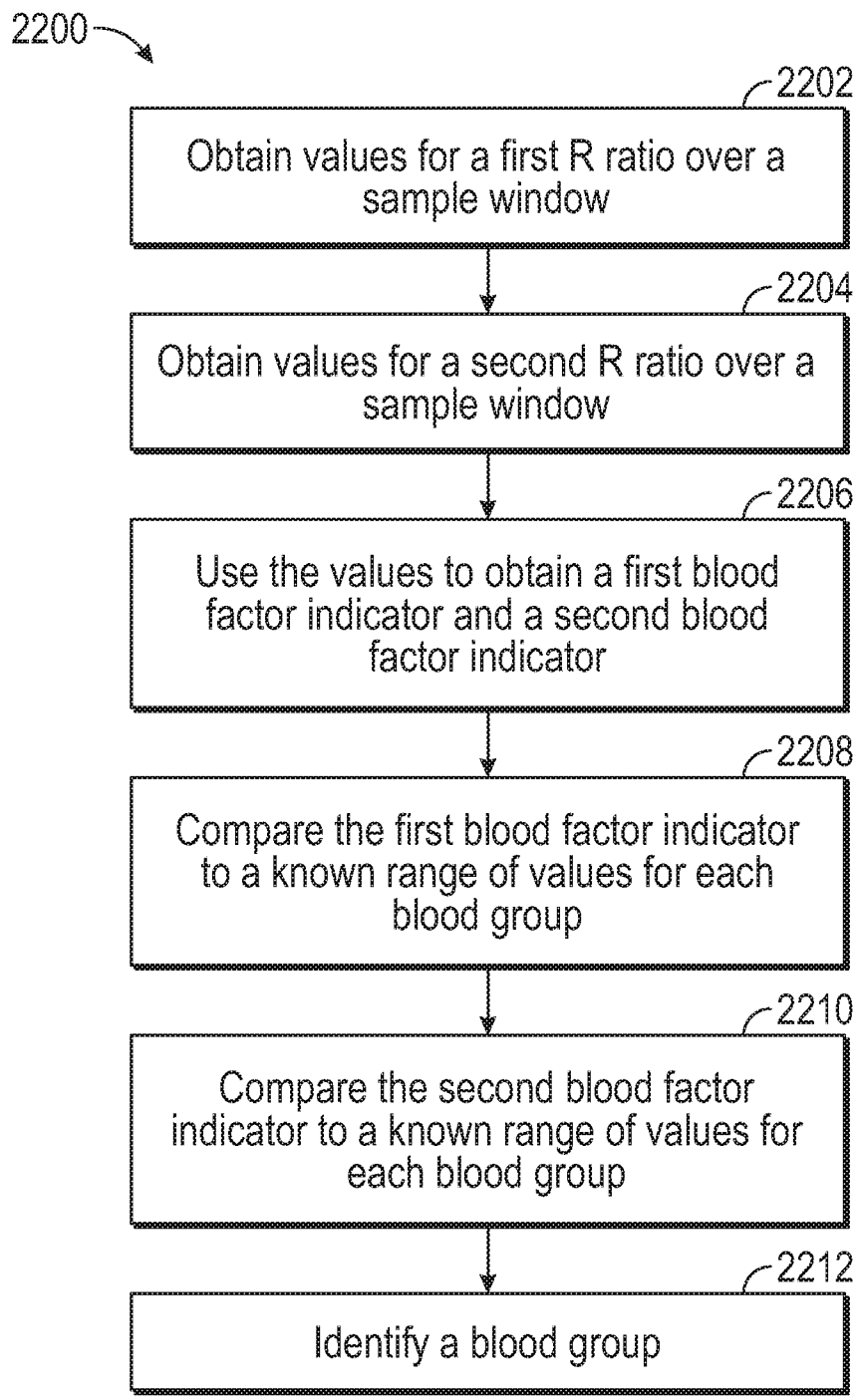
FIG. 22 illustrates a logical flow diagram of a method for obtaining a blood type using the biosensor.

FIG. 22 illustrates a logical flow diagram of a method 2200 for obtaining a blood type using the biosensor 100. The biosensor 100 obtains values for a first R ratio over a sample window at 2202. The biosensor 100 obtains values for a second R ratio over a sample window at 2204. The values of the first and second R ratios are used to obtain a first blood factor indicator and a second blood factor indicator at 2206. For example, the blood factor indicator may be derived from an average, mean or integration of the values of the R ratio over the sample window. Other functions or processes may be used to determine a blood factor indicator from the values of an R ratio over a sample window.

The first blood factor indicator is compared to a range of expected or predetermined values for each of a plurality of blood groups in a calibration table at 2208. For example, the calibration table associates the blood factor indicator to a plurality of types of antigens on a surface of red blood cells. Each of the plurality of types of antigens corresponds to a blood type. By accessing the calibration table, a blood group may be identified. The second blood factor indicator is compared to a range of expected or predetermined values for each of a plurality of blood groups in the calibration table at 2210. Based on the first or second comparison or both, a blood group is identified at 2212.

The biosensor 100 may thus be configured to determine a blood group A, B, O, AB and RH+ and RH– using one or more blood type indicators and a blood group reference table 2100. A blood type indicator is obtained using values of an R ratio over a sample window. A different R ratio and blood type indicator may be used for comparison based on the blood group (such as, A, B, O, AB). For example, an expected range of values for a first blood type indicator derived from a first R ratio may be listed for blood group A while an expected range of values for a second blood type indicator derived from a second different R ratio may be listed for blood group O. The biosensor 100 may obtain the first and/or second blood type indicators in series or parallel and use the calibration table to determine the blood type. The various calibration tables, curves or other correlations may be stored in the calibration database 1800.

Embodiment—Detection of Blood Type Using Signal Quality Parameters

The spectral differences of the antigens present on the surface of red blood cells in different blood types affects the quality of the PPG signal. For example, the reflectance of different types of surfaces of the red blood cells affects the scattering of light transmitted from the PPG circuit 110.

These differences in signal quality are measurable, especially in a reflectance PPG signal (vs. a transmissive PPG signal) due to the differing light scattering properties. In known solutions, an automatic gain filter or other digital signal processing compensates for the different qualities of the PPG signal.

However, when a uniform gain or filter is applied to the PPG signal from patients of different blood types, the differences in the signal strength and qualities of the PPG signal may be measured and used to determine the blood type. The different blood groups have different optical properties due to variances in the antigen groups on the surface of the red blood cells. Thus, the quality of the PPG signal quality is affected by the type of blood group due to the different antigens on the surface of the RBCs. Various parameters that measure signal quality or signal strength of the PPG signal may be determined and compared to predetermined values to determine the blood type. These differences in PPG signal quality are preferably determined at a similar gain or amplification.

There are various signal quality parameters that may be implemented to compare the differences in signal quality and strength of the PPG signal across blood types. For example, using a similar gain or amplification and other filtering or signal processing, the cross-correlation and auto-correlation of PPG signals, may be measured to determine different blood types. Other signal quality parameters may also be implemented to determine different blood types, such as a signal to noise ratio (SNR), skewness index ($S_{SQI}$), a kurtosis index ($K_{SQI}$), entropy ($E_{SQI}$), relative power, or other indices of signal quality or strength. An example of types of signal quality parameters that may be implemented herein are described in, Elgendi, Mohamed, "Optimal Signal Quality Index for Photoplethysmogram Signals." Ed. Gou-Jen Wang. Bioengineering 3.4 (2016): 21, which is hereby incorporated by reference herein. The various signal quality parameters measure the signal quality and/or signal strength of the PPG signal. A signal quality parameter may be implemented as another blood type indicator.

Figure 23A:
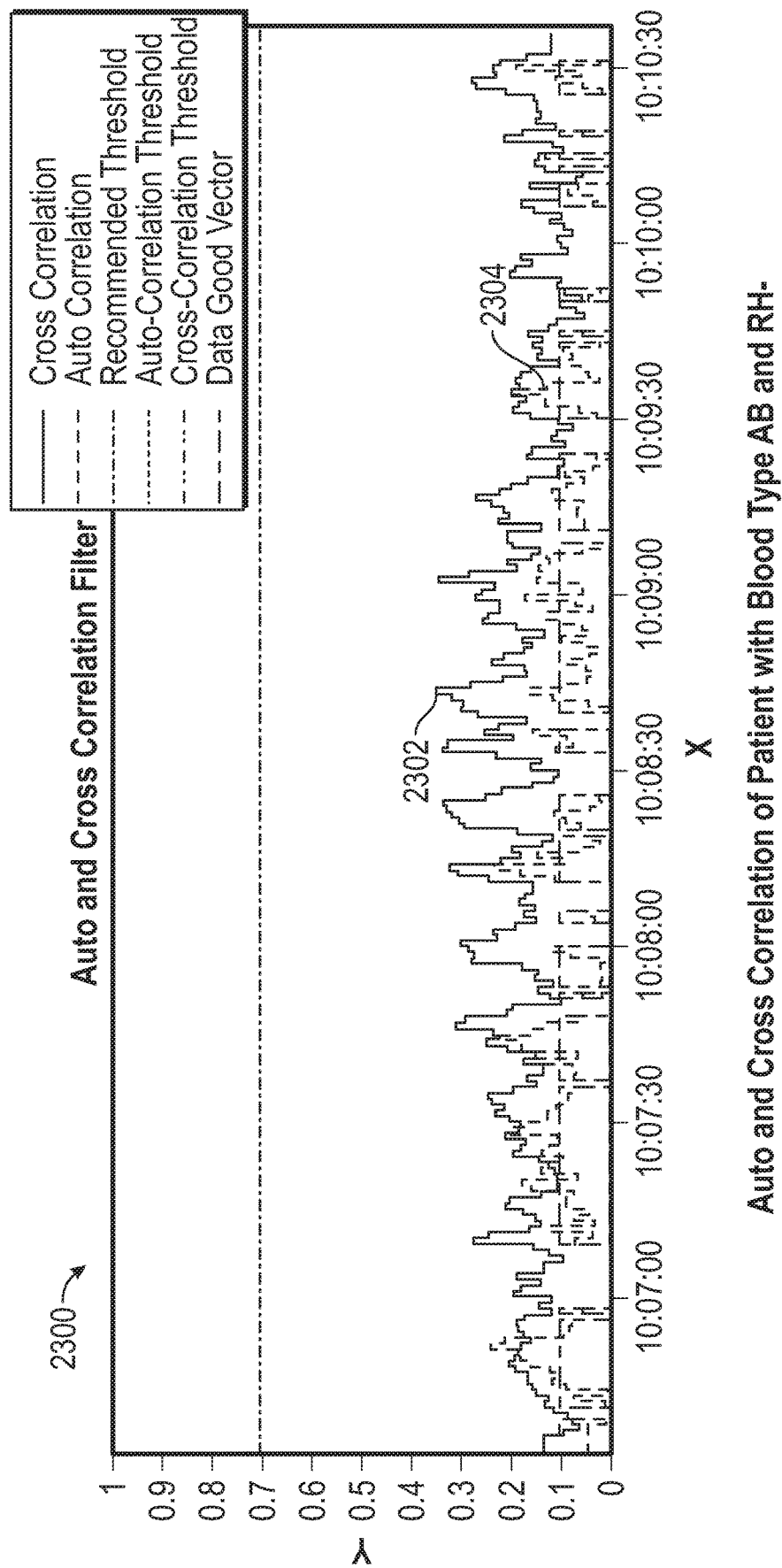
FIG. 23A illustrates a schematic graph of an example of clinical data of signal quality parameters for detecting blood type in a patient with blood Type AB and RH−.

FIG. 23A illustrates a schematic graph 2300 of an example of clinical data of signal quality parameters for detecting blood type in a patient with blood Type AB and RH−. In this example, the signal quality parameters include a cross-correlation 2302 and an auto-correlation 2306 of PPG signals. The cross correlation 2402 illustrates a cross correlation of a PPG signal obtained at 530 nm and a PPG signal obtained at 940 nm. The auto-correlation 2406 illustrates an auto-correlation of a PPG signal obtained at 530 nm. Though these PPG signals at 530 nm and 940 nm were used in this example, other PPG signals of other wavelengths may also be implemented. For example, for the cross correlation a PPG signal with a wavelength in the IR spectrum and another with a wavelength in the UV spectrum may be used. In this example of a person with patient with blood Type AB and RH−, the average value of the cross-correlation and the auto-correlation is approximately 0.2.

Figure 23B:
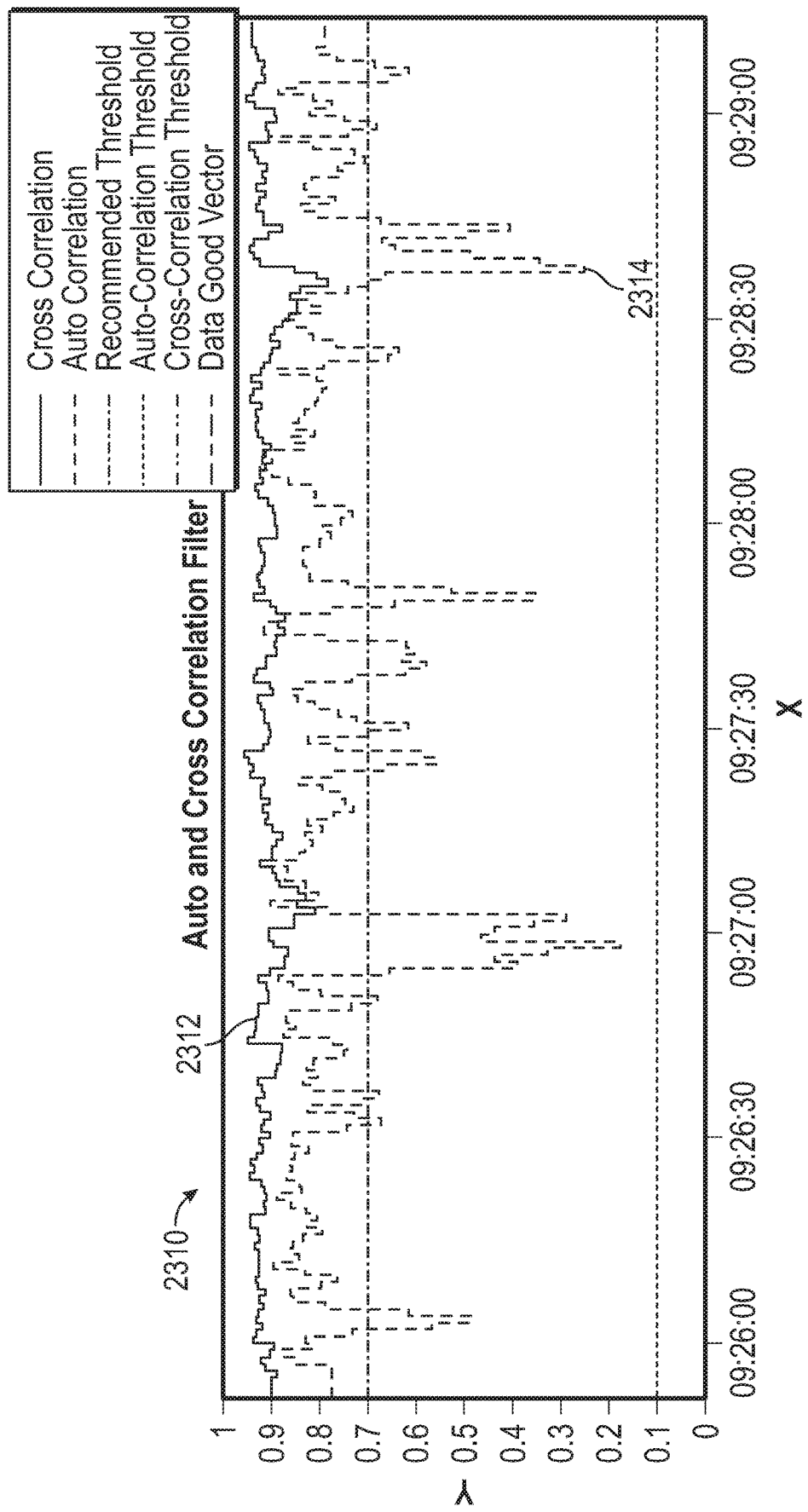
FIG. 23B illustrates a schematic graph of an example of clinical data of signal quality parameters for detecting blood type in a patient with blood Type B and RH−.

FIG. 23B illustrates a schematic graph 2310 of an example of clinical data of signal quality parameters for detecting blood type in a patient with blood Type B and RH−. In this example, the signal quality parameters include a cross-correlation 2312 and an auto-correlation 2314 of PPG signals. Preferably, when determining a blood type, the PPG signals and signal quality parameters are obtained at a same or similar gain as the PPG signals and signal quality parameters of other patients. Thus, the automatic gain control is disabled and a uniform gain or no gain is applied to the detected PPG signal.

The cross correlation 2312 illustrates a cross correlation of a PPG signal obtained at 530 nm and a PPG signal obtained at 940 nm. The auto-correlation 2314 illustrates an auto-correlation of a PPG signal obtained at 530 nm. Though these PPG signals at 530 nm and 940 nm were used in this example, other PPG signals of other wavelengths may also be implemented. For example, for the cross correlation, a PPG signal with a wavelength in the IR spectrum and another with a wavelength in the UV spectrum may be used. In this example of a person with patient with blood Type B and RH−, the average value of the cross-correlation and the auto-correlation is around 0.9.

Figure 24A:
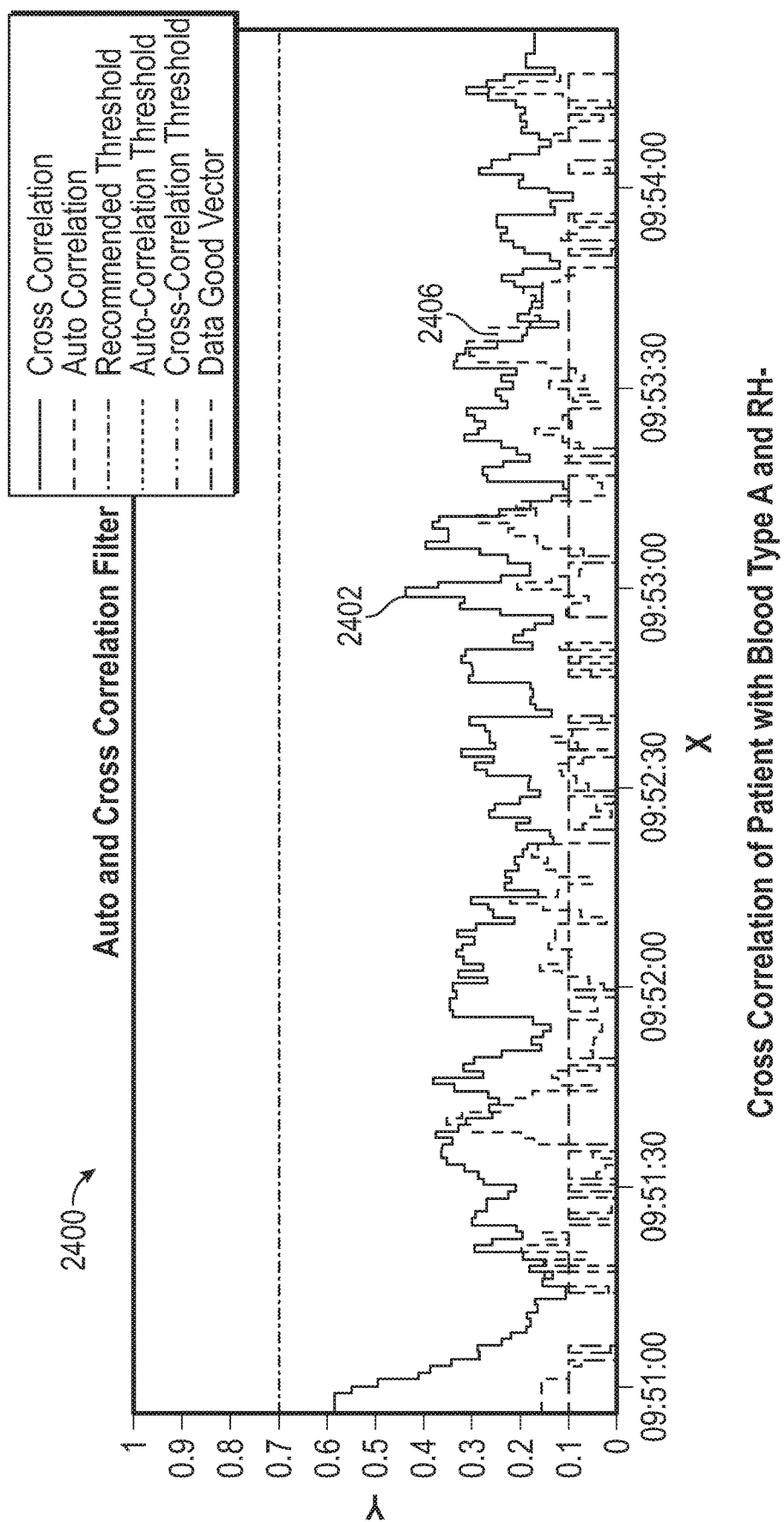
FIG. 24A illustrates a schematic graph of an example of clinical data of signal quality parameters for detecting blood type in a patient with blood Type A and RH−.

FIG. 24A illustrates a schematic graph 2400 of an example of clinical data of signal quality parameters for detecting blood type in a patient with blood Type A and RH−. In this example, the signal quality parameters include a cross-correlation 2402 and an auto-correlation 2406 of PPG signals. Preferably, when determining a blood type, the PPG signals and signal quality parameters are obtained at a same or similar gain as the PPG signals and signal quality parameters of other patients, e.g. as in FIGS. 23A and 23B. Thus, the automatic gain control is disabled and a uniform gain or no gain is applied to the detected PPG signal for determining a blood type.

The cross correlation 2402 illustrates a cross correlation of a PPG signal obtained at 530 nm and a PPG signal obtained at 940 nm. The auto-correlation 2406 illustrates an auto-correlation of a PPG signal obtained at 530 nm. Though these PPG signals at 530 nm and 940 nm were used in this example, other PPG signals of other wavelengths may also be implemented. For example, for the cross correlation function, a PPG signal with a wavelength in the visible spectrum (e.g., 660 nm) and another with a wavelength in the IR spectrum (e.g., 940 nm) may be used. In this example of a person with patient with blood Type A and RH−, the average value of the cross-correlation and the auto-correlation is around 0.3.

Figure 24B:
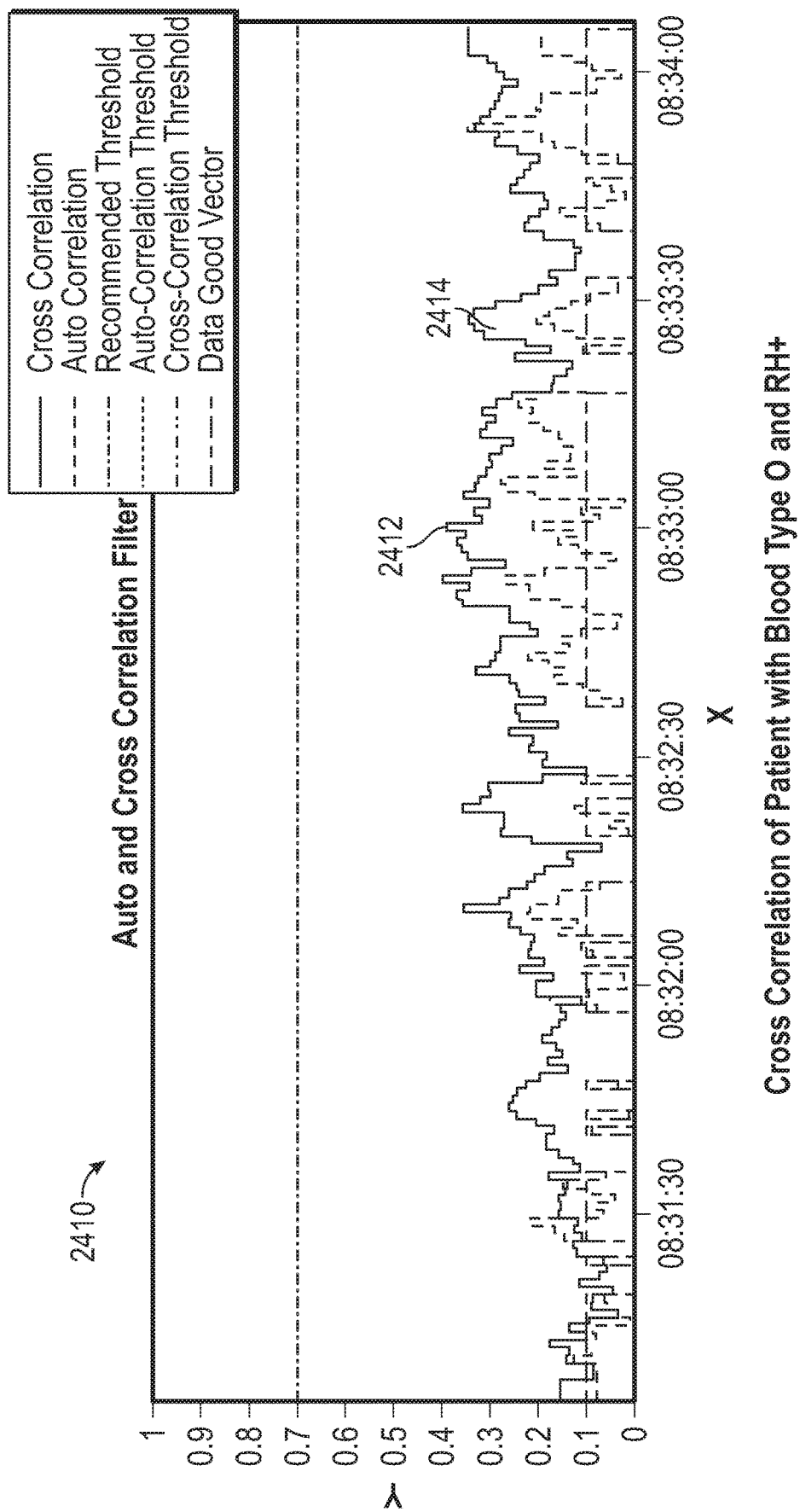
FIG. 24B illustrates a schematic graph of an example of clinical data of signal quality parameters for detecting blood type in a patient with blood type O and RH+.

FIG. 24B illustrates a schematic graph 2410 of an example of clinical data of signal quality parameters for detecting blood type in a patient with blood type O and RH+. In this example, the signal quality parameters include a cross-correlation 2412 and an auto-correlation 2414 of PPG signals. Preferably, when determining a blood type, the PPG signals and signal quality parameters are obtained at a same or similar gain as the PPG signals and signal quality parameters of other patients, e.g. as in FIGS. 23A, 23B and 24A. Thus, the automatic gain control is disabled and a uniform gain or no gain is applied to the detected PPG signal for determining a blood type.

The cross correlation 2412 illustrates a cross correlation of a PPG signal obtained at 530 nm and a PPG signal obtained at 940 nm. The auto-correlation 2414 illustrates an auto-correlation of a PPG signal obtained at 530 nm. Though these PPG signals at 530 nm and 940 nm were used in this example, other PPG signals of other wavelengths may also be implemented. For example, for the cross correlation, a PPG signal with a wavelength in the IR spectrum and another with a wavelength in the UV spectrum may be used. In this example of a person with patient with blood Type O and RH+, the average value of the cross-correlation and the auto-correlation is around 0.23.

Figure 25:
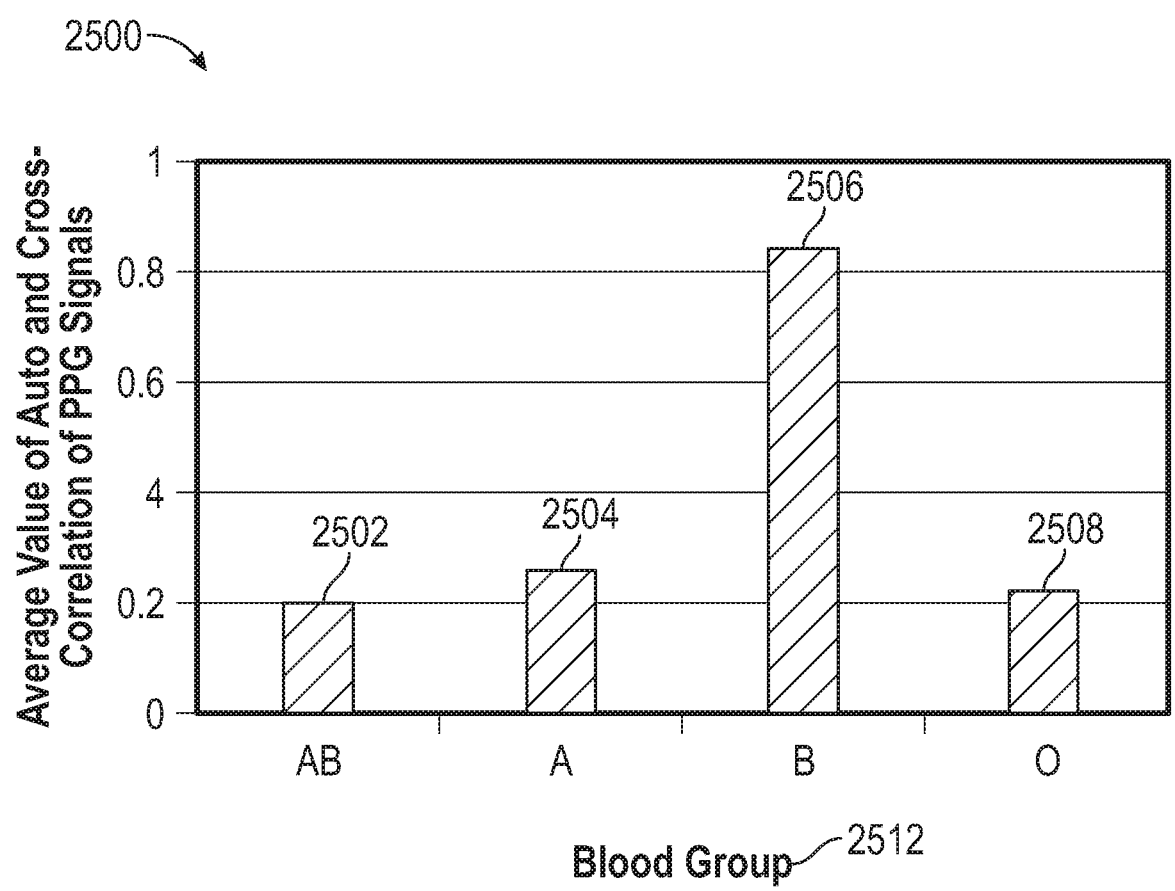
FIG. 25 illustrates a schematic graph of an embodiment of predetermined signal quality parameters for obtaining a blood type in a patient.

FIG. 25 illustrates a schematic graph 2500 of an embodiment of predetermined signal quality parameters for obtaining a blood type in a patient. In this graph 2500, the average values 2510 of the auto and cross-correlations of PPG signals from various blood types 2512 is illustrated. The predetermined average values include, e.g., an approximate 0.2 average for AB Blood group 2502, an approximate 0.3 average for A blood group 2504, an approximate 0.9 average for B blood group 2506, and an approximate 0.23 average for O blood group 2508. Though the approximate averages are shown, a range of average values may be predetermined for the different blood groups. Alternatively, a mean, threshold value, or other parameter derived from the auto or cross correlation functions may be implemented.

In use, PPG signals are obtained from a patient at a plurality of wavelengths. The automatic gain control is disabled, and a uniform gain or no gain is applied to the PPG signal. The average value of the auto-correlation and cross correlation functions for the PPG signals are determined over a measurement window (such as 2-10 cardiac cycles). The obtained average value is compared to predetermined average values of the auto-correlation and cross correlation functions for each blood group. Based on the comparison, a blood group for the patients is determined. Thus, a signal quality parameter may be implemented as another blood type indicator. The predetermined values of the signal quality parameters may be stored in the calibration database 1800.

Figure 26:
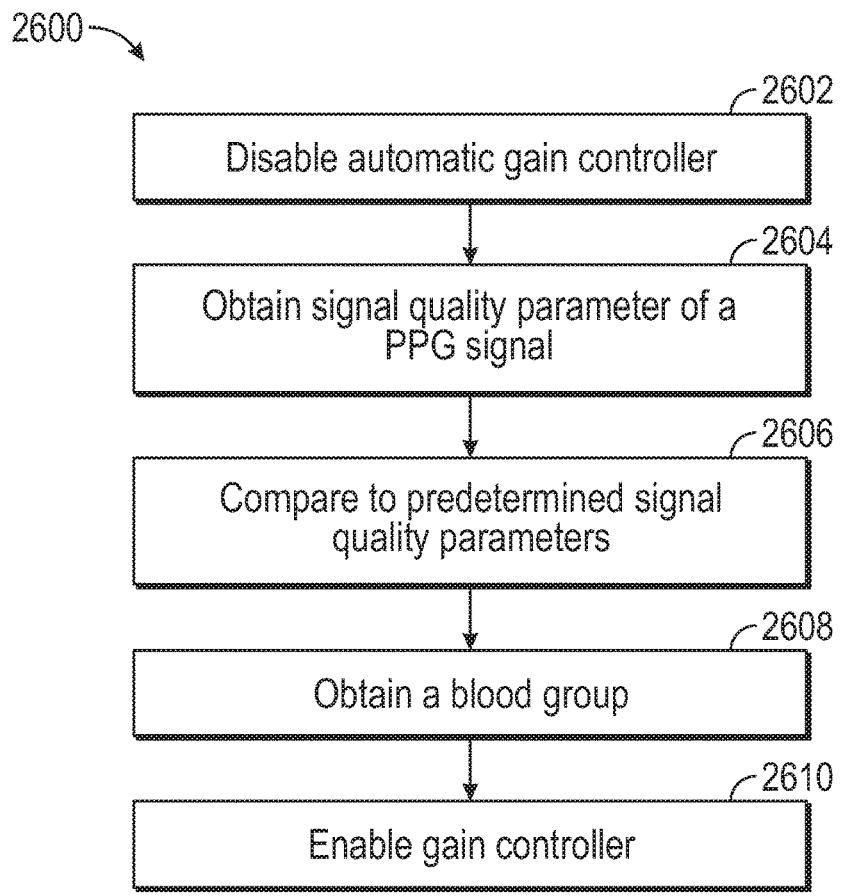
FIG. 26 illustrates a logical flow diagram of an embodiment of a method for determining a blood group of a patient based on a signal quality parameter of a PPG signal.

FIG. 26 illustrates a logical flow diagram of an embodiment of a method 2600 for determining a blood group of a patient based on a signal quality parameter of a PPG signal. The state of the gain controller is changed or disabled at 2602. For example, the automatic gain control is disabled, and a uniform gain or no gain is applied to the PPG signal across patients when determining blood group. In general, the PPG signal should have no gain applied or a similar gain applied for consistent measure and comparison of signal quality for blood typing.

One or more signal quality parameters are measured using one or more PPG signals at one or more wavelengths at 2604. The signal quality parameters may relate to signal quality and/or signal strength of the PPG signal. For example, a signal to noise ratio of a PPG signal with a wavelength in an IR range may be determined. An average value of an auto-correlation of a PPG signal may be determined or a cross-correlation of two PPG signals at two different wavelengths may be determined. Other signal quality parameters may also be implemented to determine different blood types, such as a skewness index ($S_{SQI}$), a kurtosis index ($K_{SQI}$), entropy ($E_{SQI}$), relative power, or other indices of signal quality or strength.

Though the signal quality parameter of the PPG signal $I_{AC+DC}$ is illustrated herein, the signal quality parameter may be measured from an isolated $I_{AC}$ component of the PPG signal. For example, melatonin or other skin tone differences may affect the $I_{DC}$ component of the PPG signal, but the $I_{AC}$ component reflects the pulsating volume of arterial or venous blood. The signal quality parameter of the isolated $I_{AC}$ component of the PPG signal may thus be used to determine a blood type as well.

The one or more measured signal quality parameters are compared to predetermined signal quality parameters for the one or more blood groups at 2606. For example, a calibration database 1800 may be accessed that associates values of predetermined signal quality parameters to a plurality of blood groups (e.g., types of antigens on surfaces of red blood cells). Based on the comparison, a blood group is obtained for the user. The blood group may be determined based on a single comparison or multiple comparisons.

Upon completion of the blood typing process, the state of the automatic gain controller may be changed or enabled at 2610. For example, the automatic gain controller or other varied gain may be applied to the PPG signal for determination of other patient vitals.

Figure 27:
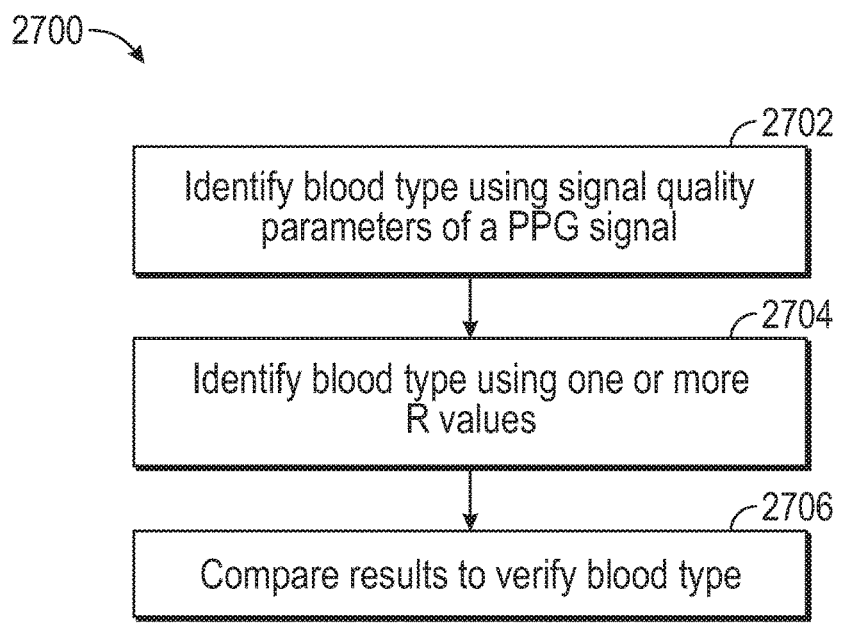
FIG. 27 illustrates a logical flow diagram of an embodiment of a method for determining a blood group of a patient using PPG technology.

FIG. 27 illustrates a logical flow diagram of an embodiment of a method 2700 for determining a blood group of a patient using PPG technology. The biosensor 100 may be configured to identify the blood group of a patient, human or animal, using one or more different types of methods. A first identification of a blood type or group of a patient may be determined using signal quality parameters of a PPG signal at 2702. A second identification of the blood type or group of a patient may also be determined using one or more R values at 2704. The first identification and the second identification from the two methods may be compared to verify the blood type of the patient at 2706. When the first and second identifications differ, one or more of the methods of identification may be repeated. When the results are still different, an error may be generated.

The biosensor 100 is thus able to non-invasively determine the blood type of a patient using PPG technology. The biosensor 100 provides a quick, convenient and easy to use tool for blood typing.

Embodiment—Adjustment of Measurements Based on Blood Type

The blood type varies the color of blood and may affect measurements of a PPG circuit 110, including measurements of $SpO_2$ and other substances. For example, the R ratio derived from a 660 nm spectral response varies in response to a blood type of a patient. Thus, depending on the blood type, the average R value of a patient may differ and affect the SpO2 measurement.

In an embodiment herein, the biosensor 100 calibrates one or more measurements using the blood type of a patient. For example, the biosensor 100 may use the blood type of the patient as a factor in calibration tables when determining $SpO_2$. In use, the biosensor 100 obtains a blood type of a patient. The biosensor 100 then obtains a first spectral response around approximately 660 nm and a second spectral response around approximately 940 nm and determines a ratio $R_{660/940}$. The biosensor 100 then accesses a calibration table to determine an $SpO_2$ value using the ratio $R_{660/940}$ and blood type. The calibration table includes a different correlation between oxygen saturation $SpO_2$ values and R values for different blood types.

Figure 28A:
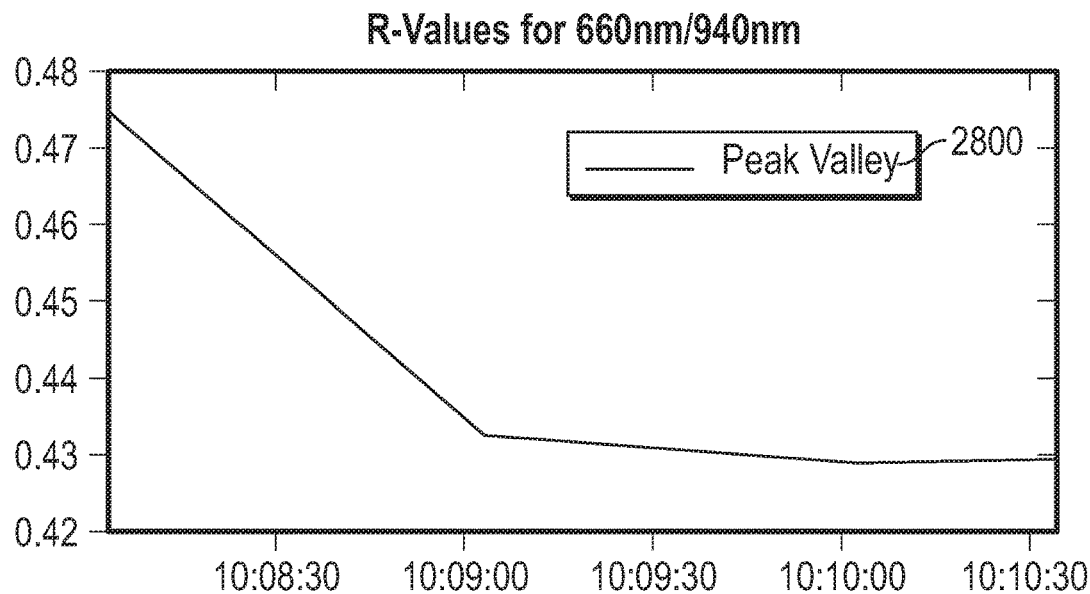
FIG. 28A illustrates a schematic graph of an example $R_{660/940}$ values for a patient with blood type AB and RH factor— and with an $SpO_2$ of 97%.

FIG. 28A illustrates a schematic graph of an example $R_{660/940}$ values 2800 for a patient with blood type AB and RH factor—and with an $SpO_2$ of 97%. In this example, the patient was determined to have an oxygen saturation level $SpO_2$ of 97%. The biosensor 100 obtained a first spectral response around approximately 660 nm and a second spectral response around approximately 940 nm and determined the $R_{660/940}$ values 2800 over a measurement window. The average $R_{660/940}$ value over the measurement window was approximately 0.43 for the patient with blood type AB–.

Figure 28B:
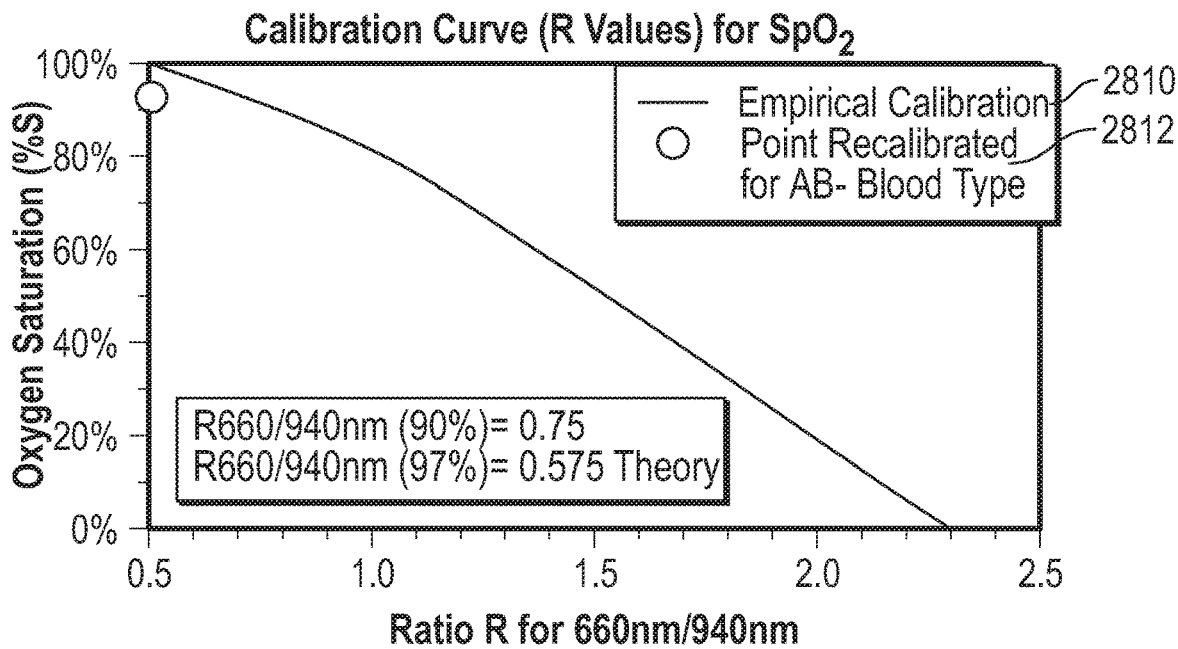
FIG. 28B illustrates a schematic graph of an established calibration curve between $R_{660/940}$ values and oxygen saturation $SpO_2$.

FIG. 28B illustrates a schematic graph of an established calibration curve 2810 between $R_{660/940}$ values and oxygen saturation $SpO_2$. According to the established calibration curve 2810, the $R_{660/940}$ value for a patient with an oxygen saturation $SpO_2$ of 97% is about 0.575. Thus, the difference between the theoretical $R_{660/940}$ value of 0.575 and the measured $R_{660/940}$ value for the patient with blood type AB– is approximately –0.145. The calibration curve 2810 may thus be recalibrated as shown with point 2812 for AB– blood type. Point 2812 recalibrates an oxygen saturation $SpO_2$ of 97% to approximately 0.43. This recalibration may be performed for differing oxygen saturation $SpO_2$ values and R values for patients with AB– blood type.

Figure 29A:
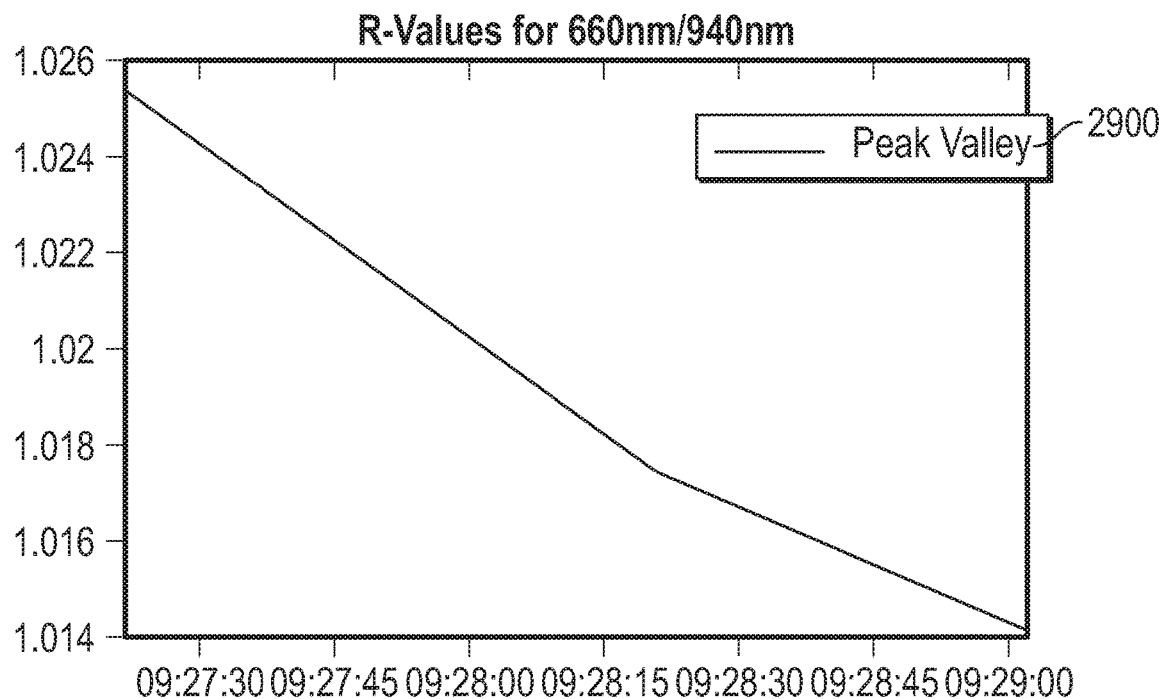
FIG. 29A illustrates a schematic graph of an example $R_{660/940}$ values for a patient with blood type B and RH factor— and with an $SpO_2$ of 97%.

FIG. 29A illustrates a schematic graph of an example $R_{660/940}$ values 2900 for a patient with blood type B and RH factor—and with an $SpO_2$ of 97%. In this example, the patient was determined to have an oxygen saturation level $SpO_2$ of 97%. The biosensor 100 obtained a first spectral response around approximately 660 nm and a second spectral response around approximately 940 nm and determined the $R_{660/940}$ values 2900 over a measurement window. The average $R_{660/940}$ value over the measurement window was approximately 1.02 for the patient with the B– blood type.

Figure 29B:
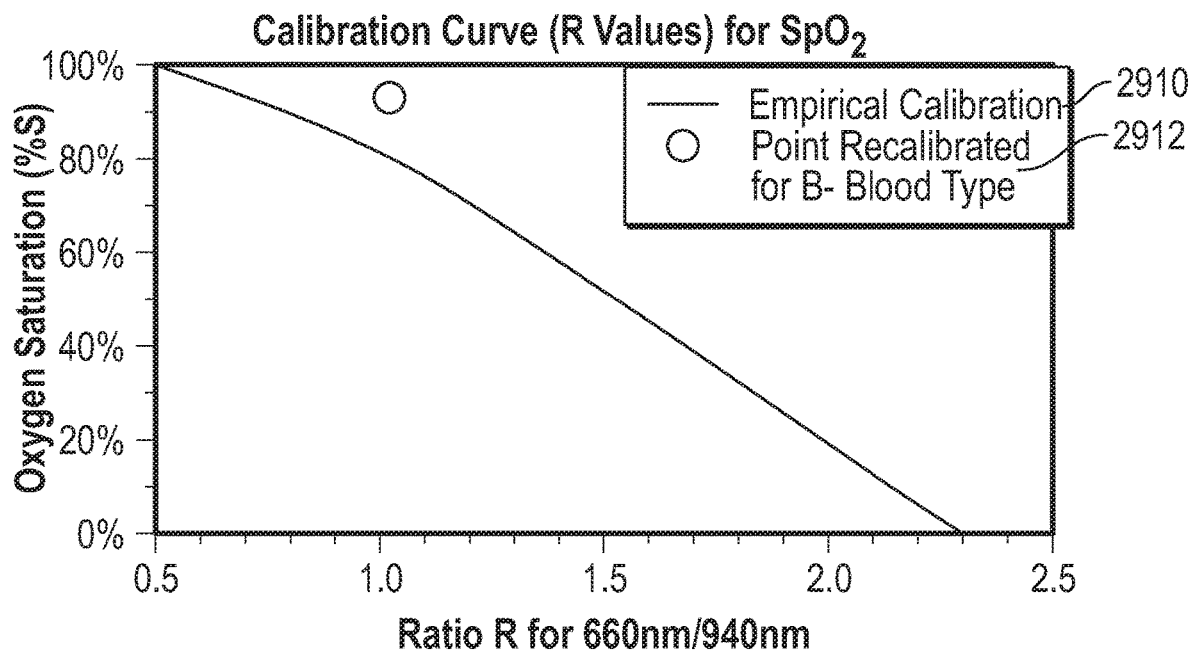
FIG. 29B illustrates a schematic graph of an established calibration curve between $R_{660/940}$ values and oxygen saturation $SpO_2$.

FIG. 29B illustrates a schematic graph of an established calibration curve 2910 between $R_{660/940}$ values and oxygen saturation $SpO_2$. According to the established calibration curve 2910, the $R_{660/940}$ value for a patient with an oxygen saturation $SpO_2$ of 97% is about 0.575. Thus, the difference between the theoretical $R_{660/940}$ value of 0.575 and the measured $R_{660/940}$ value for the patient with blood type B– is approximately 0.445. The calibration curve 2910 may thus be recalibrated as shown with point 2912 for B– blood type. Point 2912 recalibrates an oxygen saturation $SpO_2$ of 97% to approximately 1.02. This recalibration may be performed for differing oxygen saturation $SpO_2$ values and R values to generate a calibration curve for patients with B– blood type.

Figure 30A:
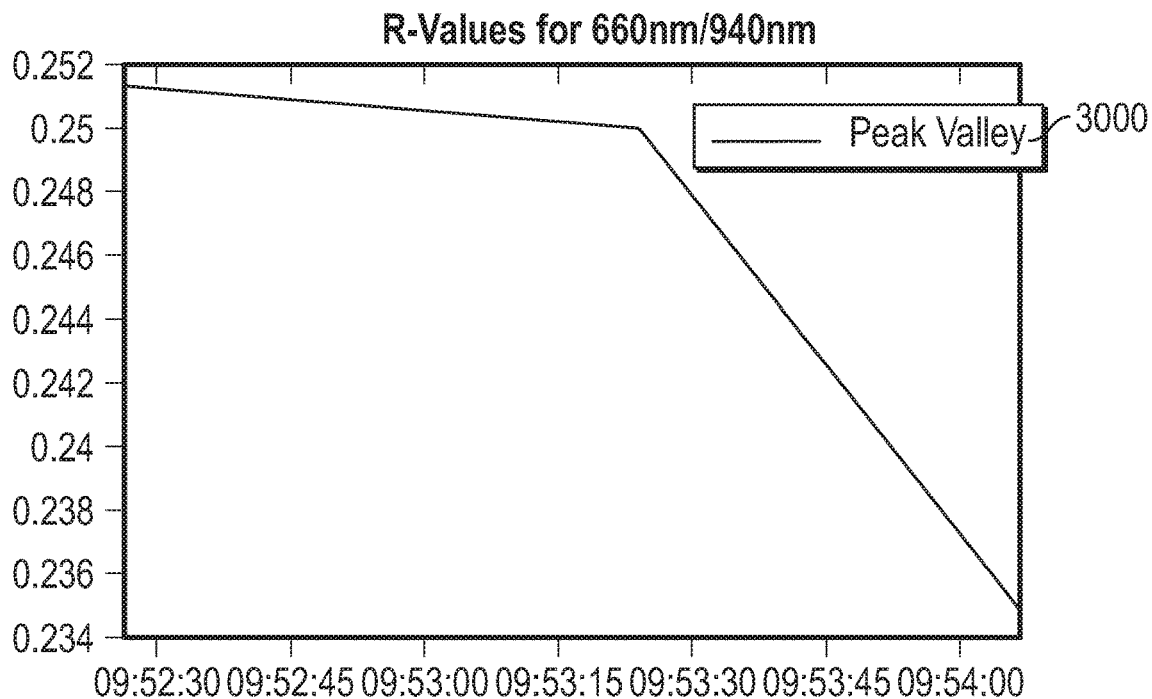
FIG. 30A illustrates a schematic graph of an example $R_{660/940}$ values for a patient with blood type A and RH factor— and with an $SpO_2$ of 97%.

FIG. 30A illustrates a schematic graph of an example $R_{660/940}$ values 3000 for a patient with blood type A and RH factor—and with an $SpO_2$ of 97%. In this example, the patient was determined to have an oxygen saturation level $SpO_2$ of 97%. The biosensor 100 obtained a first spectral response around approximately 660 nm and a second spectral response around approximately 940 nm and determined the $R_{660/940}$ values 3000 over a measurement window. The average $R_{660/940}$ value over the measurement window was approximately 0.242 for the patient with the A– blood type.

Figure 30B:
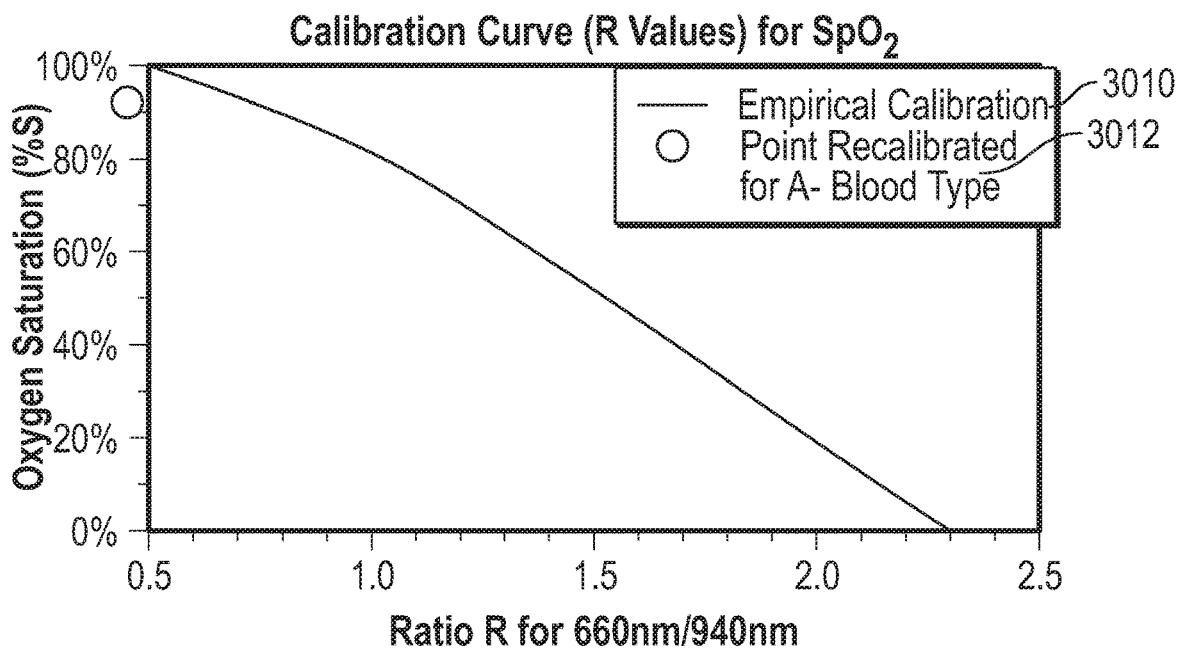
FIG. 30B illustrates a schematic graph of an established calibration curve between $R_{660/940}$ values and oxygen saturation $SpO_2$.

FIG. 30B illustrates a schematic graph of an established calibration curve 3010 between $R_{660/940}$ values and oxygen saturation $SpO_2$. According to the established calibration curve 3010, the $R_{660/940}$ value for a patient with an oxygen saturation $SpO_2$ of 97% is about 0.575. Thus, the difference between the theoretical $R_{660/940}$ value of 0.575 and the measured $R_{660/940}$ value for the patient with blood type B– is approximately –0.333. The calibration curve 3010 may thus be recalibrated as shown with point 3012 for A– blood type. Point 3012 recalibrates an oxygen saturation $SpO_2$ of 97% to approximately 0.242. This recalibration may be performed for differing oxygen saturation $SpO_2$ values and R values to generate a calibration curve for patients with A– blood type.

Figure 31A:
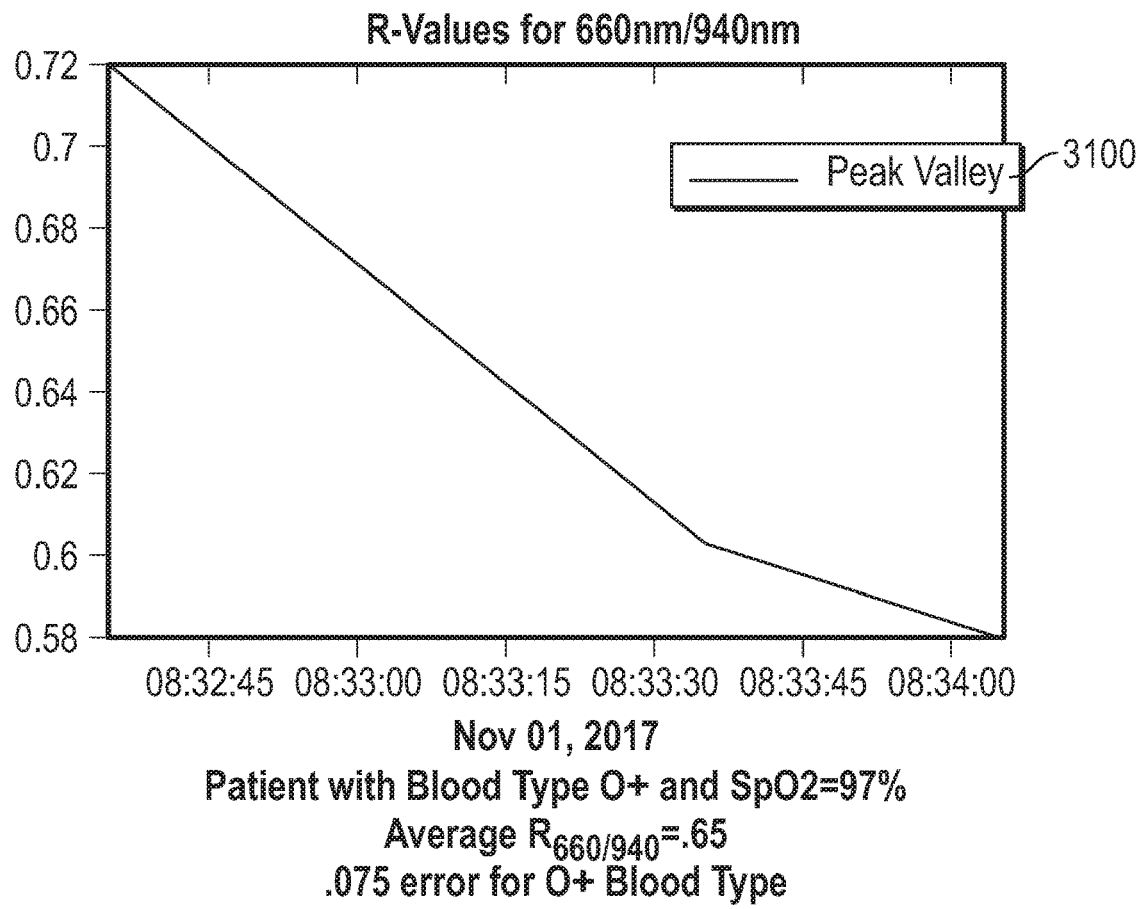
FIG. 31A illustrates a schematic graph of an example $R_{660/940}$ values for a patient with blood type O and RH factor+ and with an $SpO_2$ of 97%.

FIG. 31A illustrates a schematic graph of an example $R_{660/940}$ values 3100 for a patient with blood type O and RH factor+ and with an $SpO_2$ of 97%. In this example, the patient was determined to have an oxygen saturation level $SpO_2$ of 97%. The biosensor 100 obtained a first spectral response around approximately 660 nm and a second spectral response around approximately 940 nm and determined the $R_{660/940}$ values 3100 over a measurement window. The average $R_{660/940}$ value over the measurement window was approximately 0.65 for the patient with the O+ blood type.

Figure 31B:
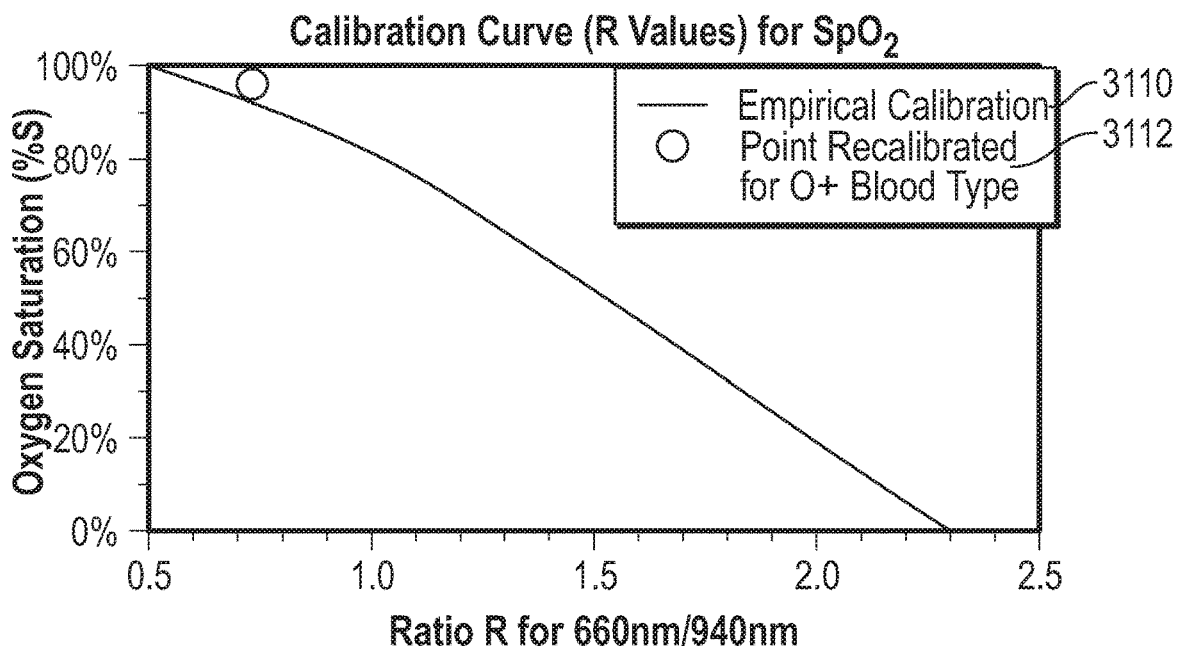
FIG. 31B illustrates a schematic graph of an established calibration curve between $R_{660/940}$ values and oxygen saturation $SpO_2$.

FIG. 31B illustrates a schematic graph of an established calibration curve 3110 between $R_{660/940}$ values and oxygen saturation $SpO_2$. According to the established calibration curve 3110, the $R_{660/940}$ value for a patient with an oxygen saturation $SpO_2$ of 97% is about 0.575. Thus, the difference between the theoretical $R_{660/940}$ value of 0.575 and the measured $R_{660/940}$ value for the patient with blood type O+ is approximately 0.075. The calibration curve 3010 may thus be recalibrated as shown with point 3112 for O+ blood type. Point 3112 recalibrates an oxygen saturation $SpO_2$ of 97% to approximately 0.65. This recalibration may be performed for differing oxygen saturation $SpO_2$ values and R values to generate a calibration curve for patients with O+ blood type.

FIG. 32 illustrates a schematic graph 3200 of an error value of example $R_{660/940}$ values for patients with various blood types at an $SpO_2$ of 97%. According to the established calibration curve, the $R_{660/940}$ value for a patient with an oxygen saturation $SpO_2$ of 97% is about 0.575. However, as described herein, the measured average $R_{660/940}$ value for a patient with an oxygen saturation $SpO_2$ of 97% differs depending on the blood type of the patient. For example, the error is approximately –0.145 for AB– blood type, approximately 0.445 for A– blood type, approximately –0.333 for B– blood type and approximately 0.075 for O+ blood type. The empirical data must thus be recalibrated for blood type, especially in PPG signals obtained from reflectance mode.

The spectral responses in FIGS. 28-31 were detected from reflected light in a reflectance mode of operation of the biosensor 100. In general, it was determined that spectral responses obtained from reflectance include a greater degree of error than from transmissive light in the $R_{660/940}$ values. Thus, to obtain more accurate readings of oxygen saturation levels, calibration curves or tables need to be used for different blood types.

FIG. 33 illustrates a logical flow diagram of an embodiment of a method 3300 for determining a calibration curve of $SpO_2$ for a blood type. The blood type of a general population is tested to identify a group of patients with a specific blood type at 3302. The average $R_{660/940}$ value for a patient is determined and the $SpO_2$ level using a reliable method independent of PPG technology at 3304. A range of $SpO_2$ levels are determined with corresponding average $R_{660/940}$ values for the patients with a specific blood type. A recalibration error may be determined to a standard calibration curve at 3306 for the specific blood type. The recalibration error may vary depending on the $SpO_2$ level. Alternatively or in addition thereto, a calibration curve may be generated for the specific blood type that associates the average $R_{660/940}$ values for the patients with the measured $SpO_2$ level. Though the average $R_{660/940}$ values are illustrated herein, other R values may also be correlated to $SpO_2$ levels for a specific blood type, e.g. $R_{590/940}$ or $R_{660/920}$, etc.

Though described herein for $SpO_2$ levels, a similar calibration process may be performed for other patient vitals. For example, the biosensor 100 determines a patient vital using a known method and then determines an average R value of the patient. The biosensor 100 correlates the average R value to the value of the patient vital for the blood type of the user. The biosensor 100 may then store the correlation in a calibration table for the specific blood type in a calibration database 1800. The patient vital may include a concentration level of nitric oxide (NO) in the blood stream, a concentration level of a liver enzyme in the blood stream, a concentration level of glucose, a concentration level of an electrolyte, a concentration of one or more species of hemoglobin, or a concentration level of another substance in the blood stream.

Figure 34:
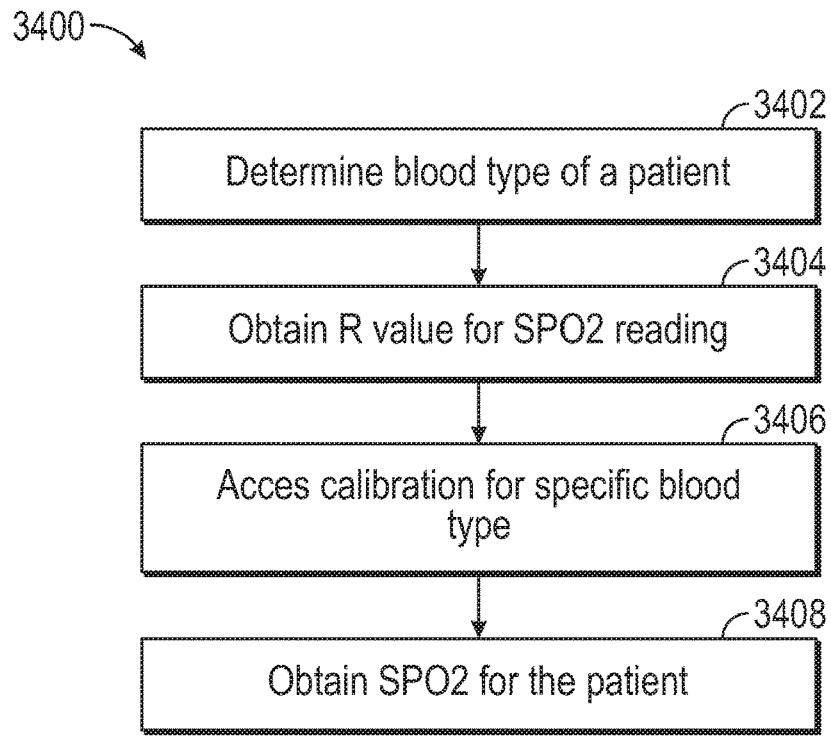
FIG. 34 illustrates a logical flow diagram of a method for determining an oxygen saturation level of a patient.

FIG. 34 illustrates a logical flow diagram of a method 3400 for determining an oxygen saturation level of a patient. The blood type of the patient is obtained at 3402. The patient may input a known blood type or the biosensor 100 may one or more methods as described herein to obtain the blood type of the patient. The value for an R ratio for an $SpO_2$ measurement are obtained at 3404, e.g., the average $R_{660/940}$ values or other R values correlated to $SpO_2$ levels, e.g. $R_{590/940}$ or $R_{660/920}$, etc. A calibration table or curve that includes calibration values for a specific blood type between the R value and $SpO_2$ level is then accessed at 3406. The $SpO_2$ measurement is then obtained for the patient at 3408.

The blood type of a patient may affect measurements other than oxygen saturation $SpO_2$. For example, measurements using PPG technology of nitric oxide (NO) levels, liver enzyme (P450) levels, etc. may be affected by blood type. The biosensor 100 may thus determine calibrations based on blood type for one or more different types of measurements, as shown the calibration database 1800 in FIG. 18.

Alternatively, other types of measurements (e.g., absorption spectra shift) using a plurality of spectral responses may be calibrated based on blood type. For example, the calibration database 1800 may include different values for an R ratio that correlate to a patient vital for different blood groups. In another example, the calibration database 1800 may include different values for an absorption spectra shift that correlate to a patient vital for different blood groups. The patient vital may include an oxygen saturation level, a concentration level of another substance, or other measurement.

Figure 35:
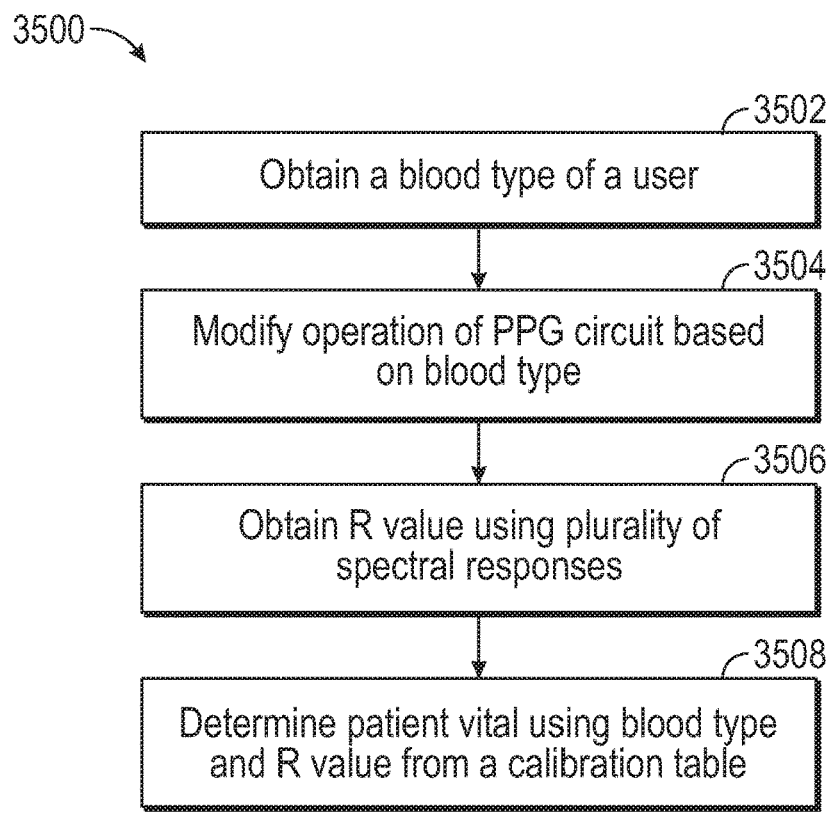
FIG. 35 illustrates a logical flow diagram of a method for determining a patient measurement using a blood type of the patient.

FIG. 35 illustrates a logical flow diagram of a method 3500 for determining a patient measurement using a blood type of the patient. The biosensor 100 obtains a blood type of the patient at 3502. A known blood type of the patient may be input or stored in a database of the biosensor 100, or the biosensor 100 may use the PPG circuit 110 as described herein to obtain the blood type of the patient.

Based on the blood type, the biosensor 100 may modify operation of the PPG circuit 110 or other components of the biosensor 100 at 3504. For example, a different frequency, amplification or intensity of light may be used to obtain one or more spectral responses depending on the blood type. The biosensor 100 then obtains values for an R ratio or other type of measurements (e.g., absorption spectra shift) using a plurality of spectral responses at 3506. Based on the measurement and the blood type, a patient vital is determined from a calibration table stored in a calibration database 1800. The calibration database 1800 includes calibrations based on blood type of the user, e.g., a plurality of calibrations that associate predetermined ratio R values to a patient vital for a plurality of specific blood types. For example, the calibration table may include a correlation of R ratio values to $SpO_2$ levels for a plurality of different blood groups. In another example, the calibration table may include values for an absorption spectra shift that correlate to a patient vital for different blood groups. The patient vital may include an oxygen saturation $SpO_2$, a concentration level of nitric oxide (NO) in the blood stream, a concentration level of a liver enzyme in the blood stream, a concentration level of glucose, a concentration level of an electrolyte, a concentration of one or more species of hemoglobin, or a concentration level of another substance in the blood stream.

Figure 36:
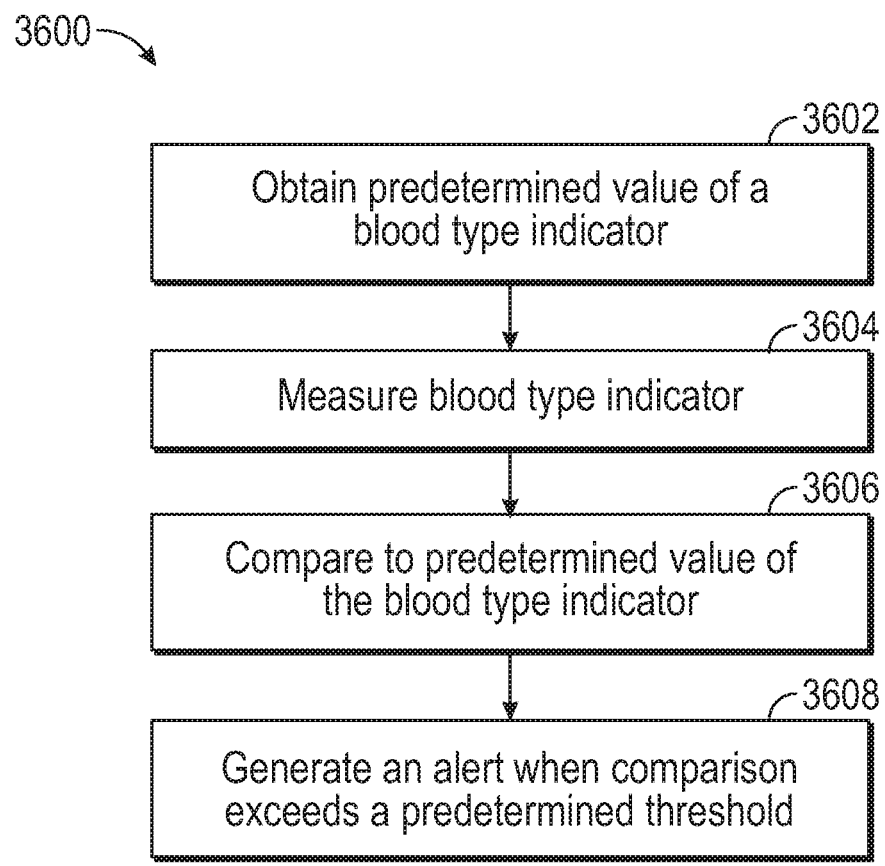
FIG. 36 illustrates a logical flow diagram of an exemplary embodiment of a method for detecting an abnormal condition.

FIG. 36 illustrates a logical flow diagram of an exemplary embodiment of a method 3600 for detecting an abnormal condition. In an embodiment, an abnormal condition may be detected upon a change of a predetermined value of a blood type indicator. For example, the biosensor 100 may store a known blood type of a user or an average or normal value for a blood type indicator of the user. When the expected or normal value of the blood type indicator of the user changes, it may signal an abnormal condition. In particular, various conditions may affect the red blood cells, such as a Hemolytic or Non-Hemolytic staph infection. The red blood cells (RBCs) exhibit abnormal optical properties in hemolytic staph infections versus Non-Hemolytic varieties of Staph. For example, the RBC exhibit an abnormal composition since a destruction of RBCs occurs during the infection period.

Hemolysis is the rupturing of RBCs and the release of their contents (cytoplasm) into surrounding fluid (e.g. blood plasma). So, an abnormal count and color of the RBCs can be observed in the PPG signal of a spectral response. If as little as 0.5% of the red blood cells are hemolyzed, the released hemoglobin will cause the serum or plasma to change color, e.g. appear pale red or cherry red in color. The PPG circuit may measure the effect of hemolysis due to the color change and determine an abnormal condition.

Additionally, the biosensor 100 may non-invasively measure a temperature of a patient, at periodic intervals, e.g. one or more times per minute. The biosensor 100 may also monitor liver enzyme levels or nitric oxide (NO) levels in blood flow of a user, at periodic intervals, e.g. one or more times per minute. The PPG circuit may also determine other user vitals, such as heart rate, vasodilation and respiration rate. The one or more various measured parameters are compared to predetermined thresholds to determine an abnormal condition is present, such as an infection, anemia, genetic disease (e.g., sickle cell anemia), malaria, snake venom, toxic chemicals, tick-borne diseases, or blackwater fever.

In an embodiment, a predetermined value of a blood type indicator is obtained by the biosensor 100 at 3602. For example, the biosensor 100 may store a measured blood type indicator of a user in a memory device 104. Alternatively, a blood type (ABO and/or RH factor) of the user is stored in a memory device or communicated to the biosensor 100 via user input or from another device. The biosensor 100 may then determine a predetermined range of a blood type indicator from the blood type and a calibration database. For example, the biosensor 100 may access the calibration database to determine an expected range of values for an $R_{530/940}$ ratio or $R_{590/940}$ ratio value or a signal quality parameter for a specific blood type.

The biosensor 100 then measures the blood type indicator of the user at 3604 using one or more methods described herein. The blood type indicator may include an R ratio value, signal quality parameter or other parameter derived from a PPG signal of a spectral response. The measured blood type indicator is compared to the predetermined value of the blood type indicator at 3606. The predetermined value of the blood type indicator may include a normal range or threshold for the blood type indicator. The predetermined value may include an expected value of the indicator for the specific blood type stored in the calibration database. Or the predetermined value may be based on differences from one or more stored values of previous measurements for the user, such as a percentage difference or other predetermined threshold.

When the measured blood type indicator is not within a normal range, an alert may be generated at 3608. The alert may indicate that the blood type indicator is not within a normal range for the user or exceeds expected values for the specific blood type stored in the calibration database. The biosensor 100 thus determines an abnormal condition and generates an error or alert message.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above about particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A biosensor, comprising:
an optical sensor circuit configured to obtain a plurality of spectral responses at a plurality of wavelengths detected from skin of a user;
a processing circuit configured to:
obtain a blood type of a user;
determine a first ratio R value using a first spectral response and a second spectral response of the plurality of spectral responses;
access a calibration database for the blood type of the user, wherein the calibration database associates predetermined ratio R values to patient vitals for each of a plurality of blood types; and
obtain a patient vital of the user using the first ratio R value, the calibration database and the blood type of the user.

2. The biosensor of claim 1, wherein the patient vital includes at least one of: oxygen saturation ($SpO_2$), a concentration level of nitric oxide (NO), a concentration level of a liver enzyme, a concentration level of glucose, a concentration level of an electrolyte, a concentration of one or more species of hemoglobin, or a concentration level of another substance in a blood flow of the user.

3. The biosensor of claim 2, wherein the calibration database includes a plurality of $SpO_2$ calibrations, wherein each of the plurality of $SpO_2$ calibrations associates a predetermined ratio R value to an oxygen saturation level for a different one of a plurality of blood types.

4. The biosensor of claim 1, wherein the processing circuit is further configured to:
determine an absorption spectra shift using a third spectral response and a fourth spectral response of the plurality of spectral responses;
access the calibration database, wherein the calibration database includes a plurality of calibrations that associate the absorption spectra shift to the patient vital for the plurality of specific blood types; and
obtain the patient vital of the user using the absorption spectra shift, the calibration database and the blood type of the user.

5. The biosensor of claim 1, wherein the processing circuit is configured to obtain the blood type of the user by one or more of:
receiving a user input including the blood type of the user;
accessing a memory device, wherein the memory device stores the blood type of the user; or
identifying the blood type of the user using one or more spectral responses of the plurality of spectral responses detected by the PPG circuit.

6. The biosensor of claim 1, wherein the optical sensor circuit is configured to obtain the plurality of spectral responses at the plurality of wavelengths detected from skin of the user by at least one of:
detecting reflected light from skin of the user; or
detecting transmissive light from skin of the user.

7. A device, comprising:
an optical sensor circuit configured to obtain a plurality of spectral responses at a plurality of wavelengths detected from skin of a user;
a memory device configured for storing correlations between a plurality of R values and a patient vital for each of a plurality of blood types, wherein the correlations are different between the plurality of R values and the patient vital for at least two of the plurality of blood types;
a processing circuit configured to:
obtain a blood type of the user;
determine a first ratio R value using a first spectral response and a second spectral response; and
access the memory device to obtain a correlation between the first ratio R value and the patient vital for the blood type of the user.

8. The device of claim 7, wherein the patient vital is an oxygen saturation value and wherein the memory device is configured for storing different correlations between a plurality of R values and oxygen saturation values for each of a plurality of different blood types.

9. The device of claim 7, wherein the memory device is configured for storing correlations between a plurality of R values and oxygen saturation values for each of a plurality of blood types.

10. The device of claim 9, wherein the processing circuit is configured to determine the first ratio R value using the first spectral response and the second spectral response by:
determining the first ratio R using an AC component of the first spectral response and an AC component of the second spectral response.

11. The device of claim 10, wherein the processing circuit is further configured to:
access the memory device to obtain a correlation between the first ratio R value and an oxygen saturation value for the blood type of the user; and
determine an oxygen saturation for the user using the correlation.

12. The device of claim 11, wherein the device includes a pulse oximeter included in a user device.

13. The device of claim 7, wherein the patient vital includes a concentration level of a substance in a blood flow of the user.

14. The device of claim 13, wherein the patient vital includes one or more of: a concentration level of nitric oxide (NO), a concentration level of a liver enzyme, a concentration level of an electrolyte, or a concentration of one or more species of hemoglobin.

15. The device of claim 7, wherein the processing circuit is configured to obtain a blood type of the user by at least one of:
processing a user input including the blood type of the user;
accessing the memory device, wherein the memory device is configured to store the blood type of the user; or
measuring a blood type of the user.

16. A pulse oximeter, comprising:
an optical sensor circuit configured to obtain a plurality of spectral responses at a plurality of wavelengths detected from skin of a user;
a memory device configured to store oxygen saturation levels and associated ratio R values for a plurality of blood types, wherein the oxygen saturation levels are different for the associated ratio R values for at least two different blood types of the plurality of blood types; and
a processing circuit configured to:
obtain a blood type of a user;
determine a first ratio R value using a first spectral response and a second spectral response; and
accessing the memory device and using the first ratio R value and the blood type of the user to determine an oxygen saturation level for the user.

17. The pulse oximeter of claim 16, wherein the processing circuit is configured to determine the first ratio R value from a ratio of alternating current (AC) signal components in the first spectral response and the second spectral response.

18. The pulse oximeter of claim 16, wherein the memory device is configured to store two or more of:
a first correlation of oxygen saturation levels and associated R values for an O blood type;
a second correlation of oxygen saturation levels and associated R values for an A blood type;
a third correlation of oxygen saturation levels and associated R values for a B blood type; and
a fourth correlation of oxygen saturation levels and associated R values for an AB blood type.

19. The pulse oximeter of claim 16, wherein the processing circuit configured to obtain a blood type of the user by:
   processing a user input including the blood type of the user;
   accessing the memory device, wherein the memory device is configured to store the blood type of the user; or
   measuring a blood type of the user.

\* \* \* \* \*